US008945543B2

(12) United States Patent
Igawa et al.

(10) Patent No.: US 8,945,543 B2
(45) Date of Patent: Feb. 3, 2015

(54) STABILIZER FOR PROTEIN PREPARATION COMPRISING MEGLUMINE AND USE THEREOF

(75) Inventors: Tomoyuki Igawa, Shizuoka (JP); Daisuke Kameoka, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 451 days.

(21) Appl. No.: 11/916,981

(22) PCT Filed: Jun. 9, 2006

(86) PCT No.: PCT/JP2006/311625
§ 371 (c)(1),
(2), (4) Date: Feb. 15, 2008

(87) PCT Pub. No.: WO2006/132363
PCT Pub. Date: Dec. 14, 2006

(65) Prior Publication Data
US 2009/0117097 A1    May 7, 2009

(30) Foreign Application Priority Data

Jun. 10, 2005   (JP) ................. 2005-170794

(51) Int. Cl.
| A61K 39/395 | (2006.01) |
| A61K 9/19 | (2006.01) |
| A61K 9/00 | (2006.01) |
| A61K 47/26 | (2006.01) |
| C07K 16/00 | (2006.01) |
| C07K 16/28 | (2006.01) |

(52) U.S. Cl.
CPC ............... *A61K 9/19* (2013.01); *A61K 9/0019* (2013.01); *A61K 39/39591* (2013.01); *A61K 47/26* (2013.01); *C07K 16/00* (2013.01); *C07K 16/2833* (2013.01); *C07K 16/2866* (2013.01); *C07K 2317/24* (2013.01); *C07K 2317/622* (2013.01); *C07K 2317/626* (2013.01); *C07K 2317/73* (2013.01); *C07K 2317/34* (2013.01)
USPC ..................................... 424/130.1; 424/133.1

(58) Field of Classification Search
None
See application file for complete search history.

(56) References Cited

U.S. PATENT DOCUMENTS

| 4,946,778 | A | 8/1990 | Ladner et al. |
| 5,077,216 | A | 12/1991 | Morganelli et al. |
| 5,223,241 | A | 6/1993 | Isobe et al. |
| 5,516,672 | A | 5/1996 | Yamasaki et al. |
| 5,618,920 | A | 4/1997 | Robinson et al. |
| 5,747,654 | A | 5/1998 | Pastan et al. |
| 5,780,021 | A | 7/1998 | Sobel |
| 5,789,554 | A | 8/1998 | Leung et al. |
| 5,837,242 | A | 11/1998 | Holliger et al. |
| 5,837,821 | A | 11/1998 | Wu |
| 5,840,344 | A | 11/1998 | Fukushima |
| 5,877,291 | A | 3/1999 | Mezes et al. |
| 5,885,574 | A | 3/1999 | Elliott |
| 5,892,020 | A | 4/1999 | Mezes et al. |
| 5,977,322 | A | 11/1999 | Marks et al. |
| 5,998,593 | A | 12/1999 | Huff et al. |
| 6,013,067 | A | 1/2000 | Fibbe et al. |
| 6,042,829 | A | 3/2000 | Uckun et al. |
| 6,126,980 | A | 10/2000 | Smith et al. |
| 6,132,992 | A | 10/2000 | Ledbetter et al. |
| 6,183,744 | B1 | 2/2001 | Goldenberg |
| 6,319,499 | B1 | 11/2001 | Elliott |
| 6,323,000 | B2 | 11/2001 | Briggs et al. |
| 6,342,220 | B1 | 1/2002 | Adams et al. |
| 6,361,769 | B1 | 3/2002 | Tovey |
| 6,368,596 | B1 | 4/2002 | Ghetie et al. |
| 6,579,692 | B1 | 6/2003 | Fukushima |
| 6,683,157 | B2 | 1/2004 | Briggs et al. |
| 6,699,686 | B1 | 3/2004 | Brocard et al. |
| 6,719,972 | B1 | 4/2004 | Gribben et al. |
| 6,759,043 | B2 | 7/2004 | Fukushima |
| 6,903,194 | B1 | 6/2005 | Sato et al. |
| 7,045,337 | B2 | 5/2006 | Schultz et al. |
| 7,115,373 | B2 | 10/2006 | Hashida et al. |

(Continued)

FOREIGN PATENT DOCUMENTS

| AU | 755822 | 3/1999 |
| AU | 2004/297111 | 6/2005 |

(Continued)

OTHER PUBLICATIONS

Humes et al., Am. J. of Physiol. 1987, vol. 252, No. 2 p. 246-255.*

(Continued)

*Primary Examiner* — Yunsoo Kim
(74) *Attorney, Agent, or Firm* — Fish & Richardson P.C.

(57) ABSTRACT

An objective of the present invention is to provide methods for stabilizing proteins and methods for suppressing protein aggregation, which comprise the step of adding meglumine to the proteins. Another objective of the present invention is to provide agents for suppressing protein aggregation, which comprise meglumine. Still another objective of the present invention is to provide pharmaceutical compositions comprising antibody molecules stabilized by meglumine, methods for producing the pharmaceutical compositions, and kits comprising the pharmaceutical compositions.

To achieve the objectives described above, the present inventors assessed the antibody-stabilizing effect of meglumine, an amino sugar. As a result, the inventors discovered that meglumine was useful as a stabilizer for antibody molecules and also as an excipient for freeze-dried preparations.

8 Claims, 6 Drawing Sheets

(56) References Cited

U.S. PATENT DOCUMENTS

| | | | |
|---|---|---|---|
| 7,262,278 | B2 | 8/2007 | Tawara et al. |
| 7,456,260 | B2 | 11/2008 | Rybak et al. |
| 7,691,588 | B2 | 4/2010 | Tsuchiya et al. |
| 7,749,501 | B2 | 7/2010 | Gelfand |
| 8,008,073 | B2 | 8/2011 | Tsunoda et al. |
| 8,158,385 | B2 | 4/2012 | Ozaki et al. |
| 2001/0006796 | A1 | 7/2001 | Briggs et al. |
| 2002/0028178 | A1 | 3/2002 | Hanna et al. |
| 2002/0155537 | A1 | 10/2002 | Carter et al. |
| 2002/0193571 | A1 | 12/2002 | Carter et al. |
| 2002/0197706 | A1 | 12/2002 | Nadkarni et al. |
| 2003/0073161 | A1 | 4/2003 | Briggs et al. |
| 2003/0082612 | A1 | 5/2003 | Snodgrass et al. |
| 2003/0103979 | A1 | 6/2003 | Leung et al. |
| 2003/0147894 | A1 | 8/2003 | Fukushima et al. |
| 2003/0148409 | A1 | 8/2003 | Rossi et al. |
| 2003/0157100 | A1 | 8/2003 | Fukushima et al. |
| 2003/0157577 | A1 | 8/2003 | Fukushima et al. |
| 2003/0190316 | A1 | 10/2003 | Kakuta et al. |
| 2003/0202975 | A1 | 10/2003 | Tedder |
| 2003/0211108 | A1 | 11/2003 | Fukushima et al. |
| 2004/0001828 | A1 | 1/2004 | Tuscano et al. |
| 2004/0058393 | A1 | 3/2004 | Fukishima et al. |
| 2004/0073013 | A1 | 4/2004 | Fukushima et al. |
| 2004/0091475 | A1 | 5/2004 | Tsuchiya et al. |
| 2004/0219643 | A1 | 11/2004 | Winter et al. |
| 2004/0242847 | A1 | 12/2004 | Fukushima et al. |
| 2005/0130224 | A1 | 6/2005 | Saito et al. |
| 2005/0214278 | A1 | 9/2005 | Kakuta et al. |
| 2005/0220787 | A1 | 10/2005 | Lobo |
| 2005/0267222 | A1 | 12/2005 | Iwata et al. |
| 2006/0058511 | A1 | 3/2006 | Tanikawa et al. |
| 2006/0159673 | A1 | 7/2006 | Kojima |
| 2006/0189794 | A1 | 8/2006 | Tsuchiya et al. |
| 2006/0222643 | A1 | 10/2006 | Tsunoda et al. |
| 2006/0269989 | A1 | 11/2006 | Miyazaki et al. |
| 2006/0275301 | A1 | 12/2006 | Ozaki et al. |
| 2007/0003556 | A1 | 1/2007 | Tsuchiya et al. |
| 2007/0087381 | A1 | 4/2007 | Kojima |
| 2007/0280951 | A1 | 12/2007 | Kimura et al. |
| 2007/0281327 | A1 | 12/2007 | Nakano et al. |
| 2008/0009038 | A1 | 1/2008 | Ohtomo et al. |
| 2008/0107654 | A1 | 5/2008 | Kikuchi et al. |
| 2008/0206229 | A1 | 8/2008 | Ono et al. |
| 2008/0248037 | A1 | 10/2008 | Li et al. |
| 2008/0274110 | A1 | 11/2008 | Ozaki et al. |
| 2008/0286280 | A1* | 11/2008 | Kallmeyer et al. ........ 424/141.1 |
| 2009/0022687 | A1 | 1/2009 | Matsumoto et al. |
| 2009/0028854 | A1 | 1/2009 | Igawa et al. |
| 2009/0062184 | A1 | 3/2009 | Maeda et al. |
| 2009/0162352 | A1* | 6/2009 | Adler et al. ................ 424/133.1 |
| 2009/0214535 | A1 | 8/2009 | Igawa et al. |
| 2009/0297501 | A1 | 12/2009 | Igawa et al. |
| 2009/0311718 | A1 | 12/2009 | Fukushima et al. |
| 2010/0015133 | A1 | 1/2010 | Igawa et al. |
| 2010/0040600 | A1 | 2/2010 | Yoshikubo et al. |
| 2010/0092457 | A1 | 4/2010 | Aburatani et al. |
| 2010/0092461 | A1 | 4/2010 | Matsumoto et al. |
| 2010/0150927 | A1 | 6/2010 | Kimura et al. |
| 2011/0059488 | A1 | 3/2011 | Tsunoda et al. |
| 2012/0244142 | A1 | 9/2012 | Kimura et al. |

FOREIGN PATENT DOCUMENTS

| | | |
|---|---|---|
| AU | 2002/210917 | 5/2006 |
| CA | 2272245 | 5/1998 |
| CA | 2 331 641 | 11/1999 |
| CN | 1244805 | 2/2000 |
| DE | 198 19 846 | 11/1999 |
| EP | 437 622 | 7/1991 |
| EP | 437622 | 7/1991 |
| EP | 0437622 | 7/1991 |
| EP | 0 562 125 | 9/1993 |
| EP | 0562125 | 9/1993 |
| EP | 0 721 015 | 7/1996 |
| EP | 0 774 511 | 5/1997 |
| EP | 811 691 | 12/1997 |
| EP | 1 035 132 | 9/2000 |
| EP | 1 178 826 | 2/2002 |
| EP | 1 310 252 | 5/2003 |
| EP | 1 327 681 | 7/2003 |
| EP | 1327680 | 7/2003 |
| EP | 1 369 431 | 12/2003 |
| EP | 1 396 500 | 3/2004 |
| EP | 1 475 100 | 11/2004 |
| EP | 1 475 101 | 11/2004 |
| EP | 0 969 866 | 6/2005 |
| EP | 1 561 759 | 8/2005 |
| EP | 1 712 565 | 10/2006 |
| EP | 1 757 686 | 2/2007 |
| EP | 1 870 458 | 12/2007 |
| EP | 1 925 319 | 5/2008 |
| EP | WO 2008/017394 | * 6/2008 |
| EP | 1 262 548 | 8/2008 |
| EP | 2 048 230 | 4/2009 |
| JP | 3-41033 | 2/1991 |
| JP | 5-097703 | 4/1993 |
| JP | 7-503622 | 4/1995 |
| JP | 7-236475 | 9/1995 |
| JP | 8-500979 | 2/1996 |
| JP | 9-289892 | 11/1997 |
| JP | 10-505231 | 5/1998 |
| JP | 10-508868 | 9/1998 |
| JP | 10-510842 | 10/1998 |
| JP | 11-500916 | 1/1999 |
| JP | 11-092500 | 4/1999 |
| JP | 2000-95800 | 4/2000 |
| JP | 2001/506135 | 5/2001 |
| JP | 2001-513999 | 9/2001 |
| JP | 2001-518930 | 10/2001 |
| JP | 2001-523971 | 11/2001 |
| JP | 2002-543822 | 12/2002 |
| JP | 2002-544173 | 12/2002 |
| JP | 2003-515323 | 5/2003 |
| JP | 2004-086862 | 3/2004 |
| JP | 2004-292455 | 10/2004 |
| JP | 2005-529616 | 10/2005 |
| KR | 10-2004-0085185 | 10/2004 |
| MX | 9905856 | 7/2000 |
| WO | 9100739 | 1/1991 |
| WO | WO 91/16928 | 11/1991 |
| WO | WO 92/19759 | 11/1992 |
| WO | WO 93/05799 | 4/1993 |
| WO | WO 93/06862 | 4/1993 |
| WO | WO 94/05690 | 3/1994 |
| WO | WO 94/13806 | 6/1994 |
| WO | WO 96/04925 | 2/1996 |
| WO | WO 96/24370 | 8/1996 |
| WO | WO 96/26648 | 9/1996 |
| WO | WO 96/27011 | 9/1996 |
| WO | WO 96/34892 | 11/1996 |
| WO | WO 96/36360 | 11/1996 |
| WO | WO 96/40218 | 12/1996 |
| WO | WO 97/01633 | 1/1997 |
| WO | WO 97/10354 | 3/1997 |
| WO | WO 97/31108 | 8/1997 |
| WO | WO 97/32601 | 9/1997 |
| WO | WO 97/34632 | 9/1997 |
| WO | WO 98/22136 | 5/1998 |
| WO | WO 98/28331 | 7/1998 |
| WO | WO 98/44001 | 8/1998 |
| WO | WO 98/41641 | 9/1998 |
| WO | WO 98/42378 | 10/1998 |
| WO | WO 98/50431 | 11/1998 |
| WO | WO 99/02567 | 1/1999 |
| WO | WO 99/03495 | 1/1999 |
| WO | WO 99/10494 | 3/1999 |
| WO | WO 99/12973 | 3/1999 |
| WO | WO 99/17364 | 4/1999 |
| WO | WO 00/23593 | 4/2000 |
| WO | WO 00/44788 | 8/2000 |
| WO | WO 00/53634 | 9/2000 |
| WO | WO 00/67795 | 11/2000 |

(56) References Cited

FOREIGN PATENT DOCUMENTS

| WO | WO 00/69462 | 11/2000 |
|---|---|---|
| WO | WO 00/75191 | 12/2000 |
| WO | WO 01/36486 | 5/2001 |
| WO | WO 01/44282 | 6/2001 |
| WO | WO 01/64713 | 9/2001 |
| WO | WO 01/66737 | 9/2001 |
| WO | WO 01/70775 | 9/2001 |
| WO | WO 01/74388 | 10/2001 |
| WO | WO 01/77342 | 10/2001 |
| WO | WO 01/79494 | 10/2001 |
| WO | WO 01/87337 | 11/2001 |
| WO | WO 01/97858 | 12/2001 |
| WO | WO 02/04021 | 1/2002 |
| WO | WO 02/22212 | 3/2002 |
| WO | WO 02/28894 | 4/2002 |
| WO | WO 02/33072 | 4/2002 |
| WO | WO 02/33073 | 4/2002 |
| WO | WO 02/078612 | 10/2002 |
| WO | WO 02/094880 | 11/2002 |
| WO | WO 02/096457 | 12/2002 |
| WO | WO 02/097033 | 12/2002 |
| WO | WO 03/002607 | 1/2003 |
| WO | WO 03/033538 | 4/2003 |
| WO | WO 03/033654 | 4/2003 |
| WO | WO 03/057168 | 7/2003 |
| WO | WO 03/068260 | 8/2003 |
| WO | WO 03/086324 | 10/2003 |
| WO | WO 03/087163 | 10/2003 |
| WO | WO 03/097105 | 11/2003 |
| WO | WO 03/103723 | 12/2003 |
| WO | WO 03/104425 | 12/2003 |
| WO | WO 03/106974 | 12/2003 |
| WO | WO 03/107218 | 12/2003 |
| WO | WO 2004/003019 | 1/2004 |
| WO | WO 2004/019966 | 3/2004 |
| WO | WO 2004/026332 | 4/2004 |
| WO | WO 2004/033499 | 4/2004 |
| WO | WO 2004/037293 | 5/2004 |
| WO | WO 2004/081048 | 9/2004 |
| WO | WO 2004/087763 | 10/2004 |
| WO | WO 2004/111233 | 12/2004 |
| WO | WO 2005/004912 | 1/2005 |
| WO | WO 2005/044857 | 5/2005 |
| WO | WO 2005/056602 | 6/2005 |
| WO | WO 2005/056603 | 6/2005 |
| WO | WO 2005/056604 | 6/2005 |
| WO | WO 2005/056605 | 6/2005 |
| WO | WO 2005/056798 | 6/2005 |
| WO | WO 2005/100560 | 10/2005 |
| WO | WO 2005/107784 | 11/2005 |
| WO | WO 2006/101173 | 9/2006 |
| WO | WO 2006/123724 | 11/2006 |
| WO | WO 2008/007755 | 1/2008 |

OTHER PUBLICATIONS

Fish & Richardson P.C., Amendment in Reply to Action dated Nov. 3, 2009 in U.S. Appl. No. 11/913,229, filed Apr. 7, 2010, 15 pages.
Mallender et al., "Construction, expression and activity of a bivalent bispecific single-chain antibody," J. Biol. Chem., 269(1):199-206 (1994).
USPTO Restriction Requirement in U.S. Appl. No. 11/910,117, mailed May 3, 2010, 9 pages.
USPTO Final Office Action in U.S. Appl. No. 11/913,229, mailed Jun. 10, 2010, 10 pages.
USPTO Notice of Allowance in U.S. Appl. No. 10/551,504, mailed May 26, 2010, 7 pages.
Borden et al., "Lymphokines and Cytokines as Cancer Treatment," Cancer, 65:800-814 (1990).
Byers, "What Can Randomized Controlled Trials Tell us About Nutrition and Cancer Prevention?," CA Cancer J. Clin., 49:353-361 (1999).
USPTO Notice of Allowance in U.S. Appl. No. 10/551,504, mailed Jan. 7, 2010, 46 pages.
Fish & Richardson P.C., Amendment in Reply to Office Action dated Sep. 15, 2009 in U.S. Appl. No. 10/582,304, filed Jan. 13, 2010, 13 pages.
USPTO Non-Final Office Action in U.S. Appl. No. 11/913,229, mailed Nov. 3, 2009, 40 pages.
GenBank: U27005.1, *Mus musculus*, isolate 7183Liv, Vh7183 Ig heavy chain variable region gene, Vh region, partial cds, 1 page (Apr. 1996).
GenBank: AY081858.1, *Mus musculus*, isolate H3-9 anti-GBM immunoglobulin kappa chain variable region mRNA, partial cds, 1 page (Mar. 2004).
USPTO Notice of Allowance in U.S. Appl. No. 10/551,504, mailed Mar. 21, 2011, 7 pages.
Fish & Richardson P.C., Amendment in Reply to Action dated Dec. 9, 2010 in U.S. Appl. No. 10/582,304, filed May 27, 2011, 5 pages.
Fish & Richardson P.C., Amendment in Reply to Action dated Jan. 21, 2011 in U.S. Appl. No. 11/916,979, filed Jul. 14, 2011, 20 pages.
Fish & Richardson, Amendment in Reply to Action dated Jan. 7, 2011 in U.S. Appl. No. 10/530,696, filed Jun. 2, 2011, 5 pages.
USPTO Restriction Requirement in U.S. Appl. No. 10/582,176, mailed Oct. 19, 2009, 6 pages.
Fish & Richardson P.C., Response to Restriction Requirement dated Oct. 19, 2009 in U.S. Appl. No. 10/582,176, filed Nov. 4, 2009, 1 page.
USPTO Non-Final Office Action in U.S. Appl. No. 10/582,176, mailed Jan. 25, 2010, 7 pages.
Fish & Richardson P.C., Amendment in Reply to Action dated Jan. 25, 2010 in U.S. Appl. No. 10/582,176, filed Jul. 23, 2010, 11 pages.
USPTO Final Office Action in U.S. Appl. No. 10/582,176, mailed Oct. 29, 2010, 11 pages.
Fish & Richardson P.C., Amendment in Reply to Action dated Oct. 29, 2010 in U.S. Appl. No. 10/582,176, filed Apr. 28, 2011, 10 pages.
International Search Report for App. Ser. No. PCT/JP2004/018499, mailed Jan. 18, 2005, 2 pages.
International Preliminary Report on Patentability for App. Ser. No. PCT/JP2004/018499, dated Jan. 26, 2006, 5 pages.
USPTO Restriction Requirement in U.S. Appl. No. 10/582,413, mailed Jan. 4, 2008, 8 pages.
Fish & Richardson P.C., Response to Restriction Requirement dated Jan. 4, 2008 in U.S. Appl. No. 10/582,413, filed Feb. 4, 2008, 2 pages.
USPTO Non-Final Office Action in U.S. Appl. No. 10/582,413, mailed Mar. 31, 2008, 17 pages.
Fish & Richardson P.C., Amendment in Reply to Action dated Mar. 31, 2008 in U.S. Appl. No. 10/582,413, filed Jun. 30, 2008, 20 pages.
USPTO Interview Summary in U.S. Appl. No. 10/582,413, mailed Jun. 30, 2008, 2 pages.
USPTO Notice of Informal or Non-Responsive Amendment in U.S. Appl. No. 10/582,413, mailed Oct. 20, 2008, 3 pages.
USPTO Interview Summary in U.S. Appl. No. 10/582,413, mailed Nov. 12, 2008, 4 pages.
Fish & Richardson P.C., Amendment in Reply to Notice of Informal or Non-Responsive Amendment dated Oct. 20, 2008 in U.S. Appl. No. 10/582,413, filed Nov. 17, 2008, 10 pages.
USPTO Interview Summary in U.S. Appl. No. 10/582,413, mailed Nov. 25, 2008, 4 pages.
USPTO Interview Summary in U.S. Appl. No. 10/582,413, mailed Dec. 24, 2008, 4 pages.
USPTO Restriction Requirement in U.S. Appl. No. 10/582,413, mailed Mar. 11, 2009, 8 pages.
Fish & Richardson P.C., Response to Restriction Requirement dated Mar. 11, 2009 in U.S. Appl. No. 10/582,413, filed Apr. 8, 2009, 8 pages.
USPTO Final Office Action in U.S. Appl. No. 10/582,413, mailed Jun. 25, 2009, 28 pages.
USPTO Interview Summary in U.S. Appl. No. 10/582,413, mailed Oct. 27, 2009, 4 pages.
USPTO Interview Summary in U.S. Appl. No. 10/582,413, mailed Dec. 2, 2009, 4 pages.
USPTO Non-Final Office Action in U.S. Appl. No. 10/582,413, mailed Apr. 16, 2010, 27 pages.
Fish & Richardson P.C., Amendment in Reply to Action dated Apr. 16, 2010 in U.S. Appl. No. 10/582,413, filed Oct. 15, 2010, 11 pages.

(56) References Cited

OTHER PUBLICATIONS

USPTO Final Office Action in U.S. Appl. No. 10/582,413, mailed Dec. 23, 2010, 12 pages.
International Search Report for App. Ser. No. PCT/JP2004/018493, mailed Mar. 22, 2005, 2 pages.
International Preliminary Report on Patentability for App. Ser. No. PCT/JP2004/018493, dated Dec. 20, 2005, 7 pages.
European Search Report for App. Ser. No. EP 04 82 0305, dated Oct. 6, 2008, 3 pages.
Fish & Richardson P.C., Amendment and Response to Restriction Requirement mailed May 3, 2010 in U.S. Appl. No. 11/910,117, filed Nov. 2, 2010, 11 pages.
USPTO Non-Final Office Action in U.S. Appl. No. 11/910,117, mailed Jan. 24, 2011, 10 pages.
Fish & Richardson P.C., Amendment in Reply to Action dated Jan. 24, 2011 in U.S. Appl. No. 11/910,117, filed Jun. 23, 2011, 20 pages.
Fish & Richardson P.C., Amendment in Reply to Action dated Mar. 3, 2011 in U.S. Appl. No. 11/916,351, filed Aug. 2, 2011, 17 pages.
USPTO Non-Final Office Action in U.S. Appl. No. 10/582,304, mailed Aug. 15, 2011, 10 pages.
USPTO Notice of Allowability in U.S. Appl. No. 10/530,696, mailed Aug. 15, 2011, 3 pages.
Alexander et al., "Studies of the c-Mpl Thrombopoietin Receptor through Gene Disruption and Activation," *Stem Cells*, 14(suppl 1):124-132 (1996).
Andris-Widhopf et al., "Methods for the generation of chicken monoclonal antibody fragments by phage display," *Journal of Immunological Methods*, 242:159-181 (2000).
Arndt et al., "Factors Influencing the Dimer to Monomer Transition of an Antibody Single-Chain Fv Fragment," *Biochemistry*, 37:12918-12926 (1998).
Arndt et al., "Generation of a highly stable, internalizing anti-DC22 single-chain Fv fragment for targeting non-Hodgkin's lymphoma," *Int. J. Cancer*, 107(5):822-829 (2003).
Avent et al., "Monoclonal antibodies that recognize different membrane proteins that are deficient in Rhnull human erythrocytes. One group of antibodies reacts with a variety of cells and tissues whereas the other group is erythroid-specific," *Biochem. J.*, 251:499-505 (1988).
Ballmaier et al., "c-mpl mutations are the cause of congenital amegakaryocytic thrombocytopenia," *Blood*, 97:139-146 (2001).
Bartley et al., "Identification and Cloning of a Megakaryocyte Growth and Development Factor That is a Ligand for the Cytokine Receptor Mpl," *Cell*, 77:1117-1124 (1994).
Bazil et al., "Apoptosis of human hematopoietic progenitor cells induced by crosslinking of surface CD43, the major sialoglycoprotein of leukocytes," *Blood*, 86:502-511 (1995).
Bazzoni et al., "Chimeric tumor necrosis factor receptors with constitutive signaling activity," *Proc. Natl. Acad. Sci. USA*, 92(12):5376-5580 (1995).
Berger et al., "Inhibition of intractable nucleases with ribonucleoside-vanadyl complexes: isolation of messenger ribonucleic acid from resting lymphocytes," *Biochemistry*, 18(23):5143-5149 (1979).
Bodmer et al., "TRAIL Receptor-2 Signals Apoptosis Through FADD and Caspase-8," *Nat. Cell Biol.*, 2:241-243 (2000).
Boger et al., "Cytokine receptor dimerization and activation: prospects for small molecule agonists," *Bioorganic and Medicinal Chemistry*, 9(3):557-562 (2001).
Brinkmann et al., "FTY720: targeting G-protein-coupled receptors for sphingosine 1-phosphate in transplantation and autoimmunity," *Curr. Opin. Immunol.*, 14:569-575 (2002).
Brooke et al., "Human lymphocytes interact directly with CD47 through a novel member of the signal regulatory protein (SIRP) family," *J. Immunol.*, 173:2562-2570 (2004).
Brown et al., "Integrin-associated protein (CD47) and its ligands," *Trends Cell Biology*, 11(3):130-135 (2001).
Brown et al., "Integrin-associated protein: a 50-kD plasma membrane antigen physically and functionally associated with integrins," *J. Cell Biology*, 111(6 Pt 1):2785-2794 (1990).
Bruenke et al., "A recombinant bispecific single-chain Fv antibody against HLA class II and FcγRIII (CD16) triggers effective lysis of lymphoma cells," *Br. J. Haematol.*, 125:167-179 (2004).
Buchsbaum et al., "Antitumor Efficacy of TRA-8 Anti-DR5 Monoclonal Antibody Alone or in Combination with Chemotherapy and/or Radiation Therapy in a Human Breast Cancer Model," *Clin. Cancer Res.*, 9:3731-3741 (2003).
Burgess et al., "Possible dissociation of the heparin-binding and mitogenic activities of heparin-binding (acidic fibroblast) growth factor-1 from its receptor-binding activities by site-directed mutagenesis of a single lysine residue," *J. Cell Biol.*, 111:2129-2138 (1990).
Burrone et al., "Stimulation of HLA-A,B,C by IFN-alpha. The derivation of Molt 4 variants and the differential expression of HLA-A,B,C subsets," *The EMBO Journal*, 4(11):2855-2860 (1985).
Burthem et al., "Hairy cell interactions with extracellular matrix: expression of specific integrin receptors and their role in the cell's response to specific adhesive proteins," *Blood*, 84(3):873-882 (1994).
Caldas et al., "Humanization of the anti-CD18 antibody 6.7: an unexpected effect of a framework residue in binding to antigen," *Mol. Immunol.*, 39:941-952 (2003).
Cangemi et al., "IFN-alpha mediates the up-regulation of HLA class I on melanoma cells without switching proteasome to immunoproteasome," *International Immunology*, 15(12):1415-1421 (2005).
CAPLUS Accession No. 2005:547624, 2 pages (2008).
Caron et al., "Engineered Humanized Dimeric Forms of IgG Are More Effective Antibodies," *J. Exp. Med.*, 176:1191-1195 (1992).
Carter, "Bispecific human IgG by design," *J. Immunol. Methods*, 248:7-15 (2001).
Cekaite et al., "Protein Arrays: A versatile toolbox for target identification and monitoring of patient immune responses," *Methods Mol. Biol.*, 360:335-348 (2007).
Chatellier et al., "Functional mapping of conserved residues located at the VL and VH domain interface of a Fab," *J. Mol. Biol.*, 264(1):1-6 (1996).
Chien et al., "Significant structural and functional change of an antigen-binding site by a distant amino acid substitution: Proposal of a structural mechanism," *Proc. Nat. Acad. Sci. USA*, 86:5532-5536 (1989).
Chirgwin et al., "Isolation of biologically active ribonucleic acid from sources enriched in ribonuclease," *Biochemistry*, 18(24):5294-5299 (1979).
Chowdhury et al., "Engineering scFvs for improved stability," *Methods Mol. Biol.*, 207:237-54 (2003).
Chuntharapai et al. "Isotype-Dependent Inhibition of Tumor Growth In Vivo by Monoclonal Antibodies to Death Receptor 4," *J. Immunol.*, 166:4891-4898 (2001).
Clackson et al., "Making antibody fragments using phage display libraries," *Nature*, 352:624-628 (1991).
Clark, "CD22, a B Cell-Specific Receptor, Mediates Adhesion and Signal Transduction," *J. Immunol.*, 150:4715-4718 (1993).
Co et al., "A Humanized Antibody Specific for the Platelet Integrin gpIIb/IIIa," *J. Immunol.*, 152:2968-2976 (1994).
Cochlovius et al., "Cure of Burkitt's Lymphoma in Severe Combined Immunodeficiency Mice by T Cells, Tetravalent CD3×CD19 Tandem Diabody and CD28 Costimulation," *Cancer Res.*, 60:4336-4341 (2000).
Cochlovius et al., "Treatment of human B cell lymphoma xenografts with a CD3×CD19 diabody and T cells," *The Journal of Immunology*, 165:888-895 (2000).
Cooper et al., "Transendothelial migration of neutrophils involves integrin-associated protein (CD47)," *Proc. Natl. Acad. Sci. USA*, 92:3978-3982 (1995).
Daniel et al., "Induction of Apoptosis in Human Lymphocytes by Human Anti-HLA Class I Antibodies," *Transplantation*, 75:1380-1386 (2003).
Davies et al., "Antibody VH domains as small recognition units," *Biotechnology* (N.Y.), 13(5):475-9 (1995).
De Felice et al., "Differential regulatory role of monomorphic and polymorphic determinants of histocompatibility leukocyte antigen

(56) References Cited

OTHER PUBLICATIONS class I antigens in monoclonal antibody OKT3-induced T cell proliferation," *J. Immunol.*, 139:2683-2689 (1987).
De Jonge et al., "Production and Characterization of Bispecific Single-Chain Antibody Fragments," *Mol. Immunol.*, 32:1405-1412 (1995).
De Leon et al., "High resolution human leukocyte antigen (HLA) class I and class II allele typing in Mexican mestizo women with sporadic breast cancer: case-control study," *BMC Cancer*, 9(48):1-9 (2009).
De Pascalis et al., "Grafting of 'abbreviated' complementary-determining regions containing specificity-determining residues essential for ligand contact to engineer a less immunogenic humanized monoclonal antibody," *Journal of Immunology*, 169:3076-3084 (2002).
De Sauvage et al., "Stimulation of Megakaryocytopoiesis and Thrombopoiesis by the c-Mpl Ligand," *Nature*, 369:533-538 (1994).
De St. Groth et al., "Production of Monoclonal Antibodies: Strategy and Tactics," *Journal of Immunological Methods*, 35:1-21 (1980).
Degli-Esposti et al., "Cloning and Characterization of TRAIL-R3, a Novel Member of the Emerging TRAIL Receptor Family," *J. Exp. Med.*, 186:1165-1170 (1997).
Denardo et al., "Anti-HLA-DR/anti-DOTA Diabody Construction in a Modular Gene Design Platform: Bispecific Antibodies for Pretargeted Radioimmunotherapy," *Cancer Biother. Radiopharm.*, 16:525-535 (2001).
Desplancq et al., "Multimerization behaviour of single chain Fv variants for the tumour-binding antibody B72.3," *Protein Engineering*, 7(8):1027-1033 (1994).
Dillman, "Monoclonal antibodies for treating cancer," *Ann. Int. Med.*, 11(7):592-603 (1989).
Dorai et al., "Mammalian cell expression of single-chain Fv (sFv) antibody proteins and their C-terminal fusions with interleukin-2 and other effector domains," *Biotechnology*, 12(9):890-897 (1994).
Dufner et al., "Harnessing phage and ribosome display for antibody optimization," *Trends Biotechnol.*, 24(11):523-529 (2006).
Ebert et al., "Expression of Metallothionein II in Intestinal Metaplasia, Dysplasia, and Gastric Cancer," *Cancer Res.*, 60:1995-2001 (2000).
Eijsink et al., "Rational engineering of enzyme stability," *Journal of Biotechnology*, 113:105-120 (2004).
EMBL Accession No. AY081858, dated Jan. 2, 2003, 1 page.
EMBL Accession No. U27005, dated Aug. 31, 1995, 1 page.
Emery et al., "Osteoprotegerin Is a Receptor for the Cytotoxic Ligand TRAIL," *J. Biol. Chem.*, 273:14363-14367 (1998).
Ewert et al., "Biophysical properties of human antibody variable domains," *J. Mol. Biol.*, 325:531-553 (2003).
Ewert et al., "Stability improvement of antibodies for extracellular and intracellular applications: CDR grafting to stable frameworks and structure-based framework engineering," *Methods*, 34:184-199 (2004).
Ewert et al., "Structure-based improvement of the biophysical properties of immunoglobulin $V_H$ domains with a generalizable approach," *Biochemistry*, 42:1517-1528 (2003).
Fayen et al., "Negative signaling by anti-HLA class I antibodies is dependent upon two triggering events," *Int. Immunol.*, 10:1347-1358 (1998).
Felgenhauer et al. "Nucleotide Sequences of the cDNAs Encoding the V-Regions of H- and L-Chains of a Human Monoclonal Antibody Specific to HIV-1—gp41," *Nucleic Acids Research*, 18(16):4927 (1990).
Fisk et al., "Increased sensitivity of Adriamycin-selected Tumor Lines to CTL-mediated Lysis Results in Enhanced Drug Sensitivity," *Cancer Res.*, 58:4790-4793 (1998).
Fox et al., "Thrombopoietin expands hematopoietic stem cells after transplantation," *J. Clin. Invest.*, 110(3):389-394 (2002).
Fujimoto et al., "50-kD integrin-associated protein does not detectably influence several functions of glycoprotein IIb-IIIa complex in human platelets," *Blood*, 86(6):2174-2182 (1995).

Fukushima et al., "Apoptosis of Bone Marrow Cells Via Integrin Associated Protein by the Novel Monoclonal Antibody," *Blood*, 94(10):479A (1999).
Fukushima et al., "Enhanced hematopoiesis in vivo and in vitro by splenic stromal cells derived from the mouse with recombinant granulocyte colony-stimulating factor," *Blood*, 80(8):1914-1922 (1992).
Funaro et al., "Monoclonal antibodies and therapy of human cancers," *Biotechnol. Adv.*, 18:385-401 (2000).
Galfre et al., "Preparation of monoclonal antibodies: strategies and procedures," *Methods in Enymology*, 73:3-46 (1981).
Galfre et al., "Rat x rat hybrid myelomas and a monoclonal anti-Fd portion of mouse IgG," *Nature*, 277:131-133 (1979).
Genestier et al., "Caspase-dependent Ceramide Production in Fas- and HLA Class I-mediated Peripheral T Cell Apoptosis," *J. Biol. Chem.*, 273:5060-5066 (1998).
Genestier et al., "Antibodies to HLA Class 1 α1 Domain Trigger Apoptosis of CD40-Activated Human B Lymphocytes," *Blood*, 90:726-735 (1997).
Genestier et al., "Fas-Independent Apoptosis of Activated T Cells Induced by Antibodies to the HLA Class I α1 Domain," *Blood*, 90:3629-3639 (1997).
Genestier et al., "T cell sensitivity to HLA class I-mediated apoptosis is dependent on interleukin-2 and interleukin-4," *Eur. J. Immunol.*, 27:495-499 (1997).
Ghetie et al., "Homodimerization of tumor-reactive monoclonal antibodies markedly increases their ability to induce growth arrest or apoptosis of tumor cells," *Proc. Natl. Acad. Sci. USA*, 94:7509-7514 (1997).
Giusti et al., "Somatic diversification of S107 from an antiphosphocholine to an anti-DNA autoantibody is due to a single base change in its heavy chain variable region," *Proc. Natl. Acad. Sci. USA*, 84:2926-2930 (1987).
Goding, "Monoclonal Antibodies: Principles and Practice," *Academic Press*, second Ed., 125:129 (1986).
Goel et al., "$^{99m}$Tc-Labeled Divalent and Tetravalent CC49 Single-Chain Fv's: Novel Imaging Agents for Rapid In Vivo Localization of Human Colon Carcinoma," *J. Nucl. Med.*, 42:1519-1527 (2001).
Goel et al., "Genetically Engineered Tetravalent Single-Chain Fv of the Pancarcinoma Monoclonal Antibody CC49: Improved Biodistribution and Potential for Therapeutic Application," *Cancer Res.*, 60:6964-6971 (2000).
Goldstein et al., "Cytolytic and Cytostatic Properties of an Anti-Human FcγRI (CD64) x Epidermal Growth Factor Bispecific Fusion Protein," *J. Immunol.*, 158:872-879 (1997).
Goto et al., "A Novel Membrane Antigen Selectively Expressed on Terminally Differentiated Human B Cells," *Blood*, 84:1922-1930 (1994).
Granziero et al., "Adoptive immunotherapy prevents prostate cancer in a transgenic animal model," *Eur. J. Immunol.*, 29:1127-1138 (1999).
Greenspan et al., "Defining epitopes: It's not as easy as it seems," *Nature Biotechnology*, 17:936-937 (1999).
Grell et al., "TR60 and TR80 tumor necrosis factor (TNF)-receptors can independently mediate cytolysis," *Lymphokine and Cytokine Research*, 12(3):143-148 (1993).
Griffith et al., "Functional Analysis of TRAIL Receptors Using Monoclonal Antibodies," *J. Immunol.*, 162:2597-2605 (1999).
Gruber et al., "Efficient tumor cell lysis mediated by a bispecific single chain antibody expressed in *Escherichia coli*," *Journal of Immunology*, 152:5368-5374 (1994).
Güssow and Seemann, "Humanization of Monoclonal Antibodies," *Methods in Enzymology*, 203:99-121 (1991).
Higa et al., "Administration of anti-interleukin 18 antibody fails to inhibit development of dermatitis in atopic dermatitis-model mice NC/Nga," *Br. J. Dermatol.*, 149(1):39-45 (2003).
Holliger el at., "Specific Killing of Lymphoma Cells by Cytotoxic T-Cells Mediated by a Bispecific Diabody," *Protein Engineering*, 9(3):299-305 (1996).
Holliger et al., "'Diabodies': Small bivalent and bispecific antibody fragments," *Proc. Natl. Acad. Sci. USA*, 90:6444-6448 (1993).

(56) References Cited

OTHER PUBLICATIONS

Holm et al., "Functional mapping and single chain construction of the anti-cytokeratin 8 monoclonal antibody TS1," *Molecular Immunology*, 44:1075-1084 (2007).
Hoogenboom et al., "Multi-subunit proteins on the surface of filamentous phage: methodologies for displaying antibody (Fab) heavy and light chains," *Nucleic Acids Res.*, 19:4133-4137 (1991).
Hopp et al., "A Short Polypeptide Marker Sequence Useful for Recombinant Protein Identification and Purification," *Biotechnology*, 6:1204-1210 (1988).
Horan et al., "Dimerization of the extracellular domain of granuloycte-colony stimulating factor receptor by ligand binding: a monovalent ligand induces 2:2 complexes," *Biochemistry*, 35:4886-4896 (1996).
Hozumi and Tonegawa, "Evidence for somatic rearrangement of immunoglobulin genes coding for variable and constant regions," *Proc. Natl. Acad. Sci. USA*, 73(10):3628-3632 (1976).
Hu et al., "Minibody: A Novel Engineered Anti-Carcinoembryonic Antigen Antibody Fragment (Single-Chain Fv-$C_H3$) Which Exhibits Rapid, High-Level Targeting of Xenografts," *Cancer Res.*, 56:3055-3061 (1996).
Hudson et al., "High avidity scFv multimers; diabodies and triabodies," *J. Immunol. Methods*, 231:177-189 (1999).
Huston et al., "Protein Engineering of Antibody Binding Sites: Recovery of Specific Activity in an Anti-Digoxin Single-Chain Fv Analogue Produced in *Escherichia coli*," *Proc. Natl. Acad. Sci. USA*, 85:5879-5883 (1988).
Ichikawa et al., "Tumoricidal activity of a novel anti-human DR5 monoclonal antibody without hepatocyte cytotoxicity," *Nat. Med.*, 7:954-960 (2001).
Itoh et al., "The Polypeptide Encoded by the cDNA for Human Cell Surface Antigen Fas Can Mediate Apoptosis," *Cell*, 66:233-243 (1991).
Jäger et al., "Folding and assembly of an antibody Fv fragment, a heterodimer stabilized by antigen," *Journal of Molecular Biology*, 285:2005-2019 (1999).
Jalili et al., "Multi-Drug Resistant Leukemic Cells Highly Express HLA Class I Molecules and Single-Chain Fv Diabody Specific to HLA-A Overcomes Drug Resistance in These Cells," *Blood (ASH Annual Meeting Abstracts)*, 118(11):701a-702a (#2376) (2007).
Jiang et al., "A Novel Peptide Isolated from a Phage Display Peptide Library with Trastuzumab Can Mimic Antigen Epitope of HER-2," *J. Biol. Chem.*, 280(6):4656-4662 (2005).
Jones et al., "Rapid PCR-Cloning of Full-Length Mouse Immunoglobulin Variable Regions," *Biotechnology*, 9:88-89 (1991).
Jung et al., "The importance of framework residues H6, H7 and H10 in antibody heavy chains: experimental evidence for a new structural subclassification of antibody V(H) domains," *J. Mol. Biol.*, 309(3):701-16 (2001).
Kaushansky, "Lineage-specific hematopoietic growth factors," *N. Engl. J. Med.*, 354(19):2034-45 (2006).
Kearney, et al., "A New Mouse Myeloma Cell Line That Has Lost immunoglobulin Expression But Permits the Construction of Antibody-Secreting Hybrid Cells Lines," *The Journal of Immunology*, 123(4):1548-1550 (1979).
Keen et al., "The use of serum-free medium for the production of functionally active humanized monoclonal antibody from NSO mouse myeloma cells engineered using glutamine synthetase as a selectable marker," *Cytotechnology*, 18(3):207-217 (Abstract) (1994).
Khalifa et al., "Effects on interaction kinetics of mutations at the VH-VL interface of Fabs depend on the structural context," *J. Mol. Recognit.*, 13(3):127-39 (2000).
Kikuchi et al., "A bivalent single-chain Fv fragment against CD47 induces apoptosis for leukemic cells," *Biochem. Biophys. Res. Commun.*, 315:912-918 (2004).
Kimura et al., "2D7 diabody bound to the α2 domain of HLA class I efficiently induces caspase-independent cell death against malignant and activated lymphoid cells," *Biochem. Biophys. Res. Commun.*, 325:1201-1209 (2004).

Kipriyanov and Little, "Generation of Recombinant Antibodies," *Molecular Biotechnology*, 12:173-201 (1999).
Kipriyanov et al., "Bispecific tandem diabody for tumor therapy with improved antigen binding and pharmacokinetics," *Journal of Molecular Biology*, 293:41-56 (1999).
Kipriyanov et al., "Effect of Domain Order on the Activity of Bacterially Produced Bispecific Single-chain Fv Antibodies," *J. Mol. Biol.*, 330:99-111 (2003).
Kohler, et al., "Derivation of specific antibody-producing tissue culture and tumor lines by cell fusion," *Eur. J. Immunol.*, 6:511-519 (1976).
Kong et al., "A Single Residue, Aspartic Acid 95, in the δ Opioid Receptor Specifies Selective High Affinity Agonist Binding," *The Journal of Biological Chemistry*, 268(31):23056-23058 (1993).
Korn et al., "Recombinant bispecific antibodies for the targeting of adenoviruses to CEA-expressing tumour cells: a comparative analysis of bacterially expressed single-chain diabody and tandem scFv," *The Journal of Gene Medicine*, 6:642-651 (2004).
Kortt et al., "Dimeric and trimeric antibodies: high avidity scFvs for cancer targeting," *Biomol. Eng.*, 18:95-108 (2001).
Kortt et al., "Recombinant anti-sialidase single-chain variable fragment antibody: Characterization, formation of dimmer and higher-molecular-mass multimers and the solution of the crystal structure of the single-chain variable fragment/sialidase complex," *Eur. J. Biochem.*, 221:151-157 (1994).
Kortt et al., "Single-chain Fv fragments of anti-neuraminidase antibody NC10 containing five- and ten-residue linkers form dimmers and with zero-residue linker a trimer," *Protein Engineering*, 10(4):423-433 (1997).
Kozak, M., "At Least Six Nucleotides Preceding the AUG Initiator Codon Enhance Translation in Mammalian Cells," *J. Mol. Biol.*, 196:947-950 (1987).
Krebber et al., "Reliable cloning of functional antibody variable domains from hybridomas and spleen cell repertoires employing a reengineered phage display system," *J. Immunol. Methods*, 201:35-55 (1997).
Kreitman et al., "Cytotoxic Activity of Disulfide-stabilized Recombinant Immunotoxin RFB4(dsFv)-PE38 (BL22) toward Fresh Malignant Cells from Patients with B-Cell Leukemias," *Clin. Cancer Res.*, 6:1476-1487 (2000).
Kriangkum et al., "Bispecific and bifunctional single chain recombinant antibodies," *Biomol. Eng.*, 18(2):31-40 (2001).
Kulkarni et al., "Construction of a Single-Chain Antibody Derived From 5H7, A Monoclonal Antibody Specific for a Death Signaling Domain of Human Class I Major Histocompatibility Complex," *Transplant. Proc.*, 30:1081 (1998).
Kulkarni et al., "Programmed Cell Death Signaling Via Cell-Surface Expression of a Single-Chain Antibody Transgene," *Transplantation*, 69:1209-1217 (2000).
Kumar et al., "Molecular cloning and expression of the fabs of human autoantibodies in *Escherichia coli*," *The Journal of Biological Chemistry*, 275(41):35129-35136 (2000).
Kumar et al., "The second PDZ domain of INAD is a type I domain involved in binding to eye protein kinase C. Mutational analysis and naturally occurring variants," *J. Biol. Chem.*, 276(27):24971-24977 (2001).
Kurucz et al., "Retargeting of CTL by an efficiently refolded bispecific single-chain Fv dimer produced in bacteria," *The Journal of Immunology*, 154:4576-4582 (1995).
Larrick, et al., "Polymerase Chain Reaction Using Mixed Primers: Cloning of Human Monoclonal Antibody Variable Region Genes From Single Hybridoma Cells," *Biotechnology*, 7:934-938 (1989).
Law et al., "Observations on the Effect of a Folic-Acid Antagonist on Transplantable Lymphoid Leukemias in Mice," *Journal of the National Cancer Institute*, 10:179-193 (1949).
Lazar et al., "Transforming growth factor a: mutation of aspartic acid 47 and leucine 48 results in different biological activities," *Molecular and Cellular Biology*, 8:1247-1252 (1988).
Lebrun et al., "Antibodies to the Extracellular Receptor Domain Restore the Hormone-insensitive Kinase and Conformation of the Mutant Insulin Receptor Valine 382," *J. Biol. Chem.*, 268:11272-11277 (1993).

(56) References Cited

OTHER PUBLICATIONS

Ledbetter et al., "Agonistic Activity of a CD40-Specific Single-Chain Fv Constructed from the Variable Regions of mAb G28-5," *Critical Reviews in Immunology*, 17:427-435 (1997).
Lei et al., "Characterization of the *Erwinia carotovora pelB* Gene and Its Product Pectate Lyase," *Journal of Bacteriology*, 169:4379-4383 (1987).
Li et al., "The Epitope Specificity and Tissue Reactivity of Four Murine Monoclonal Anti-CD22 Antibodies," *Cell. Immunol.*, 118:85-99 (1989).
Lindberg et al., "Molecular Cloning of Integrin-Associated Protein: An Immunoglobulin Family Member with Multiple Membrane-Spanning Domains Implicated in $\alpha_v\beta_3$-Dependent Ligand Binding," *The Journal of Cell Biology*, 123(2):485-496, The Rockefeller University Press (1993).
Lindberg et al., "Rh-Related Antigen CD47 is the Signal-Transducer Integrin-Associated Protein," *J. Biol. Chem.*, 269:1567-1570 (1994).
Little et al., "Of mice and men: hybridoma and recombinant antibodies," *Immunol. Today*, 21:364-370 (2000).
Liu et al., "Functional interactions between arginine-133 and aspartate-88 in the human reduced folate carrier: evidence for a charge-pair association," *Biochem. J.*, 358:511-516 (2001).
Loffler, "A recombinant bispecific single-chain antibody, CD19×CD3, induces rapid and high lymphoma-directed cytotoxicity by unstimulated T lymphocytes," *Blood*, 95(6):2098-2103 (2000).
Maccallum et al., "Antibody-antigen independent interactions: contact analysis and binding site topography," *Journal of Molecular Biology*, 262:732-745 (1996).
Mack et al., "A small bispecific antibody construct expressed as a functional single-chain molecule with high tumor cell cytotoxicity," *Proc. Natl. Acad. Sci. USA*, 92(15):7021-7025 (1995).
Maity et al., "Equilibrium unfolding of dimeric and engineered monomeric forms of Cro (F58W) repressor and the effect of added salts: evidence for the formation of folded monomer induced by sodium perchlorate," *Archives of Biochemistry and Biophysics*, 434:93-107 (2005).
Margulies et al., "Somatic Cell Hybridization of Mouse Myeloma Cells," *Cell*, 8:405-415 (1976).
Mariuzza et al., "The Structural Basis of Antigen-Antibody Recognition," *Ann. Rev. Biophys. Biophys. Chem.*, 16:139-159 (1987).
Marsters et al., "A Novel Receptor for Apo2L/TRAIL Contains a Truncated Death Domain," *Curr. Biol.*, 7:1003-1006 (1997).
Mateo et al., "CD47 ligation induces caspase-independent cell death in chronic lymphocytic leukemia," *Nat. Med.*, 5(11):1277-1284 (1999).
Mateo et at al., "Induction of Apoptosis in B-Cells From Chronic Lymphocytic Leukemia (B-CLLs) by CD47," *FASEB Journal*, 12(5):A1082 (1998).
Matsuoka et al., "A Monoclonal Antibody to the $\alpha 2$ Domain of Murine Major Histocompatibility Complex Class I that Specifically Kills Activated Lymphocytes and Blocks Liver Damage in the Concanavalin A Hepatitis Model," *J. Exp. Med.*, 198:497-503 (2003).
Matsuoka et al., "A Novel Type of Cell Death of Lymphocytes Induced by a Monoclonal Antibody without Participation of Complement," *J. Exp. Med.*, 181:2007-2015 (1995).
Mawby et al., "Isolation and characterization of CD47 glycoprotein: a multispanning membrane protein which is the same as integrin-associated protein (IAP) and the ovarian tumor marker OA3," *Biochem. J.*, 304:525-530 (1994).
McGuinness et al., "Phage diabody repertoires for selection of large number of bispecific antibody fragments," *Nature Biotechnology*, 14(9):1149-1154 (1996).
McInnes and Schett, "Cytokines in the pathogenesis of rheumatoid arthritis," *Nature Reviews/Immunology*, 7:429-442 (2007).
Medline Plus Drug Information: Dexamethasone Oral www.nlm.nih.gov/medlineplus/druginfo/meddmaster/a682792.html, downloaded Jul. 19, 2007; last revised Apr. 1, 2003 (see p. 3) (4 pages).
Melguizo et al., "Modulation of HLA class I expression in multidrug-resistant human rhabdomyosarcoma cells," *Neoplasma*, 50(2):91-96 (2003).
Meng et al., "The evaluation of recombinant, chimeric, tetravalent antihuman CD22 antibodies," *Clinical Cancer Research*, 10:1274-1281 (2004).
Merchant et al., "An efficient route to human bispecific IgG," *Nature Biotechnology*, 16:677-681 (1996).
Methia et al., "Oligodeoxynucleotides Antisense to the Proto-Oncogene c-Mpl Specifically Inhibit In Vitro Megakaryocytopoiesis," *Blood*, 82(5):1395-1401 (1993).
Milili et al., "The VDJ Repertoire Expressed in Human preB Cells Reflects the Selection of *Bona Fide* Heavy Chains," *Eur. J. Immunol.*, 26:63-69 (1996).
Milligan, "G Protein-Coupled Receptor Dimerization: Function and Ligand Pharmacology," *Mol. Pharm.*, 66:1-7 (2004).
Miyazaki et al., "Future Prospects of Thrombopoietin," *Jpn. J. Transfusion Medicine*, 46(3):311-316 (2000) [English translation included].
Mizushima et al., "pEF-BOS, a Powerful Mammalian Expression Vector," *Nucleic Acids Research*, 18(17):5322 (1990).
Moore et al., "Kinetics and thermodynamics of dimer formation and dissociation for a recombinant humanized monoclonal antibody to vascular endothelial growth factor," *Biochemistry*, 38:13960-13967 (1999).
Mori et al., "Human normal hepatocytes are susceptible to apoptosis signal mediated by both TRAIL-R1 and TRAIL-R2," *Cell Death and Differentiation*, 11:203-207 (2004).
Mulligan et al., "Synthesis of Rabbit $\beta$-Globin in Cultured Monkey Kidney Cells Following Infection with a SV40 $\beta$-Globin Recombinant Genome," *Nature*, 277:108-114 (1979).
Nakamura et al., "A novel non-peptidyl human c-Mpl activator stimulates human megakaryopoiesis and thrombopoiesis," *Blood*, 107(11):4300-4307 (2006). Epub DOI 10.1182/blood-2005-11-4433 (2006).
Nakamura et al., "A Novel Non-Peptidyl Human C-Mpl Agonist, NIP-004, Stimulates Human Megakaryopoiesis and Thrombopoiesis," *Blood* (*ASH Annual Meeting Abstracts*), Abstract 3148 (2005).
Nagayama et al., "Transient hematopoietic stem cell rescue using umbilical cord blood for a lethally irradiated nuclear accident victim," *Bone Marrow Transplant.* 29(3):197-204 (2002).
Nakayama et al., "Thrombocytosis in preterm infants: a possible involvement of thrombopoietin receptor gene expression," *Journal of Molecular Medicine*, 83:316-320 (2005).
Nieba et al., "Disrupting the hydrophobic patches at the antibody variable/constant domain interface: improved in vivo folding and physical characterization of an engineered scFv fragment," *Protein Engineering*, 10(4):435-444 (1997).
Nishii, "CD22 antibody therapy," *Current Therapy*, 20:47-50 (2001) (English translation included).
Nohaile et al., "Altering dimerization specificity by changes in surface electrostatics," *PNAS* 98(6):3109-3114 (2001).
O'Brien et al., "Monoclonal antibodies for the human insulin receptor stimulate intrinsic receptor-kinase activity," *Biochim. Soc. Trans.*, 14(6):1021-1023 (1986).
Ohtomo et al., "Molecular Cloning and Characterization of a Surface Antigen Preferentially Overexpressed on Multiple Myeloma Cells," *Biochem. Biophys. Res. Commun.*, 258:583-591 (1999).
Ohtsuka et al., "Synergistic induction of tumor cell apoptosis by death receptor antibody and chemotherapy agent through JNK/p38 and mitochondrial death pathway," *Oncogene*, 22:2034-2044 (2003).
Oka, "Development of Novel Immunotoxin Using Recombinant Alpha-Sarcin and Its Application Treatment of Hematopoietic Tumor," *Sankyo Seimei Kagaku Kenkyu Shinko Zaidan Kenkyu Hokokushu*, 12:46-56 (1998) (English translation included).
Ono et al., "The humanized anti-HM1.24 antibody effectively kills multiple myeloma cells by human effector cell-mediated cyto-toxicity," *Mol. Immunol.*, 36:387-395 (1999).
Orita et al., "A novel therapeutic approach for thrombocytopenia by minibody agonist of the thrombopoietin receptor," *Blood*, 105:562-566 (2005).
Ozaki et al., "A recombinant HLA class I-specific single chain Fv diabody induces cell death in human lymphoid malignancies," *45th Annual Meeting of the American Society of Hematology*, San Diego, CA, USA (Dec. 6-9, 2003).

(56) References Cited

OTHER PUBLICATIONS

Ozaki et al., "A Recombinant HLA Class I-Specific Single Chain Fv Diabody Induces Cell Death in Human Lymphoid Malignancies," *Blood*, 102:933a, Abstract No. 3474 (2003).
Ozaki et al., "Humanized Anti-HM1.24 Antibody Mediates Myeloma Cell Cytotoxicity That Is Enhanced by Cytokine Stimulation of Effector Cells," *Blood*, 93:3922-3930 (1999).
Ozaki et al., "Immunotherapy of Multiple Myeloma With a Monoclonal Antibody Directed Against a Plasma Cell-Specific Antigen, HM1.24," *Blood*, 90:3179-3186 (1997).
Ozaki et al., "Induction of myeloma cell death by a recombinant HLA class I-specific single-chain Fv diabody," *Dai 65 Nihon Ketsueki Gakkai, Dai 45 kai Nihon Ketsueki Gakkai Sokai*, Osaka (Aug. 28-31, 2003) (English translation included).
Pan et al., "An Antagonist Decoy Receptor and a Death Domain-Containing Receptor for TRAIL," *Science*, 277:815-818 (1997).
Pan et al., "The Receptor for the Cytotoxic Ligand TRAIL," *Science*, 276:111-113 (1997).
Paul, *Fundamental Immunology*, 3rd Edition, Raven Press, NY, Chapter 8, pp. 292-295 (1993).
Paul, *Fundamental Immunology*, Raven Press, NY, Chapter 8, p. 242 (1993).
Peipp et al., "Bispecific antibodies targeting cancer cells," *Biochem. Soc. Trans.*, 30:507-511 (2002).
Pettersen et al., "CD47 Signals T Cell Death," *J. Immunol.*, 7031-7040 (1999).
Pettersen et al., "Role of the TCR Binding Region of the HLA Class I alpha2 Domain in Regulation of Cell Adhesion and Proliferation," *J. Immunol.*, 156:1415-1424 (1996).
Pettersen et al., "The TCR-Binding Region of the HLA Class I $\alpha_2$ Domain Signals Rapid Fas-Independent Cell Death: A Direct Pathway for T Cell-Mediated Killing of Target Cells?" *J. Immunol.*, 160:4343-4352 (1998).
Petterson, "CD47 and death signaling in the immune system," *Apoptosis*, 5:299-306 (2000).
Piétri-Rouxel et al., "The biochemical effect of the naturally occurring Trp64→>Arg mutation on human β3-adrenoceptor activity," *Eur. J. Biochem.*, 247:1174-1179 (1997).
Plückthun et al., "New protein engineering approaches to multivalent and bispecific antibody fragments," *Immunotechnology*, 3:83-105 (1997).
Prados et al., "Induction of drug resistance in embryonal rhabdomyosarcoma treated with conventional chemotherapy is associated with HLA class I increase," *Neoplasma*, 53(3):226-231 (2006).
Rajagopal et al., "A form of anti-Tac (Fv) which is both single-chain and disulfide stabilized: comparison with its single-chain and disulfide-stabilized homologs," *Protein Engineering*, 10(12):1453-1459 (1997).
Reff et al., "A review of modifications to recombinant antibodies: attempt to increase efficacy in oncology applications," *Critical Reviews in Oncology and Hematology*, 40:25-35 (2001).
Reinhold et al., "In vivo expression of alternatively spliced forms of integrin-associated protein (CD47)," *J. Cell Science*, 108:3419-3425 (1995).
Reiter et al., "Engineering interchain disulfide bonds into conserved framework regions of Fv fragments: improved biochemical characteristics of recombinant immunotoxins containing disulfide-stabilized Fv," *Protein Engineering*, 7(5):697-704 (1994).
Reiter et al., "Stabilization of the Fv Fragments in Recombinant Immunotoxins by Disulfide Bonds Engineered into Conserved Framework Regions," *Biochemistry*, 33:5451-5459 (1994).
Retter et al., "Both Sm and DNA are Selecting Antigens in the Anti-Sm B Cell Response in Autoimmune MRL/*lpr* Mice, *J. Immunol.*, 156:1296-1306 (1996).
Ridgway et al., "'Knobs-into-holes' engineering of antibody $C_H3$ domains for heavy chain heterodimerization," *Protein Eng.*, 9:617-621 (1996).
Riechmann et al., "Reshaping Human Antibodies for Therapy," *Nature*, 332:323-327 (1988).
Rossi et al., "Development of New Multivalent-bispecific Agents for Pretargeting Tumor Localization and Therapy," *Clin. Cancer Res.*, 9:3886s-3896s (2003).
Roue et al. "Mitochondrial dysfunction in CD47-mediated caspase-independent cell death: ROS production in the absence of cytochrome c and AIF release," *Biochimie.*, 85:741-746 (2003).
Rousch et al., "Somatostatin displayed on filamentous phage as a receptor-specific agonist," *Br. J. Pharmacol.*, 125:5-16 (1998).
Rozsnyay et al., "Phenylarsine oxide (PAO) blocks antigen receptor-induced calcium response and tyrosine phosphorylation of a distinct group of proteins," *Immunology Lett.*, 37(2-3):197-205 (1993).
Rudikoff et al., "Single amino acid substitution altering antigen-binding specificity," *Proceedings of the National Academy of Sciences*, 79:1979-1983 (1982).
Sackstein, "The lymphocyte homing receptors: gatekeepers of the multistep paradigm," *Current Opinion in Hematology*, 12:444-450 (2005).
Sal-Man et al., "Arginine mutations within a transmembrane domain of Tar, an *Escherichia coli* aspartate receptor, can drive monodimer dissociation and heterodimer association in vivo," *Biochem. J.*, 385(1):29-36 (2005).
Sato et al., "CD22 Is Both a Positive and Negative Regulator of B Lymphocyte Antigen Receptor Signal Transduction: Altered Signaling in CD22-Deficient Mice," *Immunity*, 5:551-562 (1996).
Sato et al., "Reshaping a Human Antibody to Inhibit the Interleukin 6-Dependent Tumor Cell Growth," *Cancer Research*, 53:851-856 (1993).
Scheurle et al., "Cancer Gene Discovery Using Digital Differential Display," *Cancer Res.*, 60:4037-4043 (2000).
Schickel, et al., "Gene for Integrin-Associated Protein (IAP, CD47): Physical Mapping, Genomic Structure, and Expression Studies in Skeletal Muscle," *Biochem. Cell. Biol.*, 80(2):169-176 (2002).
Schmidt et al., "A bivalent single-chain antibody-toxin specific for ErbB-2 and the EGF receptor," *Int. J. Cancer*, 65(4):538-546 (1996).
Schwartz et al., "A 50-kDa Integrin-associated Protein Is Required for Integrin-regulated Calcium Entry in endothelial Cells," *J. Biol. Chem.*, 268(27):19931-19934 (1993).
Scott, "The Problem with Potency," *Nature Biotechnology*, 23(9):1037-1039 (2005).
Segal et al., "Bispecific antibodies in cancer therapy," *Current Opinion in Immunology*, 11:558-582 (1999).
Sekimoto et al., "Eradication of human myeloma cells by a recombinant HLA class I-specific single chain Fv diabody," *45th Annual Meeting of the American Society of Hematology*, San Diego, CA, USA (Dec. 6-9, 2003).
Sekimoto et al., "Eradication of Human Myeloma Cells by a Recombinant HLA Class I-Specific Single Chain Fv Diabody," *Blood*, 102:932a, XP009106629 (Abstract #3469) (Nov. 2003) [Abstract of the American Society of Hematology 45th Annual Meeting, Dec. 6-9, 2003, San Diego, California].
Sekine et al., Enrichment of Anti-Glomerular Antigen Antibody-Producing Cells in the Kidneys of MRL/MpJ-Fas(lpr) Mice, *J. Immunol.*, 172:3913-3921 (2004).
Shalaby et al., "Development of Humanized Bispecific Antibodies Reactive with Cytotoxic Lymphocytes and Tumor Cells Overexpressing the HER2 Protooncogene," *J. Exp. Med.*, 175:217-225 (1992).
Sheridan et al., "Control of TRAIL-Induced Apoptosis by a Family of Signaling and Decoy Receptors," *Science*, 277:818-821 (1997).
Shigeta et al., "Sperm-immobilizing monoclonal antibody to human seminal plasma antigens," *Clin. Exp. Immunol.*, 42:458-462 (1980).
Shulman et al., "A better cell line for making hybridomas secreting specific antibodies," *Nature*, 276:269-270 (1978).
Skerra, "Use of the tetracycline promoter for the tightly regulated production of a murine antibody fragment in *Escherichia coli*," *Gene*, 151:131-135 (1994).
Skolnick et al., "From genes to protein structure and function: novel applications of computational approaches in the genomic era," *Trends in Biotechnology*, 18:34-39 (2000).
Smith et al., "Inhibition of T Cell Activation by a Monoclonal Antibody Reactive Against the α3 Domain of Human MHC Class I Molecules," *J. Immunol.*, 153:1054-1067 (1994).

(56) References Cited

OTHER PUBLICATIONS

Smith-Gill et al., "Contributions of immunoglobulin heavy and light chains to antibody specificity for lysozyme and two haptens," *The Journal of Immunology*, 139:4135-4144 (1987).
Song et al., "Light chain of natural antibody plays a dominant role in protein antigen binding," *Biochemical and Biophysical Research Communications*, 268:390-394 (2000).
Sonneveld, "Multidrug resistance in haematological malignancies," *J. Intern. Med.*, 247:521-534 (2000).
Souyri et al., "A putative truncated cytokine receptor gene transduced by the myeloproliferative leukemia virus immortalizes hematopoietic progenitors," *Cell*, 63:1137-1147 (1990).
Spaargaren et al., "Antibody-induced Dimerization Activates the Epidermal Growth Factor Receptor Tyrosine Kinase," *The J. Biol. Chem.*, 266(3):1733-1739 (1981).
Stancovski et al., "Mechanistic aspects of the opposing effects of monoclonal antibodies to the ERBB2 receptor on tumor growth," *Proc. Natl. Acad. Sci. USA*, 88:8691-8695 (1991).
Stein et al., "Characterization of humanized IgG4 anti-HLA-DR monoclonal antibody that lacks effector cell functions but retains direct antilymphoma activity and increases the potency of rituximab," *Blood*, 108(8):2736-2744 (2006).
Suzuki et al., "YM477, a Novel Orally-Active Thrombopoietin Receptor Agonist," *Blood (ASH Annual Meeting Abstracts)*, 106:Abstract 2298 (2005).
Tahtis et al., "Biodistribution Properties of [111]Indium-labeled C-Functionalized *trans*-Cyclohexyl Diethylenetriaminepentaacetic Acid Humanized 3S193 Diabody and F(ab')$_2$ Constructs in a Breast Carcinoma Xenograft Model," *Clin. Cancer Res.*, 7:1061-1072 (2001).
Tan et al., "Contributions of a highly conserved $V_H/V_L$ hydrogen bonding interaction to scFv folding stability and refolding efficiency," *Biophysical Journal*, 75:1473-1482 (1998).
Tang et al., "Selection of linkers for a catalytic single-chain antibody using phage display technology", *The Journal of Biological Chemistry*, 271(26):15682-15686 (1996).
Tedder et al., "CD22, a B Lymphocyte-Specific Adhesion Molecule That Regulates Antigen Receptor Signaling," *Annu. Rev. Immunol.*, 15:481-504 (1997).
Thilenius et al., "Agonist antibody and Fas ligand mediate different sensitivity to death in the signaling pathways of Fas and cytoplasmic mutants," *Eur. J. Immunol.*, 27:1108-1114 (1997).
Trowbridge, I.S., "Interspecies Spleen-Myeloma Hybrid Producing Monoclonal Antibodies Against Mouse Lymphocyte Surface Glycoprotein, T200," *J. Exp. Med.*, 148:313-323 (1978).
Tsukakoshi, *New Pharmacology*, 3rd revised edition, Nankodo Co., Ltd., 557-568 (1997).
Turner et al., "Importance of the linker in expression of single-chain Fv antibody fragments: optimization of peptide sequence using phage display technology," *Journal of Immunological Methods*, 205:43-54 (1997).
Vajdos et al., "Comprehensive functional maps of the antigen-binding site of an anti-ErbB2 antibody obtained with shotgun scanning mutagenesis," *Journal of Molecular Biology*, 320:415-428 (2002).
Van Den Burg et al., "Selection of mutations for increased protein stability," *Curr. Opin. Biotechnol.*, 13(4):333-337 (2002).
Van Geelen et al., "Differential modulation of the TRAIL receptors and the CD95 receptor in colon carcinoma cell lines," *Br. J. Cancer*, 89(2):363-373 (2003).
Vargas-Madrazo et al., "An improved model of association for VH-VL immunoglobulin domains: asymmetries between VH and VL in the packing of some interface residues," *J. Mol. Recognit.*, 16(3):113-20 (2003).
Verma et al., "Antibody engineering: Comparison of bacterial, yeast, insect and mammalian expression systems," *Journal of Immunological Methods*, 216:165-181 (1998).
Vernon-Wilson et al., "CD47 is a ligand for rat macrophage membrane signal regulatory protein SIRP (OX41) and human SIRPalpha 1," *Eur. J. Immunol.*, 30:2130-2137 (2000).

Verstegen et al., "Thrombopoietin is a major limiting factor for selective outgrowth of human umbilical cord blood cells in non-obese diabetic/severe combined immunodeficient recipient mice," *Br. J. Haematol.*, 122(5):837-846 (2003).
Vieille et al., "Hyperthermophilic enzymes: sources, uses, and molecular mechanisms for thermostability," *Microbiology and Molecular Biology Reviews*, 65(1):1-43 (2001).
Volkel et al., "Optimized linker sequences for the expression of monomeric and dimeric bispecific single-chain diabodies," *Protein Engineering*, 14(10):815-823 (2001).
Wakalee et al., *Ann. Oncol.* On-line publication (Jul. 24, 2009).
Walczak et al., "TRAIL-R2: A Novel Apoptosis-Mediating Receptor for TRAIL," *EMBO J.*, 16:5386-5397 (1997).
Ward et al., "Binding activities of a repertoire of single immunoglobulin variable domains secreted from *Escherichia coli*," *Nature*, 341:544-546 (1989).
Whitlow et al., "An improved linker for single-chain Fv with reduced aggregation and enhanced proteolytic stability," *Protein Engineering*, 6(8):989-995 (1993).
Whitlow et al., "Multivalent Fvs: characterization of single-chain Fv oligomers and preparation of a bispecific Fv," *Protein Eng.*, 7(8):1017-1026 (1994).
Wiley et al., "Identification and Characterization of a New Member of the TNF Family that Induces Apoptosis," *Immunity*, 3:673-682 (1995).
Winkler et al., "Changing the Antigen Binding Specificity by Single Point Mutations of an Anti-p24 (HIV-1) Antibody," *J. Immunol.*, 265:4505-4514 (2000).
Woodle et al., "Anti-Human Class I MHC Antibodies Induce Apoptosis by a Pathway That Is Distinct from the Fas Antigen-Mediated Pathway," *J. Immunol.*, 158:2156-2164 (1997).
Woodle et al., "Anti-Human Class I α3 Domain-Specific Monoclonal Antibody Induces Programmed Cell Death in Murine Cells Expressing Human Class I MHC Transgenes," *Transplant. Proc.*, 30:1059-1060 (1998).
Woodle et al., "Class I MHC Mediates Programmed Cell Death in Human Lymphoid Cells," *Transplantation*, 64:140-146 (1997).
Worn et al., "Stability engineering of antibody single-chain Fv fragments," *J. Mol. Biol.*, 305:989-1010 (2001).
Wu et al., "Humanization of a murine monoclonal antibody by simultaneous optimization of framework and CDR residues," *Journal of Molecular Biology*, 294:151-162 (1999).
Wu et al., "Multimerization of a chimeric anti-CD20 single-chain Fv-Fc fusion protein is mediated through variable domain exchange," *Protein Eng.*, 14(12):1025-33 (2001).
Wu et al., "Tumor localization of anti-CEA single-chain Fvs: improved targeting by non-covalent dimers," *Immunotechnology*, 2:21-36 (1996).
Xie et al., "Direct Demonstration of MuSK Involvement in Acetylcholine Receptor Clustering Through Identification of Agonist ScFv," *Nature Biotechnology*, 15(8):768-771 (1997).
Xiong et al., "Efficient inhibition of human B-cell lymphoma xenografts with an anti-CD20 × anti-CD3 bispecific diabody," *Cancer Lett.*, 177:29-39 (2002).
Xu et al., "Insight into hepatocellular carcinogenesis at transcriptome level by comparing gene expression profiles of hepatocellular carcinoma with those of corresponding noncancerous liver," *Proc. Natl. Acad. Sci. USA*, 98:15089-15094 (2001).
Yagita et al., "TRAIL and its receptors as targets for cancer therapy," *Cancer Sci.*, 95:777-783 (2004).
Yanabu et al., "Tyrosine phosphorylation and p72syk activation by an anti-glycoprotein lb monoclonal antibody," *Blood*, 89(5):1590-1598 (1997).
Yarden et al., "Self-phosphorylation of epidermal growth factor receptor: evidence for a model of intermolecular allosteric activation," *Biochemistry*, 26(5):1434-1442 (1987).
Yelton et al., "Fusion of Mouse Myeloma and Spleen Cells," *Current Topics in Microbiology and Immunology*, 81:1-7 (1978).
Zhu et al., "An efficient route to the production of an IgG-like bispecific antibody", Protein Eng., 13:361-367 (2000).
Zhu et al., "Remodeling domain interfaces to enhance heterodimer formation," *Protein Science*, 6:781-788 (1997).

(56) References Cited

OTHER PUBLICATIONS

USPTO Non-Final Office Action in U.S. Appl. No. 10/582,304, mailed Dec. 9, 2010, 12 pages.
USPTO Restriction Requirement in U.S. Appl. No. 11/916,351, mailed Sep. 3, 2010, 8 pages.
Fish & Richardson P.C., Amendment and Response to Restriction Requirement dated Sep. 3, 2010 in U.S. Appl. No. 11/916,351, filed Dec. 2, 2010, 9 pages.
USPTO Non-Final Office Action in U.S. Appl. No. 11/916,351, mailed Mar. 3, 2011, 11 pages.
International Search Report for App. Ser. No. PCT/JP2006/311575, mailed Sep. 26, 2006, 3 pages.
International Preliminary Report on Patentability for App. Ser. No. PCT/JP2006/311575, dated Dec. 11, 2007, 5 pages.
European Search Report for App. Ser. No. EP 06 75 7198, dated Jun. 11, 2010, 2 pages.
European Search Report for App. Ser. No. EP 06 76 6512, dated Nov. 30, 2009, 6 pages.
USPTO Restriction Requirement in U.S. Appl. No. 11/916,979, mailed Jul. 1, 2010, 7 pages.
Fish & Richardson P.C., Amendment and Response to Restriction Requirement dated Jul. 1, 2010 in U.S. Appl. No. 11/916,979, filed Nov. 30, 2010, 9 pages.
USPTO Non-Final Office Action in U.S. Appl. No. 11/916,979, mailed Jan. 21, 2011, 15 pages.
International Search Report for App. Ser. No. PCT/JP2006/311600, mailed Aug. 29, 2006, 2 pages.
International Preliminary Report on Patentability for App. Ser. No. PCT/JP2006/31160, dated Dec. 11, 2007, 8 pages.
USPTO Restriction Requirement in U.S. Appl. No. 10/530,696, mailed Oct. 19, 2006, 8 pages.
Fish & Richardson P.C., Response to Restriction Requirement dated Oct. 19, 2006, in U.S. Appl. No. 10/530,696, filed Nov. 16, 2006, 1 page.
USPTO Non-Final Office Action in U.S. Appl. No. 10/530,696, mailed Dec. 21, 2006, 19 pages.
Fish & Richardson P.C., Amendment in Reply to Office Action dated Dec. 21, 2006 in U.S. Appl. No. 10/530,696, filed Apr. 23, 2007, 16 pages.
USPTO Final Office Action in U.S. Appl. No. 10/530,696, mailed Aug. 8, 2007, 13 pages.
USPTO Interview Summary in U.S. Appl. No. 10/530,696, mailed Nov. 26, 2007, 3 pages.
Fish & Richardson P.C., Amendment in Reply to Office Action dated Aug. 8, 2007 in U.S. Appl. No. 10/530,696, filed Dec. 6, 2007, 12 pages.
USPTO Advisory Action in U.S. Appl. No. 10/530,696, mailed Dec. 14, 2007, 3 pages.
USPTO Non-Final Office Action in U.S. Appl. No. 10/530,696, mailed Feb. 5, 2008, 9 pages.
Fish & Richardson, Amendment in Reply to Action dated Feb. 5, 2008 in U.S. Appl. No. 10/530,696, filed Aug. 5, 2008, 7 pages.
USPTO Non-Final Office Action in U.S. Appl. No. 10/530,696, mailed Nov. 17, 2008, 18 pages.
Fish & Richardson, Amendment in Reply to Action dated Nov. 17, 2008 in U.S. Appl. No. 10/530,696, filed Feb. 17, 2009, 14 pages.
USPTO Final Office Action in U.S. Appl. No. 10/530,696, mailed Jun. 8, 2009, 10 pages.
Fish & Richardson, Amendment in Reply to Action dated Jun. 8, 2009 in U.S. Appl. No. 10/530,696, filed Nov. 30, 2009, 10 pages.
USPTO Non-Final Office Action in U.S. Appl. No. 10/530,696, mailed Apr. 23, 2010, 9 pages.
Fish & Richardson, Amendment in Reply to Action dated Apr. 23, 2010 in U.S. Appl. No. 10/530,696, filed Oct. 22, 2010, 8 pages.
USPTO Non-Final Office Action in U.S. Appl. No. 10/530,696, mailed Jan. 7, 2011, 10 pages.
International Search Report for App. Ser. No. PCT/JP2003/013063, mailed Nov. 18, 2003, 2 pages.
International Preliminary Report on Patentability for App. Ser. No. PCT/JP2003/013063, dated Feb. 6, 2004, 4 pages.

European Search Report for App. Ser. No. EP 03 75 1456, dated Apr. 4, 2006, 2 pages.
Fish & Richardson P.C., Amendment in Reply to Action dated Apr. 1, 2009 in U.S. Appl. No. 10/582,304, filed Jun. 30, 2009, 15 pages.
USPTO Non-Final Office Action in U.S. Appl. No. 10/582,304, mailed Sep. 15, 2009, 22 pages.
Fish & Richardson P.C., Amendment in Reply to Action dated Sep. 15, 2009 in U.S. Appl. No. 10/582,304, filed Jan. 13, 2010, 13 pages.
USPTO Non-Final Office Action in U.S. Appl. No. 10/582,304, mailed Mar. 24, 2010, 10 pages.
Fish & Richardson P.C., Amendment in Reply to Action dated Mar. 24, 2010 in U.S. Appl. No. 10/582,304, filed Jul. 26, 2010, 14 pages.
USPTO Non-Final Office Action in U.S. Appl. No. 10/582,304, mailed Oct. 14, 2010, 7 pages.
International Search Report for App. Ser. No. PCT/JP2004/018501, mailed Mar. 29, 2005, 2 pages.
International Search Report for App. Ser. No. PCT/JP2004/005152, mailed Jul. 20, 2004, 2 pages.
International Preliminary Report on Patentability for App. Ser. No. PCT/JP2004/005152, dated Feb. 14, 2005, 6 pages.
European Search Report for App. Ser. No. EP 04 72 6750, dated Feb. 4, 2008, 3 pages.
USPTO Non-Final Office Action in U.S. Appl. No. 11/547,747, mailed Jun. 1, 2009, 41 pages.
Fish & Richardson P.C., Amendment in Reply to Action dated Jun. 1, 2009 in U.S. Appl. No. 11/547,747, filed Nov. 30, 2009, 12 pages.
USPTO Final Office Action in U.S. Appl. No. 11/547,747, mailed Feb. 19, 2010, 15 pages.
Fish & Richardson P.C., Amendment in Reply to Action dated Feb. 19, 2010 in U.S. Appl. No. 11/547,747, filed Jun. 18, 2010, 13 pages.
International Search Report for App. Ser. No. PCT/JP2007/063946, mailed Aug. 14, 2007, 7 pages.
International Preliminary Report on Patentability for App. Ser. No. PCT/JP2007/063946, dated Jan. 20, 2009, 10 pages.
European Search Report for App. Ser. No. EP 07 79 0727, dated Nov. 13, 2009, 5 pages.
USPTO Restriction Requirement in U.S. Appl. No. 10/548,727, mailed Apr. 12, 2007, 6 pages.
Fish & Richardson P.C., Reply to Restriction Requirement dated Apr. 12, 2007 in U.S. Appl. No. 10/548,727, filed May 3, 2007, 1 page.
USPTO Non-Final Office Action in U.S. Appl. No. 10/548,727, mailed Aug. 3, 2007, 21 pages.
Fish & Richardson P.C., Amendment in Reply to Action dated Aug. 3, 2007 in U.S. Appl. No. 10/548,727, filed Jan. 15, 2008, 15 pages.
USPTO Final Office Action in U.S. Appl. No. 10/548,727, mailed Apr. 29, 2008, 23 pages.
USPTO Advisory Action in U.S. Appl. No. 10/548,727, mailed Sep. 24, 2008, 6 pages.
USPTO Non-Final Office Action in U.S. Appl. No. 10/548,727, mailed Jan. 28, 2009, 16 pages.
Fish & Richardson P.C., Amendment in Reply to Action dated Jan. 28, 2009 in U.S. Appl. No. 10/548,727, filed Jun. 26, 2009, 9 pages.
USPTO Notice of Allowance in U.S. Appl. No. 10/548,727, mailed Nov. 25, 2009, 29 pages.
International Search Report for App. Ser. No. PCT/JP2004/003334, mailed Jun. 15, 2004, 3 pages.
International Preliminary Report on Patentability for App. Ser. No. PCT/JP2004/003334, dated May 2, 2005, 6 pages.
USPTO Notice of Allowance in U.S. Appl. No. 10/551,504, mailed Dec. 16, 2010, 5 pages.
USPTO Restriction Requirement in U.S. Appl. No. 12/874,872, mailed Dec. 15, 2010, 6 pages.
International Search Report for App. Ser. No. PCT/JP2008/054443, dated May 27, 2008, 7 pages.
Fish & Richardson P.C., Reply to Restriction Requirement dated Dec. 15, 2010 in U.S. Appl. No. 12/874,872, filed Jan. 18, 2011, 8 pages.
Carpenter et al., "Rational design of stable lyophilized protein formulations: some practical advice", Pharmaceutical Research, 14(8):969-975, 1997.
Carpenter et al., "Rational design of stable lyophilized protein formulations: theory and practice", Pharma Biotechnol. 13:109-133, 2002.

(56) References Cited

OTHER PUBLICATIONS

Cleland et al., "A specific molar ratio of stabilizer to protein is required for storage stability of a lyophilized monoclonal antibody", Journal of Pharmaceutical Sciences 90(3):310-321, 2001.
Frokjaer et al., "Protein drug stability: a formulation challenge", Nature Rev Drug Discov. 4:298-306, 2005.
Garcia-Gonzalez et al., "Purification of murine IgG3 and IgM monoclonal antibodies by euglobulin precipitation", Journal of Immunological Methods 111:17-23, 1988.
Gombotz et al., "The stabilization of a human IgM monoclonal antibody with poly(vinylpyrrolidone)", Pharmaceutical Research 11(5):624-632, 1994.
Lee et al., "Reversible dimer formation and stability of the antitumour single chain Fv antibody MFE-23 by neutron scattering, analytical ultracentrifugation, and NMR and FR-IR spectroscopy", J. Mol. Biol. 320:107-127, 2002.
Martsev et al., "Antiferritin single-chain antibody: a functional protein with incomplete folding?" FEBS Letters 441:458-462, 1998.
Sharma et al., "Study of IgM aggregation in serum of patients with macroglobulinemia", Clin Chem Lab Med 38(8):759-764, 2000.
Shimba et al., "Comparative thermodynamic analyses of the Fv, Fab* and Fab fragments of anti-dansyl mouse monoclonal antibody", FEBS Letters 360:247-250, 1995.
Shire et al., "Challenges in the development of high protein concentration formulations", Journal of Pharmaceutical Sciences 93(6):1390-1402, 2004.
Wang et al., "Instability, stabilization, and formulation of liquid protein pharmaceuticals", International Journal of Pharmaceutics 185:129-188, 1999.
Wang et al., "Lyophilization and development of solid protein pharmaceuticals", International Journal of Pharmaceutics 203:1-60, 2000.
Wang et al., "Protein aggregation and its inhibition in biopharmaceutics", International Journal of Pharmaceutics 289:1-30, 2005.
Carrel et al., "Recognition of HLA-A1 by murine monoclonal antibodies," Tissue Antigens., 43:110-115 (1994).
USPTO Restriction Requirement in U.S. Appl. No. 13/497,545, dated Feb. 26, 2013, 8 pages.
Kubo et al., "A human monoclonal antibody that detects HLA-A1, A23 and A24 antigens," Tissue Antigens, 41:186-189 (1993).
Mulder et al., "A human monoclonal antibody against HLA-Cw1 and a human monoclonal antibody against an HLA-A locus determinant derived from a single uniparous female," Tissue Antigens, 52:393-396 (1998).
Scheinberg et al., "Inhibition of cell proliferation with an HLA-A-specific monoclonal antibody," Tissue Antigens, 38:213-223 (1991).
Wang et al., "Specificity and functional characteristics of anti-HLA-A mAbs LGIII-147.4.1 and LGIII-220.6.2," Tissue Antigens, 62:139-148 (2003).
International Search Report for App. Ser. No. PCT/JP2010/066494, mailed Dec. 28, 2010, 6 pages.
International Preliminary Report on Patentability for App. Ser. No. PCT/JP2010/066494, dated Apr. 11, 2012, 8 pages.
Fish & Richardson P.C., Amendment and Reply to Restriction Requirement dated Feb. 26, 2013 in U.S. Appl. No. 13/497,545, filed Jul. 26, 2013, 7 pages.
Arndt et al., "Antigen binding and stability properties of non-covalently linked anti-CD22 single-chain Fv dimers," FEBS Lett., 578(3):257-261 (2004).
Ausubel et al., Short Protocols in Molecular Biology, 3rd Edition, 1985, p. A1-44.
Bork et al., "The immunoglobulin fold. Structural classification, sequence patterns and common core," J. Mol. Biol., 242(4):309-320 (1994).
Colcher et al., "Single-chain antibodies in pancreatic cancer," Ann N Y Acad. Sci., 880:263-280 (1999).
Humes et al., "Direct toxic effect of the radiocontrast agent diatrizoate on renal proximal tubule cells," Am. J. Physiol., 252(2):F246-F255 (1987).

Lower, Chemical Equilibrium, A Chem1 Reference Text, 2001, pp. 1-28.
Spada et al., "Reproducing the Natural Evolution of Protein Structural Features with the Selectively Infective Phage (SIP) Technology. The Kink in the First Strand of Antibody kappa Domains," J. Mol. Biol., 283:395-407 (1998).
Wörn et al., "Different Equilibrium Stability Behavior of ScFv Fragments: Identification, Classification, and Improvement by Protein Engineering," Biochemistry, 38:8739-8750 (1999).
USPTO Final Office Action in U.S. Appl. No. 11/916,979, mailed Sep. 16, 2011, 20 pages.
Fish & Richardson P.C., Amendment in Reply to Action dated Sep. 16, 2011 in U.S. Appl. No. 11/916,979, filed Mar. 15, 2012, 15 pages.
USPTO Final Office Action in U.S. Appl. No. 11/910,117, mailed Sep. 9, 2011, 12 pages.
Fish & Richardson P.C., Amendment in Reply to Action dated Sep. 9, 2011 in U.S. Appl. No. 11/910,117, filed Mar. 9, 2012, 18 pages.`
USPTO Final Office Action in U.S. Appl. No. 11/916,351, mailed Oct. 28, 2011, 10 pages.
Fish & Richardson P.C., Amendment in Reply to Action dated Oct. 28, 2011 in U.S. Appl. No. 11/916,351, filed Apr. 30, 2012, 28 pages.
USPTO Restriction Requirement in U.S. Appl. No. 12/307,042, mailed Dec. 6, 2011, 9 pages.
USPTO Notice of Allowance in U.S. Appl. No. 10/530,696, mailed Dec. 12, 2011, 8 pages.
Fish & Richardson P.C., Amendment in Reply to Action dated Nov. 8, 2012 in U.S. Appl. No. 11/910,117, filed May 7, 2013, 18 pages.
Albrecht et al., "Production of soluble ScFvs with C-terminal-free thiol for site-specific conjugation or stable dimeric ScFvs on demand," Bioconjug. Chem., 15:16-26 (2004).
Columbia Encyclopedia, "Structural Isomers," 3 pages (2013).
USPTO Final Office Action in U.S. Appl. No. 11/910,117, mailed Jul. 2, 2013, 18 pages.
USPTO Non-Final Office Action in U.S. Appl. No. 11/910,117, mailed Nov. 8, 2012, 10 pages.
Armijos et al., "Comparison of the effectiveness of two topical paromomycin treatments versus meglumine antimoniate for New World cutaneous leishmaniasis," Acta Trop., 91(2):153-60 (2004).
Friton et al., "Clinical efficacy of meloxicam (Metacam) and flunixin (Finadyne) as adjuncts to antibacterial treatment of respiratory disease in fattening cattle," Berl. Munch Tierarztl. Wochenschr., 117(7-8):304-9 (2004).
Goyen et al., "Gadobenate dimeglumine (MultiHance) for magnetic resonance angiography: review of the literature," Eur. Radiol., 13 Suppl 3:N19-27 (2003).
Grossman et al., "Multiple sclerosis: gadolinium enhancement in MR imaging," Radiology, 161(3):721-5 (1986).
U.S. Appl. No. 10/582,413, filed Oct. 26, 2006, Ohtomo et al.
Devito et al., "Epitope fine specificity of human anti-HLA-A2 antibodies. Identification of four epitopes including a haptenlike epitope on HLA-A2 at lysine 127," Hum. Immunol., 37:165-177 (1993).
Heppner et al., "Tumor heterogeneity: biological implications and therapeutic consequences," Cancer Metastasis Rev., 2:5-23 (1983).
Kornbluth et al., "Evidence for the role of class I and class II HLA antigens in the lytic function of a cloned line of human natural killer cells," J. Immunol., 134:728-735 (1985).
Lozano et al., "Identification of the amino acid residues defining an intralocus determinant in the alpha 1 domain of HLA-A molecules," Immunogenetics, 30:50-53 (1989).
Rowe et al., "Handbook of Pharmaceutical Excipients, 4$^{th}$ ed.," 381-382 (2003), Published by the Pharmaceutical Press and the American Pharmaceutical Association.
Spear et al., "Evidence for a shared HLA-A intralocus determinant defined by monoclonal antibody 131," J. Exp. Med., 162:1802-1810 (1985).
U.S. Appl. No. 11/910,117, filed Aug. 28, 2007, Igawa et al.
Abe et al., "Surrogate thrombopoietin," Immunology Letters, 61:73-78 (1998).
Beresford et al., "Binding Characteristics and Tumor Targeting of a Covalently Linked Divalent CC49 Single-Chain Antibody," Int. J. Cancer, 81:911-917 (1999).

(56) References Cited

OTHER PUBLICATIONS

Bowie et al., "Deciphering the Message in Protein Sequences: Tolerance to Amino Acid Substitutions," *Science*, 247:1306-1310 (1990).
Casset et al., "A peptide mimetic of an anti-CD4 monoclonal antibody by rational design," *Biochemical and Biophysical Research Communications*, 307:198-205 (2003).
Chen et al., "Selection and analysis of an optimized anti-VEGF antibody: crystal structure of an affinity-matured Fab in complex with antigen," *Journal of Molecular Biology*, 293:865-881 (1999).
Creighton, T., "Protein folding," *Biochem. J.*, 270(1):1-16 (1990).
Daniel et al., "Pathway of apoptosis induced in Jurkat T Lymphoblasts by anti-HLA Class I antibodies," *Human Immunology*, 65(3):189-199 (2004).
Dejonge et al., "In vivo retargeting of T cell effector function by recombinant bispecific single chain Fv (anti-DC3 × anti-idiottype) induces long term survival of the murine BCL1 lymphoma model," *J. Immunol.*, 161(3):1454-1461 (1998).
Deng et al., "An Agonist Murine Monoclonal Antibody to the Human c-Mpl Receptor Stimulates Megakaryocytopoiesis," *Blood*, 92:1981-1988 (1998).
Elliott et al., "Activation of the Erythropoietin (EPO) Receptor by Bivalent Anti-EPO Receptor Antibodies," *J. Biol. Chem.*, 271:24691-24697 (1996).
Kipriyanov et al., "Bispecific CD3 × CD19 diabody for T cell-mediated lysis of malignant human B cells," *In. J. Cancer*, 77:763-772 (1998).
Kontermann, R., "Recombinant bispecific antibodies for cancer therapy," *Acta Pharmacol. Sin.*, 26(1):1-9 (2005).
Le Gall et al., "Effect of linker sequences between the antibody variable domains on the formation, stability and biological activity of a bispecific tandem diabody," *Protein Engineering Design & Selection*, 17(4):357-366 (2004).
Lin et al., "Structure-function relationships in glucagon: properties of highly purified des-His-1-, monoiodo-, and (des-Asn-28, Thr-29)(homoserine lactone-27)-glucagon," *Biochemistry*, 14:1559-1563 (1975).
Ngo et al., "Computational Complexity, Protein Structure Prediction, and the Levinthal Paradox," *The Protein Folding Problem and Tertiary Structure Prediction*, Merz, Jr. et al. Editors, Birkhauser Boston, 433-506 (1994).
Palacios et al., "IL-3-dependent mouse clones that express B-220 surface antigen, contain Ig genes in germ-line configuration, and generate B lymphocutes in vivo," *Cell*, 41:727-734 (1985).
Schwartz et al., "A superactive insulin: [B10-aspartic acid]insulin(human)," *Proc. Natl. Acad. Sci. USA.*, 84:6408-6411 (1987).
Sekimoto et al., "A Single-Chain Fv Diabody Against Human Leukocyte Antigen-A Molecules Specifically Induces Myeloma Cell Death in the Bone Marrow Environment," *Cancer Res.*, 67(3):1184-1192 (2007).
Souyri, M., "Mpl: from an acute myeloproliferative virus to the isolation of the long sought thrombopoietin," *Seminars in Hematology*, 35(3):222-231 (1998).
Wells, "Perspectives in Biochemistry," *Biochemistry*, 29(37):8509-8517 (1990).

USPTO Restriction Requirement in U.S. Appl. No. 10/551,504, mailed Jun. 27, 2008, 6 pages.
Fish & Richardson P.C., Response to Restriction Requirement dated Jun. 27, 2008 in U.S. Appl. No. 10/551,504, filed Sep. 29, 2008, 13 pages.
USPTO Restriction Requirement in U.S. Appl. No. 10/551,504, mailed Dec. 16, 2008, 5 pages.
Fish & Richardson P.C., Response to Restriction Requirement dated Dec. 16, 2008 in U.S. Appl. No. 10/551,504, filed Dec. 23, 2008, 14 pages.
USPTO Non-Final Office Action in U.S. Appl. No. 10/551,504, mailed Apr. 15, 2009, 35 pages.
Fish & Richardson P.C., Amendment in Reply to Action dated Apr. 15, 2009 in U.S. Appl. No. 10/551,504, filed Aug. 14, 2009, 19 pages.
Japanese Patent Office, International Search Report for App. Ser. No. PCT/JP2004/018506, mailed Mar. 22, 2005, 3 pages.
International Preliminary Report on Patentability for App. Ser. No. PCT/JP2004/018506, 8 pages, 2006.
European Search Report for App. Ser. No. EP 04 82 0316, dated Jul. 17, 2008, 3 pages.
USPTO Restriction Requirement in U.S. Appl. No. 10/582,304, mailed Nov. 20, 2008, 7 pages.
Fish & Richardson P.C., Response to Restriction Requirement dated Nov. 20, 2008 in U.S. Appl. No. 10/582,304, filed Dec. 16, 2008, 3 pages.
USPTO Non-Final Office Action in U.S. Appl. No. 10/582,304, mailed Apr. 1, 2009, 38 pages.
Fish & Richardson P.C., Amendment in Reply to Office Action dated Apr. 1, 2009 in U.S. Appl. No. 10/582,304, filed Jun. 30, 2009, 15 pages.
Japanese Patent Office, International Search Report for App. Ser. No. PCT/JP2004/018501, mailed Mar. 29, 2005, 2 pages.
International Preliminary Report on Patentability for App. Ser. No. PCT/JP2004/018501, dated Nov. 4, 2005, 7 pages.
European Search Report for App. Ser. No. EP 04 82 0311, dated Jan. 28, 2009, 4 pages.
Japanese Patent Office, International Search Report for App. Ser. No. PCT/JP2006/306800, mailed May 16, 2006, 4 pages.
International Preliminary Report on Patentability for App. Ser. No. PCT/JP2006/306800, dated Oct. 3, 2007, 6 pages.
European Search Report for App. Ser. No. EP 06 73 0748, dated Apr. 22, 2009, 7 pages.
USPTO Restriction Requirement in U.S. Appl. No. 11/913,229, mailed Jul. 8, 2009, 6 pages.
Fish & Richardson P.C., Response to Restriction Requirement dated Jul. 8, 2009 in U.S. Appl. No. 11/913,229, filed Aug. 4, 2009, 1 page.
Japanese Patent Office, International Search Report for App. Ser. No. PCT/JP2006/309890, mailed Jul. 18, 2006, 2 pages.
International Preliminary Report on Patentability for App. Ser. No. PCT/JP2006/309890, dated Nov. 19, 2007, 5 pages.
European Search Report for App. Ser. No. EP 06 74 6578, dated Jun. 25, 2009, 2 pages.
Japanese Patent Office, International Search Report for App. Ser. No. PCT/JP2006/311625, mailed Aug. 22, 2006, 2 pages.
International Preliminary Report on Patentability for App. Ser. No. PCT/JP2006/311625, dated Dec. 11, 2007, 4 pages.

* cited by examiner

|  |  |  | CONTROL | MEGLUMINE |
|---|---|---|---|---|
| sc(Fv)2 | mVB22B | 40°C-1W | 13 | 4 |
|  |  | 40°C-2W | 22 | 7 |
|  |  |  | CONTROL | MEGLUMINE |
|  | 2D7 | 40°C-1W | 1 | 0 |
|  |  | 40°C-2W | 3 | 0 |
|  |  |  | CONTROL | MEGLUMINE |
|  | 12E10 | 55°C-1W | 62 | 25 |
|  |  | 55°C-2W | 84 | 31 |
|  |  |  | CONTROL | MEGLUMINE |
| IgG HUMANIZED ANTI-IL-6 RECEPTOR ANTIBODY | | 60°C-1W | 2 | 1 |
|  |  | 60°C-3W | 12 | 9 |

FIG. 2

HUMANIZED ANTI-IL-6 RECEPTOR ANTIBODY (116 mg/mL)

| | BULK REAGENT | | AGGREGATION CONTENT (%) | BULK REAGENT | | AGGREGATION CONTENT (%) |
|---|---|---|---|---|---|---|
| AFTER FREEZE-DRYING | SUCROSE | 100mg | 0.03 | MEGLUMINE | 55mg | 0.00 |
| | | 70mg | 0.07 | | 40mg | 0.03 |
| | | 50mg | 0.16 | | 30mg | 0.06 |

| | BULK REAGENT | | AGGREGATION CONTENT (%) | BULK REAGENT | | AGGREGATION CONTENT (%) |
|---|---|---|---|---|---|---|
| FREEZE-DRIED PREPARATION AFTER ONE-MONTH ACCELERATION TEST AT 40°C | SUCROSE | 100mg | 0.54 | MEGLUMINE | 55mg | 0.47 |
| | | 70mg | 0.99 | | 40mg | 0.56 |
| | | 50mg | 1.57 | | 30mg | 0.87 |

| | BULK REAGENT | | AGGREGATION CONTENT (%) | BULK REAGENT | | AGGREGATION CONTENT (%) |
|---|---|---|---|---|---|---|
| SOLUTION PREPARATION AFTER TWO-WEEK ACCELERATION TEST AT 25°C | SUCROSE | 100mg | 0.23 | MEGLUMINE | 55mg | 0.15 |
| | | 70mg | 0.24 | | 40mg | 0.19 |
| | | 50mg | 0.40 | | 30mg | 0.24 |

FIG. 3

```
                         SEQUENCE LISTING

<160> NUMBER OF SEQ ID NOS: 52

<210> SEQ ID NO 1
<211> LENGTH: 505
<212> TYPE: PRT
<213> ORGANISM: Homo sapiens
<220> FEATURE:
<223> OTHER INFORMATION: An artificially synthesized scFv sequence

<400> SEQUENCE: 1

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Asn Ser
            20                  25                  30

Trp Met Asn Trp Val Arg Gln Arg Pro Gly Lys Gly Leu Glu Trp Ile
        35                  40                  45

Gly Arg Ile Tyr Pro Gly Asp Gly Glu Thr Ile Tyr Asn Gly Lys Phe
    50                  55                  60

Arg Val Arg Val Thr Ile Thr Ala Asp Glu Ser Thr Ser Thr Ala Tyr
65                  70                  75                  80

Met Gln Leu Ser Ser Leu Arg Ser Glu Asp Thr Ala Val Tyr Tyr Cys
                85                  90                  95

Ala Arg Gly Tyr Asp Asp Tyr Ser Phe Ala Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Asp Ile Val Met Thr Gln Ser Pro Leu Ser Leu
    130                 135                 140

Pro Val Thr Pro Gly Glu Pro Ala Ser Ile Ser Cys Arg Ser Ser Lys
145                 150                 155                 160
```

```
Ser Leu Leu His Ser Asn Gly Asn Thr Tyr Leu Tyr Trp Phe Leu Gln
            165                 170                 175

Lys Pro Gly Gln Ser Pro Gln Leu Leu Ile Tyr Arg Met Ser Asn Leu
        180                 185                 190

Ala Ser Gly Val Pro Asp Arg Phe Ser Gly Ser Gly Ser Gly Thr Asp
        195                 200                 205

Phe Thr Leu Lys Ile Ser Arg Val Glu Ala Glu Asp Val Gly Val Tyr
        210                 215                 220

Tyr Cys Met Gln His Ile Glu Tyr Pro Phe Thr Phe Gly Gln Gly Thr
225                 230                 235                 240

Lys Leu Glu Ile Lys Gly Gly Gly Gly Ser Gly Gly Gly Gly Ser Gly
            245                 250                 255

Gly Gly Gly Ser Gln Val Gln Leu Val Gln Ser Gly Pro Glu Val Lys
        260                 265                 270

Lys Pro Gly Ala Ser Val Lys Val Ser Cys Lys Ala Ser Gly Tyr Thr
        275                 280                 285

Phe Thr Asn Ser Trp Met Asn Trp Val Arg Gln Arg Pro Gly Lys Gly
        290                 295                 300

Leu Glu Trp Ile Gly Arg Ile Tyr Pro Gly Asp Gly Glu Thr Ile Tyr
305                 310                 315                 320

Asn Gly Lys Phe Arg Val Arg Val Thr Ile Thr Ala Asp Glu Ser Thr
            325                 330                 335

Ser Thr Ala Tyr Met Gln Leu Ser Ser Leu Arg Ser Glu Asp Thr Ala
        340                 345                 350

Val Tyr Tyr Cys Ala Arg Gly Tyr Asp Asp Tyr Ser Phe Ala Tyr Trp
        355                 360                 365

Gly Gln Gly Thr Thr Val Thr Val Ser Gly Gly Gly Gly Ser Gly
        370                 375                 380

Gly Gly Gly Ser Gly Gly Gly Ser Asp Ile Val Met Thr Gln Ser
385                 390                 395                 400

Pro Leu Ser Leu Pro Val Thr Pro Gly Glu Pro Ala Ser Ile Ser Cys
            405                 410                 415

Arg Ser Ser Lys Ser Leu Leu His Ser Asn Gly Asn Thr Tyr Leu Tyr
        420                 425                 430

Trp Phe Leu Gln Lys Pro Gly Gln Ser Pro Gln Leu Leu Ile Tyr Arg
        435                 440                 445

Met Ser Asn Leu Ala Ser Gly Val Pro Asp Arg Phe Ser Gly Ser Gly
        450                 455                 460

Ser Gly Thr Asp Phe Thr Leu Lys Ile Ser Arg Val Glu Ala Glu Asp
465                 470                 475                 480

Val Gly Val Tyr Tyr Cys Met Gln His Ile Glu Tyr Pro Phe Thr Phe
            485                 490                 495

Gly Gln Gly Thr Lys Leu Glu Ile Lys
        500                 505

<210> SEQ ID NO 2
<211> LENGTH: 505
<212> TYPE: PRT
<213> ORGANISM: Mus musculus
<220> FEATURE:
<223> OTHER INFORMATION: An artificially synthesized scFv sequence

<400> SEQUENCE: 2

Gln Val Gln Leu Gln Gln Ser Gly Pro Glu Leu Val Lys Pro Gly Ala
1               5                   10                  15
```

-continued

```
Ser Val Lys Ile Ser Cys Lys Ala Ser Gly Tyr Ala Phe Thr Asn Ser
             20                  25                  30

Trp Met Asn Trp Val Lys Gln Arg Pro Gly Lys Gly Leu Glu Trp Ile
         35                  40                  45

Gly Arg Ile Tyr Pro Gly Asp Gly Glu Thr Ile Tyr Asn Gly Lys Phe
     50                  55                  60

Arg Val Lys Ala Thr Leu Thr Ala Asp Lys Ser Ser Ser Thr Ala Tyr
 65                  70                  75                  80

Met Asp Ile Ser Ser Leu Thr Ser Glu Asp Ser Ala Val Tyr Phe Cys
                 85                  90                  95

Ala Arg Gly Tyr Asp Asp Tyr Ser Phe Ala Tyr Trp Gly Gln Gly Thr
             100                 105                 110

Leu Val Thr Val Ser Ala Gly Gly Gly Ser Gly Gly Gly Gly Ser
         115                 120                 125

Gly Gly Gly Gly Ser Asp Ile Val Met Thr Gln Ala Ala Pro Ser Ile
     130                 135                 140

Pro Val Thr Pro Gly Glu Ser Val Ser Ile Ser Cys Arg Ser Ser Lys
145                 150                 155                 160

Ser Leu Leu His Ser Asn Gly Asn Thr Tyr Leu Tyr Trp Phe Leu Gln
                 165                 170                 175

Arg Pro Gly Gln Ser Pro Gln Leu Leu Ile Tyr Arg Met Ser Asn Leu
             180                 185                 190

Ala Ser Gly Val Pro Asp Arg Phe Ser Gly Ser Gly Ser Gly Thr Ala
         195                 200                 205

Phe Thr Leu Arg Ile Ser Arg Val Glu Ala Glu Asp Val Gly Val Tyr
210                 215                 220

Tyr Cys Met Gln His Ile Glu Tyr Pro Phe Thr Phe Gly Ser Gly Thr
225                 230                 235                 240

Lys Leu Glu Ile Lys Gly Gly Gly Ser Gly Gly Gly Gly Ser Gly
                 245                 250                 255

Gly Gly Gly Ser Gln Val Gln Leu Gln Gln Ser Gly Pro Glu Leu Val
         260                 265                 270

Lys Pro Gly Ala Ser Val Lys Ile Ser Cys Lys Ala Ser Gly Tyr Ala
275                 280                 285

Phe Thr Asn Ser Trp Met Asn Trp Val Lys Gln Arg Pro Gly Lys Gly
290                 295                 300

Leu Glu Trp Ile Gly Arg Ile Tyr Pro Gly Asp Gly Glu Thr Ile Tyr
305                 310                 315                 320

Asn Gly Lys Phe Arg Val Lys Ala Thr Leu Thr Ala Asp Lys Ser Ser
                 325                 330                 335

Ser Thr Ala Tyr Met Asp Ile Ser Ser Leu Thr Ser Glu Asp Ser Ala
             340                 345                 350

Val Tyr Phe Cys Ala Arg Gly Tyr Asp Asp Tyr Ser Phe Ala Tyr Trp
         355                 360                 365

Gly Gln Gly Thr Leu Val Thr Val Ser Ala Gly Gly Gly Ser Gly
     370                 375                 380

Gly Gly Gly Ser Gly Gly Gly Gly Ser Asp Ile Val Met Thr Gln Ala
385                 390                 395                 400

Ala Pro Ser Ile Pro Val Thr Pro Gly Glu Ser Val Ser Ile Ser Cys
                 405                 410                 415

Arg Ser Ser Lys Ser Leu Leu His Ser Asn Gly Asn Thr Tyr Leu Tyr
             420                 425                 430

Trp Phe Leu Gln Arg Pro Gly Gln Ser Pro Gln Leu Leu Ile Tyr Arg
```

```
                435                 440                 445
Met Ser Asn Leu Ala Ser Gly Val Pro Asp Arg Phe Ser Gly Ser Gly
        450                 455                 460

Ser Gly Thr Ala Phe Thr Leu Arg Ile Ser Arg Val Glu Ala Glu Asp
465                 470                 475                 480

Val Gly Val Tyr Tyr Cys Met Gln His Ile Glu Tyr Pro Phe Thr Phe
                485                 490                 495

Gly Ser Gly Thr Lys Leu Glu Ile Lys
                500                 505

<210> SEQ ID NO 3
<211> LENGTH: 501
<212> TYPE: PRT
<213> ORGANISM: Homo sapiens
<220> FEATURE:
<223> OTHER INFORMATION: An artificially synthesized scFv sequence

<400> SEQUENCE: 3

Gln Val Gln Leu Gln Gln Ser Gly Pro Gly Leu Val Lys Pro Ser Glu
1               5                   10                  15

Thr Leu Ser Leu Thr Cys Thr Val Ser Gly Asp Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Ser Gln Phe Ser Leu
65                  70                  75                  80

Lys Leu Ser Ser Val Thr Ala Ala Asp Thr Ala Val Tyr Tyr Cys Ala
                85                  90                  95

Arg Gly Arg Tyr Phe Asp Val Trp Gly Arg Gly Thr Met Val Thr Val
            100                 105                 110

Ser Ser Gly Gly Gly Gly Ser Gly Gly Gly Gly Ser Gly Gly Gly Gly
        115                 120                 125

Ser Ser Tyr Val Leu Thr Gln Pro Pro Ser Val Ser Gly Ser Pro Gly
    130                 135                 140

Gln Ser Ile Thr Ile Ser Cys Thr Gly Thr Ser Ser Asp Val Gly Gly
145                 150                 155                 160

Tyr Asn Tyr Val Ser Trp Tyr Gln Gln His Pro Gly Lys Ala Pro Lys
                165                 170                 175

Leu Met Ile Tyr Glu Gly Ser Lys Arg Pro Ser Gly Val Ser Asn Arg
            180                 185                 190

Phe Ser Gly Ser Lys Ser Gly Asn Thr Ala Ser Leu Thr Ile Ser Gly
        195                 200                 205

Leu Gln Ala Glu Asp Glu Ala Asp Tyr Tyr Cys Ser Ser Tyr Thr Thr
    210                 215                 220

Arg Ser Thr Arg Val Phe Gly Gly Gly Thr Lys Leu Thr Val Leu Gly
225                 230                 235                 240

Gly Gly Gly Ser Gly Gly Gly Gly Ser Gly Gly Gly Ser Gln Val
                245                 250                 255

Gln Leu Gln Gln Ser Gly Pro Gly Leu Val Lys Pro Ser Glu Thr Leu
            260                 265                 270

Ser Leu Thr Cys Thr Val Ser Gly Asp Ser Ile Ser Ser Tyr Tyr Trp
        275                 280                 285

Ser Trp Ile Arg Gln Pro Pro Gly Lys Gly Leu Glu Trp Ile Gly Tyr
```

```
                    290                 295                 300
Ile Tyr Tyr Ser Gly Ser Thr Asn Tyr Asn Pro Ser Leu Lys Ser Arg
305                 310                 315                 320

Val Thr Ile Ser Val Asp Thr Ser Lys Ser Gln Phe Ser Leu Lys Leu
                325                 330                 335

Ser Ser Val Thr Ala Ala Asp Thr Ala Val Tyr Tyr Cys Ala Arg Gly
                340                 345                 350

Arg Tyr Phe Asp Val Trp Gly Arg Gly Thr Met Val Thr Val Ser Ser
                355                 360                 365

Gly Gly Gly Gly Ser Gly Gly Gly Ser Gly Gly Gly Gly Ser Ser
370                 375                 380

Tyr Val Leu Thr Gln Pro Ser Val Ser Gly Ser Pro Gly Gln Ser
385                 390                 395                 400

Ile Thr Ile Ser Cys Thr Gly Thr Ser Ser Asp Val Gly Gly Tyr Asn
                405                 410                 415

Tyr Val Ser Trp Tyr Gln Gln His Pro Gly Lys Ala Pro Lys Leu Met
                420                 425                 430

Ile Tyr Glu Gly Ser Lys Arg Pro Ser Gly Val Ser Asn Arg Phe Ser
                435                 440                 445

Gly Ser Lys Ser Gly Asn Thr Ala Ser Leu Thr Ile Ser Gly Leu Gln
                450                 455                 460

Ala Glu Asp Glu Ala Asp Tyr Tyr Cys Ser Ser Tyr Thr Thr Arg Ser
465                 470                 475                 480

Thr Arg Val Phe Gly Gly Gly Thr Lys Leu Thr Val Leu Asp Tyr Lys
                485                 490                 495

Asp Asp Asp Asp Lys
                500

<210> SEQ ID NO 4
<211> LENGTH: 495
<212> TYPE: PRT
<213> ORGANISM: Mus musculus
<220> FEATURE:
<223> OTHER INFORMATION: An artificially synthesized scFv sequence

<400> SEQUENCE: 4

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
                20                  25                  30

Phe Ile His Trp Val Lys Gln Arg Pro Gly Gln Gly Leu Glu Trp Ile
                35                  40                  45

Gly Trp Ile Phe Pro Gly Asp Asp Thr Thr Asp Tyr Asn Glu Lys Phe
            50                  55                  60

Arg Gly Lys Thr Thr Leu Thr Ala Asp Lys Ser Ser Thr Ala Tyr
65              70                  75                  80

Ile Leu Leu Ser Ser Leu Thr Ser Glu Asp Ser Ala Met Tyr Phe Cys
                85                  90                  95

Val Arg Ser Asp Asp Phe Asp Tyr Trp Gly Gln Gly Thr Thr Leu Thr
                100                 105                 110

Val Ser Ser Gly Gly Gly Gly Ser Gly Gly Gly Gly Ser Gly Gly Gly
                115                 120                 125

Gly Ser Gln Ile Val Leu Thr Gln Ser Pro Ala Ile Met Ser Ala Ser
130                 135                 140

Pro Gly Glu Lys Val Thr Ile Thr Cys Ser Ala Ser Ser Ser Val Ser
```

Tyr Met His Trp Phe Gln Gln Lys Pro Gly Thr Phe Pro Lys Leu Trp
145             150                 155                 160

Ile Tyr Ser Thr Ser Asn Leu Ala Ser Gly Val Pro Thr Arg Phe Ser
            165                 170                 175

Gly Ser Gly Ser Gly Thr Ser Tyr Ser Leu Thr Ile Ser Arg Met Glu
        180                 185                 190

Ala Glu Asp Ala Ala Thr Tyr Tyr Cys Gln Gln Arg Thr Ser Tyr Pro
    195                 200                 205

Pro Thr Phe Gly Ser Gly Thr Lys Leu Glu Ile Lys Gly Gly Gly Gly
210                 215                 220

Ser Gly Gly Gly Gly Ser Gly Gly Gly Ser Gln Val Gln Leu Gln
225                 230                 235                 240

Gln Ser Gly Pro Glu Leu Val Lys Pro Gly Ala Ser Val Lys Met Ser
        245                 250                 255

Cys Lys Ala Ser Gly Tyr Thr Phe Thr Asp Tyr Phe Ile His Trp Val
    260                 265                 270

Lys Gln Arg Pro Gly Gln Gly Leu Glu Trp Ile Gly Trp Ile Phe Pro
275                 280                 285

Gly Asp Asp Thr Thr Asp Tyr Asn Glu Lys Phe Arg Gly Lys Thr Thr
    290                 295                 300

Leu Thr Ala Asp Lys Ser Ser Thr Ala Tyr Ile Leu Leu Ser Ser
305                 310                 315                 320

Leu Thr Ser Glu Asp Ser Ala Met Tyr Phe Cys Val Arg Ser Asp Asp
        325                 330                 335

Phe Asp Tyr Trp Gly Gln Gly Thr Thr Leu Thr Val Ser Ser Gly Gly
    340                 345                 350

Gly Gly Ser Gly Gly Gly Ser Gly Gly Gly Ser Gln Ile Val
355                 360                 365

Leu Thr Gln Ser Pro Ala Ile Met Ser Ala Ser Pro Gly Glu Lys Val
370                 375                 380

Thr Ile Thr Cys Ser Ala Ser Ser Ser Val Ser Tyr Met His Trp Phe
385                 390                 395                 400

Gln Gln Lys Pro Gly Thr Phe Pro Lys Leu Trp Ile Tyr Ser Thr Ser
        405                 410                 415

Asn Leu Ala Ser Gly Val Pro Thr Arg Phe Ser Gly Ser Gly Ser Gly
    420                 425                 430

Thr Ser Tyr Ser Leu Thr Ile Ser Arg Met Glu Ala Glu Asp Ala Ala
435                 440                 445

Thr Tyr Tyr Cys Gln Gln Arg Thr Ser Tyr Pro Pro Thr Phe Gly Ser
465                 470                 475                 480

Gly Thr Lys Leu Glu Ile Lys Asp Tyr Lys Asp Asp Asp Lys
        485                 490                 495

<210> SEQ ID NO 5
<211> LENGTH: 449
<212> TYPE: PRT
<213> ORGANISM: Homo sapiens
<220> FEATURE:

<400> SEQUENCE: 5

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
            35                  40                  45
Ile Gly Tyr Ile Ser Tyr Ser Gly Ile Thr Thr Tyr Asn Pro Ser Leu
 50                  55                  60
Lys Ser Arg Val Thr Met Leu Arg Asp Thr Ser Lys Asn Gln Phe Ser
 65                  70                  75                  80
Leu Arg Leu Ser Ser Val Thr Ala Ala Asp Thr Ala Val Tyr Tyr Cys
                 85                  90                  95
Ala Arg Ser Leu Ala Arg Thr Thr Ala Met Asp Tyr Trp Gly Gln Gly
            100                 105                 110
Ser Leu Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
            130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
            195                 200                 205
Ser Asn Thr Lys Val Asp Lys Lys Val Glu Pro Lys Ser Cys Asp Lys
210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Asn Ser Thr Tyr Arg Val
            290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
            355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
            435                 440                 445

Lys

```
<210> SEQ ID NO 6
<211> LENGTH: 94
<212> TYPE: PRT
<213> ORGANISM: Homo sapiens
<220> FEATURE:

<400> SEQUENCE: 6
```

| Asp | Ile | Gln | Met | Thr | Gln | Ser | Pro | Ser | Ser | Leu | Ser | Ala | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Thr | Thr | Ser | Arg | Leu | His | Ser | Gly | Val | Pro | Ser | Arg | Phe |
|---|---|---|---|---|---|---|---|---|---|---|---|---|---|---|---|
| | | | 20 | | | | | 25 | | | | | 30 | | |

| Ser | Gly | Ser | Gly | Ser | Gly | Thr | Asp | Gly | Thr | Lys | Val | Glu | Ile | Lys | Arg |
|---|---|---|---|---|---|---|---|---|---|---|---|---|---|---|---|
| | | 35 | | | | | 40 | | | | | 45 | | | |

| Thr | Val | Ala | Ala | Pro | Ser | Val | Phe | Ile | Phe | Pro | Pro | Asp | Asn | Ala | Leu |
|---|---|---|---|---|---|---|---|---|---|---|---|---|---|---|---|
| | 50 | | | | | 55 | | | | | 60 | | | | |

| Gln | Ser | Gly | Asn | Ser | Gln | Glu | Ser | Val | Thr | Glu | Gln | Asp | Ser | Lys | Asp |
|---|---|---|---|---|---|---|---|---|---|---|---|---|---|---|---|
| 65 | | | | | 70 | | | | | 75 | | | | | 80 |

| Leu | Ser | Ser | Pro | Val | Thr | Lys | Ser | Phe | Asn | Arg | Gly | Glu | Cys |
|---|---|---|---|---|---|---|---|---|---|---|---|---|---|
| | | | | 85 | | | | | 90 | | | | |

```
<210> SEQ ID NO 7
<211> LENGTH: 1924
<212> TYPE: DNA
<213> ORGANISM: Macaca fascicularis
<220> FEATURE:
<221> NAME/KEY: CDS
<222> LOCATION: (11)..(1918)

<400> SEQUENCE: 7
```

```
gaattccacc atg ccc tcc tgg gcc ctc ttc atg gtc acc tcc tgc ctc        49
            Met Pro Ser Trp Ala Leu Phe Met Val Thr Ser Cys Leu
              1               5                  10 ctc ctg gcc cct caa aac ctg gcc caa gtc agc agc caa gat gtc tcc        97
Leu Leu Ala Pro Gln Asn Leu Ala Gln Val Ser Ser Gln Asp Val Ser
         15                  20                  25 ttg ctg gcc tcg gac tca gag ccc ctg aag tgt ttc tcc cga aca ttt       145
Leu Leu Ala Ser Asp Ser Glu Pro Leu Lys Cys Phe Ser Arg Thr Phe
 30                  35                  40                  45 gag gac ctc act tgc ttc tgg gat gag gaa gag gca gca ccc agt ggg       193
Glu Asp Leu Thr Cys Phe Trp Asp Glu Glu Glu Ala Ala Pro Ser Gly
                 50                  55                  60 aca tac cag ctg ctg tat gcc tac ccg ggg gag aag ccc cgt gcc tgc       241
Thr Tyr Gln Leu Leu Tyr Ala Tyr Pro Gly Glu Lys Pro Arg Ala Cys
             65                  70                  75 ccc ctg agt tct cag agc gtg ccc cgc ttt gga acc cga tac gtg tgc       289
Pro Leu Ser Ser Gln Ser Val Pro Arg Phe Gly Thr Arg Tyr Val Cys
         80                  85                  90 cag ttt cca gcc cag gaa gaa gtg cgt ctc ttc tct ccg ctg cac ctc       337
Gln Phe Pro Ala Gln Glu Glu Val Arg Leu Phe Ser Pro Leu His Leu
     95                 100                 105 tgg gtg aag aat gtg ttc cta aac cag act cag att cag cga gtc ctc       385
Trp Val Lys Asn Val Phe Leu Asn Gln Thr Gln Ile Gln Arg Val Leu
110                 115                 120                 125 ttt gtg gac agt gta ggc ctg ccg gct ccc ccc agt atc atc aag gcc       433
Phe Val Asp Ser Val Gly Leu Pro Ala Pro Pro Ser Ile Ile Lys Ala
                130                 135                 140 atg ggt ggg agc cag cca ggg gaa ctt cag atc agc tgg gag gcc cca       481
Met Gly Gly Ser Gln Pro Gly Glu Leu Gln Ile Ser Trp Glu Ala Pro
            145                 150                 155
```

```
gct cca gaa atc agt gat ttc ctg agg tac gaa ctc cgc tat ggc ccc      529
Ala Pro Glu Ile Ser Asp Phe Leu Arg Tyr Glu Leu Arg Tyr Gly Pro
    160             165                 170 aaa gat ctc aag aac tcc act ggt ccc acg gtc ata cag ttg atc gcc      577
Lys Asp Leu Lys Asn Ser Thr Gly Pro Thr Val Ile Gln Leu Ile Ala
175             180                 185 aca gaa acc tgc tgc cct gct ctg cag agg cca cac tca gcc tct gct      625
Thr Glu Thr Cys Cys Pro Ala Leu Gln Arg Pro His Ser Ala Ser Ala
190             195                 200                 205 ctg gac cag tct cca tgt gct cag ccc aca atg ccc tgg caa gat gga      673
Leu Asp Gln Ser Pro Cys Ala Gln Pro Thr Met Pro Trp Gln Asp Gly
            210                 215                 220 cca aag cag acc tcc cca act aga gaa gct tca gct ctg aca gca gtg      721
Pro Lys Gln Thr Ser Pro Thr Arg Glu Ala Ser Ala Leu Thr Ala Val
                225                 230                 235 ggt gga agc tgc ctc atc tca gga ctc cag cct ggc aac tcc tac tgg      769
Gly Gly Ser Cys Leu Ile Ser Gly Leu Gln Pro Gly Asn Ser Tyr Trp
        240                 245                 250 ctg cag ctg cgc agc gaa cct gat ggg atc tcc ctc ggt ggc tcc tgg      817
Leu Gln Leu Arg Ser Glu Pro Asp Gly Ile Ser Leu Gly Gly Ser Trp
255                 260                 265 gga tcc tgg tcc ctc cct gtg act gtg gac ctg cct gga gat gca gtg      865
Gly Ser Trp Ser Leu Pro Val Thr Val Asp Leu Pro Gly Asp Ala Val
270                 275                 280                 285 gca att gga ctg caa tgc ttt acc ttg gac ctg aag aat gtt acc tgt      913
Ala Ile Gly Leu Gln Cys Phe Thr Leu Asp Leu Lys Asn Val Thr Cys
            290                 295                 300 caa tgg cag caa gag gac cat gct agt tcc caa ggt ttc ttc tac cac      961
Gln Trp Gln Gln Glu Asp His Ala Ser Ser Gln Gly Phe Phe Tyr His
                305                 310                 315 agc agg gca cgg tgc tgc ccc aga gac agg tac ccc atc tgg gag gac     1009
Ser Arg Ala Arg Cys Cys Pro Arg Asp Arg Tyr Pro Ile Trp Glu Asp
        320                 325                 330 tgt gaa gag gaa gag aaa aca aat cca gga tta cag acc cca cag ttc     1057
Cys Glu Glu Glu Glu Lys Thr Asn Pro Gly Leu Gln Thr Pro Gln Phe
335                 340                 345 tct cgc tgc cac ttc aag tca cga aat gac agc gtt att cac atc ctt     1105
Ser Arg Cys His Phe Lys Ser Arg Asn Asp Ser Val Ile His Ile Leu
350                 355                 360                 365 gtg gag gtg acc aca gcc ctg ggt gct gtt cac agt tac ctg ggc tcc     1153
Val Glu Val Thr Thr Ala Leu Gly Ala Val His Ser Tyr Leu Gly Ser
            370                 375                 380 cct ttc tgg atc cac cag gct gtg cgc ctc ccc acc cca aac ttg cac     1201
Pro Phe Trp Ile His Gln Ala Val Arg Leu Pro Thr Pro Asn Leu His
                385                 390                 395 tgg agg gag atc tcc agc ggg cat ctg gaa ttg gag tgg cag cac cca     1249
Trp Arg Glu Ile Ser Ser Gly His Leu Glu Leu Glu Trp Gln His Pro
        400                 405                 410 tca tcc tgg gca gcc caa gag acc tgc tat caa ctc cga tac aca gga     1297
Ser Ser Trp Ala Ala Gln Glu Thr Cys Tyr Gln Leu Arg Tyr Thr Gly
415                 420                 425 gaa ggc cat cag gac tgg aag gtg ctg gag ccg cct ctc ggg gcc cga     1345
Glu Gly His Gln Asp Trp Lys Val Leu Glu Pro Pro Leu Gly Ala Arg
430                 435                 440                 445 gga ggg acc ctg gag ctg cgc ccg cga tct cgc tac cgt tta cag ctg     1393
Gly Gly Thr Leu Glu Leu Arg Pro Arg Ser Arg Tyr Arg Leu Gln Leu
            450                 455                 460 cgc gcc agg ctc aat ggc ccc acc tac caa ggt ccc tgg agc tcg tgg     1441
Arg Ala Arg Leu Asn Gly Pro Thr Tyr Gln Gly Pro Trp Ser Ser Trp
```

```
                    465                 470                 475
tcg gac cca gct agg gtg gag acc gcc acc gag acc gcc tgg att tcc       1489
Ser Asp Pro Ala Arg Val Glu Thr Ala Thr Glu Thr Ala Trp Ile Ser
            480                 485                 490 ttg gtg acc gct ctg ctg cta gtg ctg ggc ctc agc gcc gtc ctg ggc       1537
Leu Val Thr Ala Leu Leu Leu Val Leu Gly Leu Ser Ala Val Leu Gly
495                 500                 505 ctg ctg ctg ctg agg tgg cag ttt cct gca cac tac agg aga ctg agg       1585
Leu Leu Leu Leu Arg Trp Gln Phe Pro Ala His Tyr Arg Arg Leu Arg
510                 515                 520                 525 cat gcc ctg tgg ccc tca ctt cca gat ctg cac cga gtc cta ggc cag       1633
His Ala Leu Trp Pro Ser Leu Pro Asp Leu His Arg Val Leu Gly Gln
                530                 535                 540 tac ctt agg gac act gca gcc ctg agt ccg ccc aag gcc aca gtc tca       1681
Tyr Leu Arg Asp Thr Ala Ala Leu Ser Pro Pro Lys Ala Thr Val Ser
            545                 550                 555 gat acc tgt gaa gaa gtg gaa ccc agc ctc ctt gaa atc ctc ccc aag       1729
Asp Thr Cys Glu Glu Val Glu Pro Ser Leu Leu Glu Ile Leu Pro Lys
            560                 565                 570 tcc tca gag agg act cct ttg ccc ctg tgt tcc tcc cag tcc cag atg       1777
Ser Ser Glu Arg Thr Pro Leu Pro Leu Cys Ser Ser Gln Ser Gln Met
575                 580                 585 gac tac cga aga ttg cag cct tct tgc ctg ggg acc atg ccc ctg tct       1825
Asp Tyr Arg Arg Leu Gln Pro Ser Cys Leu Gly Thr Met Pro Leu Ser
590                 595                 600                 605 gtg tgc cca ccc atg gct gag tca ggg tcc tgc tgt acc acc cac att       1873
Val Cys Pro Pro Met Ala Glu Ser Gly Ser Cys Cys Thr Thr His Ile
                610                 615                 620 gcc aac cat tcc tac cta cca cta agc tat tgg cag cag cct tga           1918
Ala Asn His Ser Tyr Leu Pro Leu Ser Tyr Trp Gln Gln Pro
            625                 630                 635 gtcgac                                                                1924
```

<210> SEQ ID NO 8
<211> LENGTH: 24
<212> TYPE: DNA
<213> ORGANISM: Artificial
<220> FEATURE:
<223> OTHER INFORMATION: an artificially synthesized sequence

<400> SEQUENCE: 8 cagggggccag tggatagact gatg                                           24

<210> SEQ ID NO 9
<211> LENGTH: 23
<212> TYPE: DNA
<213> ORGANISM: Artificial
<220> FEATURE:
<223> OTHER INFORMATION: an artificially synthesized sequence

<400> SEQUENCE: 9
gctcactgga tggtgggaag atg                                             23

<210> SEQ ID NO 10
<211> LENGTH: 354
<212> TYPE: DNA
<213> ORGANISM: Mus musculus

<400> SEQUENCE: 10
caggttcagc tgcagcagtc tggacctgag ctggtgaagc ctggggcctc agtgaagatt     60
tcctgcaagg cttctggcta tgcattcact aactcctgga tgaactgggt gaagcagagg    120

```
cctggaaagg gtcttgagtg gattggacgg atttatcctg gagatggaga aactatctac      180
aatgggaaat tcagggtcaa ggccacactg actgcagaca atcctccag cacagcctac       240 atggatatca gcagcctgac atctgaggac tctgcggtct acttctgtgc aagaggctat      300
gatgattact cgtttgctta ctggggccaa gggactctgg tcactgtctc tgca            354
```

<210> SEQ ID NO 11
<211> LENGTH: 118
<212> TYPE: PRT
<213> ORGANISM: Mus musculus

<400> SEQUENCE: 11

```
Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Thr Asn Ser
            20                  25                  30

Trp Met Asn Trp Val Lys Gln Arg Pro Gly Lys Gly Leu Glu Trp Ile
        35                  40                  45

Gly Arg Ile Tyr Pro Gly Asp Gly Glu Thr Ile Tyr Asn Gly Lys Phe
    50                  55                  60

Arg Val Lys Ala Thr Leu Thr Ala Asp Lys Ser Ser Thr Ala Tyr
65                  70                  75                  80

Met Asp Ile Ser Ser Leu Thr Ser Glu Asp Ser Ala Val Tyr Phe Cys
                85                  90                  95

Ala Arg Gly Tyr Asp Asp Tyr Ser Phe Ala Tyr Trp Gly Gln Gly Thr
            100                 105                 110

Leu Val Thr Val Ser Ala
        115
```

<210> SEQ ID NO 12
<211> LENGTH: 336
<212> TYPE: DNA
<213> ORGANISM: Mus musculus

<400> SEQUENCE: 12

```
gatattgtga tgactcaggc tgcaccctct atacctgtca ctcctggaga gtcagtatcc      60
atctcctgta ggtctagtaa gagtctcctg catagtaatg caacacttac cttgtattgg      120
ttcctgcaga ggccaggcca gtctcctcaa ctcctgatat atcggatgtc caaccttgcc      180
tcaggagtcc cagataggtt cagtggcagt gggtcaggaa ctgctttcac actgagaatc      240
agtagagtga aggctgagga tgtgggtgtt tattactgta tgcaacatat agaatatcct      300
tttacgttcg gatcggggac caagctggaa ataaaa                                336
```

<210> SEQ ID NO 13
<211> LENGTH: 112
<212> TYPE: PRT
<213> ORGANISM: Mus musculus

<400> SEQUENCE: 13

```
Asp Ile Val Met Thr Gln Ala Ala Pro Ser Ile Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
```

```
                   50                   55                  60
Asp Arg Phe Ser Gly Ser Gly Ser Gly Thr Ala Phe Thr Leu Arg Ile
 65                  70                  75                  80

Ser Arg Val Glu Ala Glu Asp Val Gly Val Tyr Tyr Cys Met Gln His
                 85                  90                  95

Ile Glu Tyr Pro Phe Thr Phe Gly Ser Gly Thr Lys Leu Glu Ile Lys
            100                 105                 110

<210> SEQ ID NO 14
<211> LENGTH: 30
<212> TYPE: DNA
<213> ORGANISM: Artificial
<220> FEATURE:
<223> OTHER INFORMATION: an artificially synthesized primer sequence

<400> SEQUENCE: 14
tagaattcca ccatggaatg gcctttgatc                                   30

<210> SEQ ID NO 15
<211> LENGTH: 56
<212> TYPE: DNA
<213> ORGANISM: Artificial
<220> FEATURE:
<223> OTHER INFORMATION: an artificially synthesized primer sequence

<400> SEQUENCE: 15
agcctgagtc atcacaatat ccgatccgcc tccacctgca gagacagtga ccagag      56

<210> SEQ ID NO 16
<211> LENGTH: 56
<212> TYPE: DNA
<213> ORGANISM: Artificial
<220> FEATURE:
<223> OTHER INFORMATION: an artificially synthesized primer sequence

<400> SEQUENCE: 16
actctggtca ctgtctctgc aggtggaggc ggatcggata ttgtgatgac tcaggc      56

<210> SEQ ID NO 17
<211> LENGTH: 60
<212> TYPE: DNA
<213> ORGANISM: Artificial
<220> FEATURE:
<223> OTHER INFORMATION: an artificially synthesized primer sequence

<400> SEQUENCE: 17
attgcggccg cttatcactt atcgtcgtca tccttgtagt cttttatttc cagcttggtc  60

<210> SEQ ID NO 18
<211> LENGTH: 8
<212> TYPE: PRT
<213> ORGANISM: Artificial
<220> FEATURE:
<223> OTHER INFORMATION: an artificially synthesized FLAG tag sequence

<400> SEQUENCE: 18

Asp Tyr Lys Asp Asp Asp Asp Lys
 1               5

<210> SEQ ID NO 19
<211> LENGTH: 85
<212> TYPE: DNA
<213> ORGANISM: Artificial
<220> FEATURE:
<223> OTHER INFORMATION: an artificially synthesized primer sequence
```

```
<400> SEQUENCE: 19
tagaattcca ccatggaatg gcctttgatc tttctcttcc tcctgtcagg aactgcaggt      60
gtccactccc aggttcagct gcagc                                            85

<210> SEQ ID NO 20
<211> LENGTH: 82
<212> TYPE: DNA
<213> ORGANISM: Artificial
<220> FEATURE:
<223> OTHER INFORMATION: an artificially synthesized primer sequence

<400> SEQUENCE: 20
tggtcactgt ctctgcaggt ggtggtggtt cgggtggtgg tggttcgggt ggtggcggat      60
cggatattgt gatgactcag gc                                               82

<210> SEQ ID NO 21
<211> LENGTH: 82
<212> TYPE: DNA
<213> ORGANISM: Artificial
<220> FEATURE:
<223> OTHER INFORMATION: an artificially synthesized primer sequence

<400> SEQUENCE: 21
tgagtcatca caatatccga tccgccacca cccgaaccac caccacccga accaccacca      60
cctgcagaga cagtgaccag ag                                               82

<210> SEQ ID NO 22
<211> LENGTH: 25
<212> TYPE: DNA
<213> ORGANISM: Artificial
<220> FEATURE:
<223> OTHER INFORMATION: an artificially synthesized primer sequence

<400> SEQUENCE: 22
caggttcagc tgcagcagtc tggac                                            25

<210> SEQ ID NO 23
<211> LENGTH: 81
<212> TYPE: DNA
<213> ORGANISM: Artificial
<220> FEATURE:
<223> OTHER INFORMATION: an artificially synthesized primer sequence

<400> SEQUENCE: 23
gctgcagctg aacctgcgat ccaccgcctc ccgaaccacc accaccgat ccaccacctc       60 cttttatttc cagcttggtc c                                                81

<210> SEQ ID NO 24
<211> LENGTH: 1572
<212> TYPE: DNA
<213> ORGANISM: Homo sapiens

<400> SEQUENCE: 24
atggactgga cctggaggtt cctctttgtg gtggcagcag ctacaggtgt ccagtcccag      60
gtgcagctgg tgcagtctgg acctgaggtg aagaagcctg ggcctcagt gaaggtctcc     120 tgcaaggctt ctggatacac cttcaccaac tcctggatga actgggtgag gcagaggcct    180
ggaaagggtc ttgagtggat gggacggatt tatcctggag atggagaaac tatctacaat    240
gggaaattca gggtcagagt cacgattacc gcggacgaat ccacgagcac agcctacatg    300
```

```
gagctgagca gcctgagatc tgaggacacg gccgtgtatt actgtgcgag aggctatgat    360
gattactcgt ttgcttactg gggccaggga accacggtca ccgtctcttc aggtggtggt    420
ggatccggag gtggtggatc gggtggtgga ggatcggata ttgtgatgac tcagtctgca    480
ctctcccctg ccgtcacccc tggagagccg gcctccatct cctgcaggtc tagtaagagt    540
ctcctgcata gtaatggcaa cacttacttg tattggttcc agcagaagcc agggcagtct    600
ccacagctcc tgatctatcg gatgtccaac cttgcctcag ggtccctga caggttcagt     660
ggcagtggat caggcacagc ttttacactg aaaatcagca gagtggaggc tgaggatgtt    720
ggggtttatt actgcatgca acatatagaa tatcctttta cgttcggcca agggaccaaa    780
ctggaaatca aggaggtgg tggatcgggt ggtggtggtt cggaggcgg tggatcgcag       840
gtgcagctgg tgcagtctgg acctgaggtg aagaagcctg gggcctcagt gaaggtctcc    900
tgcaaggctt ctggatacac cttcaccaac tcctggatga ctgggtgag gcagaggcct     960
ggaaagggtc ttgagtggat gggacggatt tatcctggag atggagaaac tatctacaat   1020
gggaaattca gggtcagagt cacgattacc gcggacgaat ccacgagcac agcctacatg   1080
gagctgagca gcctgagatc tgaggacacg gccgtgtatt actgtgcgag aggctatgat   1140
gattactcgt ttgcttactg gggccaggga accacggtca ccgtctcttc aggtggtggt   1200
ggatccggag gtggtggatc gggtggtgga ggatcggata ttgtgatgac tcagtctgca   1260
ctctcccctg ccgtcacccc tggagagccg gcctccatct cctgcaggtc tagtaagagt   1320
ctcctgcata gtaatggcaa cacttacttg tattggttcc agcagaagcc agggcagtct   1380
ccacagctcc tgatctatcg gatgtccaac cttgcctcag ggtccctga caggttcagt    1440
ggcagtggat caggcacagc ttttacactg aaaatcagca gagtggaggc tgaggatgtt   1500
ggggtttatt actgcatgca acatatagaa tatcctttta cgttcggcca agggaccaaa   1560
ctggaaatca aa                                                        1572
```

<210> SEQ ID NO 25
<211> LENGTH: 524
<212> TYPE: PRT
<213> ORGANISM: Homo sapiens

<400> SEQUENCE: 25

```
Met Asp Trp Thr Trp Arg Phe Leu Phe Val Val Ala Ala Ala Thr Gly
1               5                   10                  15

Val Gln Ser Gln Val Gln Leu Val Gln Ser Gly Pro Glu Val Lys Lys
            20                  25                  30

Pro Gly Ala Ser Val Lys Val Ser Cys Lys Ala Ser Gly Tyr Thr Phe
        35                  40                  45

Thr Asn Ser Trp Met Asn Trp Val Arg Gln Arg Pro Gly Lys Gly Leu
    50                  55                  60

Glu Trp Met Gly Arg Ile Tyr Pro Gly Asp Gly Glu Thr Ile Tyr Asn
65                  70                  75                  80

Gly Lys Phe Arg Val Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Tyr Asp Asp Tyr Ser Phe Ala Tyr Trp Gly
        115                 120                 125

Gln Gly Thr Thr Val Thr Val Ser Ser Gly Gly Gly Gly Ser Gly Gly
    130                 135                 140
```

Gly Gly Ser Gly Gly Gly Ser Asp Ile Val Met Thr Gln Ser Ala
145                 150                 155                 160

Leu Ser Leu Pro Val Thr Pro Gly Glu Pro Ala Ser Ile Ser Cys Arg
            165                 170                 175

Ser Ser Lys Ser Leu Leu His Ser Asn Gly Asn Thr Tyr Leu Tyr Trp
        180                 185                 190

Phe Gln Gln Lys Pro Gly Gln Ser Pro Gln Leu Leu Ile Tyr Arg Met
        195                 200                 205

Ser Asn Leu Ala Ser Gly Val Pro Asp Arg Phe Ser Gly Ser Gly Ser
        210                 215                 220

Gly Thr Ala Phe Thr Leu Lys Ile Ser Arg Val Glu Ala Glu Asp Val
225                 230                 235                 240

Gly Val Tyr Tyr Cys Met Gln His Ile Glu Tyr Pro Phe Thr Phe Gly
                245                 250                 255

Gln Gly Thr Lys Leu Glu Ile Lys Gly Gly Gly Ser Gly Gly Gly
        260                 265                 270

Gly Ser Gly Gly Gly Gly Ser Gln Val Gln Leu Val Gln Ser Gly Pro
        275                 280                 285

Glu Val Lys Lys Pro Gly Ala Ser Val Lys Val Ser Cys Lys Ala Ser
290                 295                 300

Gly Tyr Thr Phe Thr Asn Ser Trp Met Asn Trp Val Arg Gln Arg Pro
305                 310                 315                 320

Gly Lys Gly Leu Glu Trp Met Gly Arg Ile Tyr Pro Gly Asp Gly Glu
                325                 330                 335

Thr Ile Tyr Asn Gly Lys Phe Arg Val Arg Val Thr Ile Thr Ala Asp
                340                 345                 350

Glu Ser Thr Ser Thr Ala Tyr Met Glu Leu Ser Ser Leu Arg Ser Glu
        355                 360                 365

Asp Thr Ala Val Tyr Tyr Cys Ala Arg Gly Tyr Asp Asp Tyr Ser Phe
        370                 375                 380

Ala Tyr Trp Gly Gln Gly Thr Thr Val Thr Val Ser Ser Gly Gly Gly
385                 390                 395                 400

Gly Ser Gly Gly Gly Gly Ser Gly Gly Gly Gly Ser Asp Ile Val Met
                405                 410                 415

Thr Gln Ser Ala Leu Ser Leu Pro Val Thr Pro Gly Glu Pro Ala Ser
            420                 425                 430

Ile Ser Cys Arg Ser Ser Lys Ser Leu Leu His Ser Asn Gly Asn Thr
        435                 440                 445

Tyr Leu Tyr Trp Phe Gln Gln Lys Pro Gly Gln Ser Pro Gln Leu Leu
        450                 455                 460

Ile Tyr Arg Met Ser Asn Leu Ala Ser Gly Val Pro Asp Arg Phe Ser
465                 470                 475                 480

Gly Ser Gly Ser Gly Thr Ala Phe Thr Leu Lys Ile Ser Arg Val Glu
                485                 490                 495

Ala Glu Asp Val Gly Val Tyr Tyr Cys Met Gln His Ile Glu Tyr Pro
            500                 505                 510

Phe Thr Phe Gly Gln Gly Thr Lys Leu Glu Ile Lys
        515                 520

<210> SEQ ID NO 26
<211> LENGTH: 1572
<212> TYPE: DNA
<213> ORGANISM: Homo sapiens

<400> SEQUENCE: 26

-continued

```
atggactgga cctggaggtt cctctttgtg gtggcagcag ctacaggtgt ccagtcccag      60
gtgcagctgg tgcagtctgg acctgaggtg aagaagcctg ggcctcagt gaaggtctcc     120
tgcaaggctt ctggatacac cttcaccaac tcctggatga actgggtgag cagaggcct     180
ggaaagggtc ttgagtgggt tggacggatt tatcctggag atggagaaac tatctacaat    240
gggaaattca gggtcagagt cacgattacc gcggacgaat ccacgagcac agcctacatg    300
gagctgagca gcctgagatc tgaggacacg gccgtgtatt actgtgcgag aggctatgat    360
gattactcgt ttgcttactg gggccaggga accacggtca ccgtctcttc aggtggtggt    420
ggatccggag gtggtggatc gggtggtgga ggatcggata ttgtgatgac tcagtctgca    480
ctctccctgc ccgtcacccc tggagagccg gcctccatct cctgcaggtc tagtaagagt    540
ctcctgcata gtaatggcaa cacttacttg tattggtacc tgcagaagcc agggcagtct    600
ccacagctcc tgatctatcg gatgtccaac cttgcctcag ggtccctga caggttcagt    660
ggcagtggat caggcacagc ttttacactg aaaatcagca gagtggaggc tgaggatgtt    720
ggggtttatt actgcatgca acatatagaa tatccttta cgttcggcca agggaccaaa    780
ctggaaatca aggaggtgg tggatcgggt ggtggtggtt cggaggcgg tggatcgcag    840
gtgcagctgg tgcagtctgg acctgaggtg aagaagcctg ggcctcagt gaaggtctcc    900
tgcaaggctt ctggatacac cttcaccaac tcctggatga actgggtgag cagaggcct    960
ggaaagggtc ttgagtgggt tggacggatt tatcctggag atggagaaac tatctacaat   1020
gggaaattca gggtcagagt cacgattacc gcggacgaat ccacgagcac agcctacatg   1080
gagctgagca gcctgagatc tgaggacacg gccgtgtatt actgtgcgag aggctatgat   1140
gattactcgt ttgcttactg gggccaggga accacggtca ccgtctcttc aggtggtggt   1200
ggatccggag gtggtggatc gggtggtgga ggatcggata ttgtgatgac tcagtctgca   1260
ctctccctgc ccgtcacccc tggagagccg gcctccatct cctgcaggtc tagtaagagt   1320
ctcctgcata gtaatggcaa cacttacttg tattggtacc tgcagaagcc agggcagtct   1380
ccacagctcc tgatctatcg gatgtccaac cttgcctcag ggtccctga caggttcagt   1440
ggcagtggat caggcacagc ttttacactg aaaatcagca gagtggaggc tgaggatgtt   1500
ggggtttatt actgcatgca acatatagaa tatccttta cgttcggcca agggaccaaa   1560
ctggaaatca aa                                                        1572
```

<210> SEQ ID NO 27
<211> LENGTH: 524
<212> TYPE: PRT
<213> ORGANISM: Homo sapiens

<400> SEQUENCE: 27

Met Asp Trp Thr Trp Arg Phe Leu Phe Val Val Ala Ala Ala Thr Gly
1               5                   10                  15

Val Gln Ser Gln Val Gln Leu Val Gln Ser Gly Pro Glu Val Lys Lys
            20                  25                  30

Pro Gly Ala Ser Val Lys Val Ser Cys Lys Ala Ser Gly Tyr Thr Phe
        35                  40                  45

Thr Asn Ser Trp Met Asn Trp Val Arg Gln Arg Pro Gly Lys Gly Leu
    50                  55                  60

Glu Trp Val Gly Arg Ile Tyr Pro Gly Asp Gly Glu Thr Ile Tyr Asn
65                  70                  75                  80

Gly Lys Phe Arg Val Arg Val Thr Ile Thr Ala Asp Glu Ser Thr Ser

```
                      85                  90                  95
Thr Ala Tyr Met Glu Leu Ser Ser Leu Arg Ser Glu Asp Thr Ala Val
                 100                 105                 110

Tyr Tyr Cys Ala Arg Gly Tyr Asp Asp Tyr Ser Phe Ala Tyr Trp Gly
             115                 120                 125

Gln Gly Thr Thr Val Thr Val Ser Ser Gly Gly Gly Ser Gly Gly
         130                 135                 140

Gly Gly Ser Gly Gly Gly Ser Asp Ile Val Met Thr Gln Ser Ala
145                 150                 155                 160

Leu Ser Leu Pro Val Thr Pro Gly Glu Pro Ala Ser Ile Ser Cys Arg
                 165                 170                 175

Ser Ser Lys Ser Leu Leu His Ser Asn Gly Asn Thr Tyr Leu Tyr Trp
             180                 185                 190

Tyr Leu Gln Lys Pro Gly Gln Ser Pro Gln Leu Leu Ile Tyr Arg Met
         195                 200                 205

Ser Asn Leu Ala Ser Gly Val Pro Asp Arg Phe Ser Gly Ser Gly Ser
210                 215                 220

Gly Thr Ala Phe Thr Leu Lys Ile Ser Arg Val Glu Ala Glu Asp Val
225                 230                 235                 240

Gly Val Tyr Tyr Cys Met Gln His Ile Glu Tyr Pro Phe Thr Phe Gly
                 245                 250                 255

Gln Gly Thr Lys Leu Glu Ile Lys Gly Gly Gly Gly Ser Gly Gly Gly
             260                 265                 270

Gly Ser Gly Gly Gly Gly Ser Gln Val Gln Leu Val Gln Ser Gly Pro
         275                 280                 285

Glu Val Lys Lys Pro Gly Ala Ser Val Lys Val Ser Cys Lys Ala Ser
    290                 295                 300

Gly Tyr Thr Phe Thr Asn Ser Trp Met Asn Trp Val Arg Gln Arg Pro
305                 310                 315                 320

Gly Lys Gly Leu Glu Trp Val Gly Arg Ile Tyr Pro Gly Asp Gly Glu
                 325                 330                 335

Thr Ile Tyr Asn Gly Lys Phe Arg Val Arg Val Thr Ile Thr Ala Asp
             340                 345                 350

Glu Ser Thr Ser Thr Ala Tyr Met Glu Leu Ser Ser Leu Arg Ser Glu
         355                 360                 365

Asp Thr Ala Val Tyr Tyr Cys Ala Arg Gly Tyr Asp Asp Tyr Ser Phe
    370                 375                 380

Ala Tyr Trp Gly Gln Gly Thr Thr Val Thr Val Ser Ser Gly Gly Gly
385                 390                 395                 400

Gly Ser Gly Gly Gly Gly Ser Gly Gly Gly Gly Ser Asp Ile Val Met
                 405                 410                 415

Thr Gln Ser Ala Leu Ser Leu Pro Val Thr Pro Gly Glu Pro Ala Ser
             420                 425                 430

Ile Ser Cys Arg Ser Ser Lys Ser Leu Leu His Ser Asn Gly Asn Thr
         435                 440                 445

Tyr Leu Tyr Trp Tyr Leu Gln Lys Pro Gly Gln Ser Pro Gln Leu Leu
    450                 455                 460

Ile Tyr Arg Met Ser Asn Leu Ala Ser Gly Val Pro Asp Arg Phe Ser
465                 470                 475                 480

Gly Ser Gly Ser Gly Thr Ala Phe Thr Leu Lys Ile Ser Arg Val Glu
                 485                 490                 495

Ala Glu Asp Val Gly Val Tyr Tyr Cys Met Gln His Ile Glu Tyr Pro
             500                 505                 510
```

```
Phe Thr Phe Gly Gln Gly Thr Lys Leu Glu Ile Lys
        515                 520

<210> SEQ ID NO 28
<211> LENGTH: 1572
<212> TYPE: DNA
<213> ORGANISM: Homo sapiens

<400> SEQUENCE: 28
atggactgga cctggaggtt cctctttgtg gtggcagcag ctacaggtgt ccagtcccag     60
gtgcagctgg tgcagtctgg acctgaggtg aagaagcctg ggcctcagt gaaggtctcc    120
tgcaaggctt ctggatacac cttcaccaac tcctggatga actggatcag gcagaggcct    180
ggaaagggtc ttgagtggat tggacggatt tatcctggag atggagaaac tatctacaat    240
gggaaattca gggtcagagt cacgattacc gcggacgaat ccacgagcac agcctacatg    300
gagctgagca gcctgagatc tgaggacacg gccgtgtatt actgtgcgag aggctatgat    360
gattactcgt ttgcttactg gggccaggga accctggtca ccgtctcttc aggtggtggt    420
ggatccggag gtggtggatc gggtggtgga ggatcggata ttgtgatgac tcagtctgca    480
ctctccctgc ccgtcacccc tggagagccg gcctccatct cctgcaggtc tagtaagagt    540
ctcctgcata gtaatggcaa cacttacttg tattggtacc tgcagaagcc agggcagtct    600
ccacagctcc tgatctatcg gatgtccaac cttgcctcag ggtccctga caggttcagt    660
ggcagtggat caggcacagc ttttacactg aaaatcagca gagtggaggc tgaggatgtt    720
ggggtttatt actgcatgca acatatagaa atccttttta cgttcggcca agggaccaaa    780
ctggaaatca aggaggtgg tggatcgggt ggtggtggtt cgggaggcgg tggatcgcag    840
gtgcagctgg tgcagtctgg acctgaggtg aagaagcctg ggcctcagt gaaggtctcc    900
tgcaaggctt ctggatacac cttcaccaac tcctggatga actggatcag gcagaggcct    960
ggaaagggtc ttgagtggat tggacggatt tatcctggag atggagaaac tatctacaat   1020
gggaaattca gggtcagagt cacgattacc gcggacgaat ccacgagcac agcctacatg   1080
gagctgagca gcctgagatc tgaggacacg gccgtgtatt actgtgcgag aggctatgat   1140
gattactcgt ttgcttactg gggccaggga accctggtca ccgtctcttc aggtggtggt   1200
ggatccggag gtggtggatc gggtggtgga ggatcggata ttgtgatgac tcagtctgca   1260
ctctccctgc ccgtcacccc tggagagccg gcctccatct cctgcaggtc tagtaagagt   1320
ctcctgcata gtaatggcaa cacttacttg tattggtacc tgcagaagcc agggcagtct   1380
ccacagctcc tgatctatcg gatgtccaac cttgcctcag ggtccctga caggttcagt   1440
ggcagtggat caggcacagc ttttacactg aaaatcagca gagtggaggc tgaggatgtt   1500
ggggtttatt actgcatgca acatatagaa atccttttta cgttcggcca agggaccaaa   1560
ctggaaatca aa                                                        1572

<210> SEQ ID NO 29
<211> LENGTH: 524
<212> TYPE: PRT
<213> ORGANISM: Homo sapiens

<400> SEQUENCE: 29

Met Asp Trp Thr Trp Arg Phe Leu Phe Val Val Ala Ala Ala Thr Gly
1               5                   10                  15

Val Gln Ser Gln Val Gln Leu Val Gln Ser Gly Pro Glu Val Lys Lys
            20                  25                  30
```

```
Pro Gly Ala Ser Val Lys Val Ser Cys Lys Ala Ser Gly Tyr Thr Phe
            35                  40                  45

Thr Asn Ser Trp Met Asn Trp Ile Arg Gln Arg Pro Gly Lys Gly Leu
        50                  55                  60

Glu Trp Ile Gly Arg Ile Tyr Pro Gly Asp Gly Glu Thr Ile Tyr Asn
65                  70                  75                  80

Gly Lys Phe Arg Val Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Tyr Asp Asp Tyr Ser Phe Ala Tyr Trp Gly
            115                 120                 125

Gln Gly Thr Leu Val Thr Val Ser Ser Gly Gly Gly Ser Gly Gly
            130                 135                 140

Gly Gly Ser Gly Gly Gly Ser Asp Ile Val Met Thr Gln Ser Ala
145                 150                 155                 160

Leu Ser Leu Pro Val Thr Pro Gly Glu Pro Ala Ser Ile Ser Cys Arg
                165                 170                 175

Ser Ser Lys Ser Leu Leu His Ser Asn Gly Asn Thr Tyr Leu Tyr Trp
            180                 185                 190

Tyr Leu Gln Lys Pro Gly Gln Ser Pro Gln Leu Leu Ile Tyr Arg Met
            195                 200                 205

Ser Asn Leu Ala Ser Gly Val Pro Asp Arg Phe Ser Gly Ser Gly Ser
            210                 215                 220

Gly Thr Ala Phe Thr Leu Lys Ile Ser Arg Val Glu Ala Glu Asp Val
225                 230                 235                 240

Gly Val Tyr Tyr Cys Met Gln His Ile Glu Tyr Pro Phe Thr Phe Gly
                245                 250                 255

Gln Gly Thr Lys Leu Glu Ile Lys Gly Gly Gly Ser Gly Gly Gly
            260                 265                 270

Gly Ser Gly Gly Gly Gly Ser Gln Val Gln Leu Val Gln Ser Gly Pro
            275                 280                 285

Glu Val Lys Lys Pro Gly Ala Ser Val Lys Val Ser Cys Lys Ala Ser
            290                 295                 300

Gly Tyr Thr Phe Thr Asn Ser Trp Met Asn Trp Ile Arg Gln Arg Pro
305                 310                 315                 320

Gly Lys Gly Leu Glu Trp Ile Gly Arg Ile Tyr Pro Gly Asp Gly Glu
                325                 330                 335

Thr Ile Tyr Asn Gly Lys Phe Arg Val Arg Val Thr Ile Thr Ala Asp
            340                 345                 350

Glu Ser Thr Ser Thr Ala Tyr Met Glu Leu Ser Ser Leu Arg Ser Glu
            355                 360                 365

Asp Thr Ala Val Tyr Tyr Cys Ala Arg Gly Tyr Asp Asp Tyr Ser Phe
            370                 375                 380

Ala Tyr Trp Gly Gln Gly Thr Leu Val Thr Val Ser Ser Gly Gly Gly
385                 390                 395                 400

Gly Ser Gly Gly Gly Gly Ser Gly Gly Gly Gly Ser Asp Ile Val Met
                405                 410                 415

Thr Gln Ser Ala Leu Ser Leu Pro Val Thr Pro Gly Glu Pro Ala Ser
            420                 425                 430

Ile Ser Cys Arg Ser Ser Lys Ser Leu Leu His Ser Asn Gly Asn Thr
            435                 440                 445
```

```
Tyr Leu Tyr Trp Tyr Leu Gln Lys Pro Gly Gln Ser Pro Gln Leu Leu
    450                 455                 460

Ile Tyr Arg Met Ser Asn Leu Ala Ser Gly Val Pro Asp Arg Phe Ser
465                 470                 475                 480

Gly Ser Gly Ser Gly Thr Ala Phe Thr Leu Lys Ile Ser Arg Val Glu
                485                 490                 495

Ala Glu Asp Val Gly Val Tyr Tyr Cys Met Gln His Ile Glu Tyr Pro
            500                 505                 510

Phe Thr Phe Gly Gln Gly Thr Lys Leu Glu Ile Lys
        515                 520

<210> SEQ ID NO 30
<211> LENGTH: 1572
<212> TYPE: DNA
<213> ORGANISM: Homo sapiens

<400> SEQUENCE: 30
atggactgga cctggaggtt cctctttgtg gtggcagcag ctacaggtgt ccagtcccag      60
gtgcagctgg tgcagtctgg acctgaggtg aagaagcctg ggcctcagt gaaggtctcc     120
tgcaaggctt ctggatacac cttcaccaac tcctggatga actgggtgag cagaggcct     180
ggaaagggtc ttgagtggat tggacggatt tatcctggag atggagaaac tatctacaat     240
gggaaattca gggtcagagt cacgattacc gcggacgaat ccacgagcac agcctacatg     300
caactgagca gcctgagatc tgaggacacg gccgtgtatt actgtgcgag aggctatgat     360
gattactcgt ttgcttactg gggccaggga accacggtca ccgtctcttc aggtggtggt     420
ggatccggag gtggtggatc gggtggtgga ggatcggata ttgtgatgac tcagtctcca     480
ctctccctgc ccgtcacccc tggagagccg gcctccatct cctgcaggtc tagtaagagt     540
ctcctgcata gtaatggcaa cacttacttg tattggttcc tgcagaagcc agggcagtct     600
ccacagctcc tgatctatcg gatgtccaac cttgcctcag ggtccctga caggttcagt     660
ggcagtggat caggcacaga ttttacactg aaaatcagca gagtggaggc tgaggatgtt     720
ggggtttatt actgcatgca acatatagaa tatccttta cgttcggcca agggaccaaa     780
ctggaaatca aggaggtgg tggatcgggt ggtggtggtt cggaggcgg tggatcgcag     840
gtgcagctgg tgcagtctgg acctgaggtg aagaagcctg ggcctcagt gaaggtctcc     900
tgcaaggctt ctggatacac cttcaccaac tcctggatga actgggtgag cagaggcct     960
ggaaagggtc ttgagtggat tggacggatt tatcctggag atggagaaac tatctacaat    1020
gggaaattca gggtcagagt cacgattacc gcggacgaat ccacgagcac agcctacatg    1080
caactgagca gcctgagatc tgaggacacg gccgtgtatt actgtgcgag aggctatgat    1140
gattactcgt ttgcttactg gggccaggga accacggtca ccgtctcttc aggtggtggt    1200
ggatccggag gtggtggatc gggtggtgga ggatcggata ttgtgatgac tcagtctcca    1260
ctctccctgc ccgtcacccc tggagagccg gcctccatct cctgcaggtc tagtaagagt    1320
ctcctgcata gtaatggcaa cacttacttg tattggttcc tgcagaagcc agggcagtct    1380
ccacagctcc tgatctatcg gatgtccaac cttgcctcag ggtccctga caggttcagt    1440
ggcagtggat caggcacaga ttttacactg aaaatcagca gagtggaggc tgaggatgtt    1500
ggggtttatt actgcatgca acatatagaa tatccttta cgttcggcca agggaccaaa    1560
ctggaaatca aa                                                        1572

<210> SEQ ID NO 31
```

<211> LENGTH: 1572
<212> TYPE: DNA
<213> ORGANISM: Homo sapiens

<400> SEQUENCE: 31

```
atggactgga cctggaggtt cctctttgtg gtggcagcag ctacaggtgt ccagtcccag    60
gtgcagctgg tgcagtctgg acctgaggtg aagaagcctg ggcctcagt gaaggtctcc    120
tgcaaggctt ctggatacac cttcaccaac tcctggatga actgggtgag gcagaggcct   180
ggaaagggtc ttgagtggat tggacggatt tatcctggag atggagaaac tatctacaat   240
gggaaattca gggtcagagt cacgattacc gcggacgaat ccacgagcac agcctacatg   300
gagctgagca gcctgagatc tgaggacacg gccgtgtatt actgtgcgag aggctatgat   360
gattactcgt ttgcttactg gggccaggga accacggtca ccgtctcttc aggtggtggt   420
ggatccggag gtggtggatc gggtggtgga ggatcggata ttgtgatgac tcagtctcca   480
ctctccctgc ccgtcacccc tggagagccg gcctccatct cctgcaggtc tagtaagagt   540
ctcctgcata gtaatggcaa cacttacttg tattggttcc agcagaagcc agggcaggct   600
ccacggctcc tgatctatcg gatgtccaac cttgcctcag ggtccctga caggttcagt    660
ggcagtggat caggcacagc ttttacactg aaaatcagca gagtggaggc tgaggatgtt   720
ggggtttatt actgcatgca acatatagaa tatccttta cgttcggcca agggaccaaa    780
ctggaaatca aggaggtgg tggatcggt ggtggtggtt cggaggcgg tggatcgcag      840
gtgcagctgg tgcagtctgg acctgaggtg aagaagcctg ggcctcagt gaaggtctcc    900
tgcaaggctt ctggatacac cttcaccaac tcctggatga actgggtgag gcagaggcct   960
ggaaagggtc ttgagtggat tggacggatt tatcctggag atggagaaac tatctacaat  1020
gggaaattca gggtcagagt cacgattacc gcggacgaat ccacgagcac agcctacatg  1080
gagctgagca gcctgagatc tgaggacacg gccgtgtatt actgtgcgag aggctatgat  1140
gattactcgt ttgcttactg gggccaggga accacggtca ccgtctcttc aggtggtggt  1200
ggatccggag gtggtggatc gggtggtgga ggatcggata ttgtgatgac tcagtctcca  1260
ctctccctgc ccgtcacccc tggagagccg gcctccatct cctgcaggtc tagtaagagt  1320
ctcctgcata gtaatggcaa cacttacttg tattggttcc agcagaagcc agggcaggct  1380
ccacggctcc tgatctatcg gatgtccaac cttgcctcag ggtccctga caggttcagt   1440
ggcagtggat caggcacagc ttttacactg aaaatcagca gagtggaggc tgaggatgtt  1500
ggggtttatt actgcatgca acatatagaa tatccttta cgttcggcca agggaccaaa   1560
ctggaaatca aa                                                       1572
```

<210> SEQ ID NO 32
<211> LENGTH: 524
<212> TYPE: PRT
<213> ORGANISM: Homo sapiens

<400> SEQUENCE: 32

Met Asp Trp Thr Trp Arg Phe Leu Phe Val Val Ala Ala Ala Thr Gly
1               5                   10                  15

Val Gln Ser Gln Val Gln Leu Val Gln Ser Gly Pro Glu Val Lys Lys
            20                  25                  30

Pro Gly Ala Ser Val Lys Val Ser Cys Lys Ala Ser Gly Tyr Thr Phe
        35                  40                  45

Thr Asn Ser Trp Met Asn Trp Val Arg Gln Arg Pro Gly Lys Gly Leu
    50                  55                  60

-continued

Glu Trp Ile Gly Arg Ile Tyr Pro Gly Asp Gly Glu Thr Ile Tyr Asn
65                  70                  75                  80

Gly Lys Phe Arg Val Arg Val Thr Ile Thr Ala Asp Glu Ser Thr Ser
            85                  90                  95

Thr Ala Tyr Met Glu Leu Ser Ser Leu Arg Ser Glu Thr Ala Val
                100                 105                 110

Tyr Tyr Cys Ala Arg Gly Tyr Asp Asp Tyr Ser Phe Ala Tyr Trp Gly
            115                 120                 125

Gln Gly Thr Thr Val Thr Val Ser Ser Gly Gly Gly Ser Gly Gly
        130                 135                 140

Gly Gly Ser Gly Gly Gly Ser Asp Ile Val Met Thr Gln Ser Pro
145                 150                 155                 160

Leu Ser Leu Pro Val Thr Pro Gly Glu Pro Ala Ser Ile Ser Cys Arg
                165                 170                 175

Ser Ser Lys Ser Leu Leu His Ser Asn Gly Asn Thr Tyr Leu Tyr Trp
            180                 185                 190

Phe Gln Gln Lys Pro Gly Gln Ala Pro Arg Leu Leu Ile Tyr Arg Met
        195                 200                 205

Ser Asn Leu Ala Ser Gly Val Pro Asp Arg Phe Ser Gly Ser Gly Ser
210                 215                 220

Gly Thr Ala Phe Thr Leu Lys Ile Ser Arg Val Glu Ala Glu Asp Val
225                 230                 235                 240

Gly Val Tyr Tyr Cys Met Gln His Ile Glu Tyr Pro Phe Thr Phe Gly
            245                 250                 255

Gln Gly Thr Lys Leu Glu Ile Lys Gly Gly Gly Gly Ser Gly Gly Gly
        260                 265                 270

Gly Ser Gly Gly Gly Gly Ser Gln Val Gln Leu Val Gln Ser Gly Pro
    275                 280                 285

Glu Val Lys Lys Pro Gly Ala Ser Val Lys Val Ser Cys Lys Ala Ser
290                 295                 300

Gly Tyr Thr Phe Thr Asn Ser Trp Met Asn Trp Val Arg Gln Arg Pro
305                 310                 315                 320

Gly Lys Gly Leu Glu Trp Ile Gly Arg Ile Tyr Pro Gly Asp Gly Glu
            325                 330                 335

Thr Ile Tyr Asn Gly Lys Phe Arg Val Arg Val Thr Ile Thr Ala Asp
            340                 345                 350

Glu Ser Thr Ser Thr Ala Tyr Met Glu Leu Ser Ser Leu Arg Ser Glu
        355                 360                 365

Asp Thr Ala Val Tyr Tyr Cys Ala Arg Gly Tyr Asp Asp Tyr Ser Phe
    370                 375                 380

Ala Tyr Trp Gly Gln Gly Thr Thr Val Thr Val Ser Ser Gly Gly Gly
385                 390                 395                 400

Gly Ser Gly Gly Gly Gly Ser Gly Gly Gly Gly Ser Asp Ile Val Met
            405                 410                 415

Thr Gln Ser Pro Leu Ser Leu Pro Val Thr Pro Gly Glu Pro Ala Ser
            420                 425                 430

Ile Ser Cys Arg Ser Ser Lys Ser Leu Leu His Ser Asn Gly Asn Thr
        435                 440                 445

Tyr Leu Tyr Trp Phe Gln Gln Lys Pro Gly Gln Ala Pro Arg Leu Leu
    450                 455                 460

Ile Tyr Arg Met Ser Asn Leu Ala Ser Gly Val Pro Asp Arg Phe Ser
465                 470                 475                 480

Gly Ser Gly Ser Gly Thr Ala Phe Thr Leu Lys Ile Ser Arg Val Glu
            485                 490                 495

Ala Glu Asp Val Gly Val Tyr Tyr Cys Met Gln His Ile Glu Tyr Pro
        500                 505                 510

Phe Thr Phe Gly Gln Gly Thr Lys Leu Glu Ile Lys
        515                 520

<210> SEQ ID NO 33
<211> LENGTH: 1572
<212> TYPE: DNA
<213> ORGANISM: Mus musculus

<400> SEQUENCE: 33

| | | | | | |
|---|---|---|---|---|---|
| atggaatggc | ctttgatctt | tctcttcctc | ctgtcaggaa | ctgcaggtgt | ccactcccag | 60 |
| gttcagctgc | agcagtctgg | acctgagctg | gtgaagcctg | gggcctcagt | gaagatttcc | 120 |
| tgcaaggctt | ctggctatgc | attcactaac | tcctggatga | actgggtgaa | gcagaggcct | 180 |
| ggaaagggtc | ttgagtggat | tggacggatt | tatcctggag | atggagaaac | tatctacaat | 240 |
| gggaaattca | gggtcaaggc | cacactgact | gcagacaaat | cctccagcac | agcctacatg | 300 |
| gatatcagca | gcctgacatc | tgaggactct | gcggtctact | tctgtgcaag | aggctatgat | 360 |
| gattactcgt | ttgcttactg | gggccaaggg | actctggtca | ctgtctctgc | aggtggtggt | 420 |
| ggttcgggtg | gtggtggttc | gggtggtggc | ggatcggata | ttgtgatgac | tcaggctgca | 480 |
| ccctctatac | ctgtcactcc | tggagagtca | gtatccatct | cctgtaggtc | tagtaagagt | 540 |
| ctcctgcata | gtaatggcaa | cacttacttg | tattggttcc | tgcagaggcc | aggccagtct | 600 |
| cctcaactcc | tgatatatcg | gatgtccaac | cttgcctcag | gagtcccaga | taggttcagt | 660 |
| ggcagtgggt | caggaactgc | tttcacactg | agaatcagta | gagtggaggc | tgaggatgtg | 720 |
| ggtgtttatt | actgtatgca | acatatagaa | tatccttttac | gttcggatc | ggggaccaag | 780 |
| ctggaaataa | aaggaggtgg | tggatcgggt | ggtggtggtt | cgggaggcgg | tggatcgcag | 840 |
| gttcagctgc | agcagtctgg | acctgagctg | gtgaagcctg | gggcctcagt | gaagatttcc | 900 |
| tgcaaggctt | ctggctatgc | attcactaac | tcctggatga | actgggtgaa | gcagaggcct | 960 |
| ggaaagggtc | ttgagtggat | tggacggatt | tatcctggag | atggagaaac | tatctacaat | 1020 |
| gggaaattca | gggtcaaggc | cacactgact | gcagacaaat | cctccagcac | agcctacatg | 1080 |
| gatatcagca | gcctgacatc | tgaggactct | gcggtctact | tctgtgcaag | aggctatgat | 1140 |
| gattactcgt | ttgcttactg | gggccaaggg | actctggtca | ctgtctctgc | aggtggtggt | 1200 |
| ggttcgggtg | gtggtggttc | gggtggtggc | ggatcggata | ttgtgatgac | tcaggctgca | 1260 |
| ccctctatac | ctgtcactcc | tggagagtca | gtatccatct | cctgtaggtc | tagtaagagt | 1320 |
| ctcctgcata | gtaatggcaa | cacttacttg | tattggttcc | tgcagaggcc | aggccagtct | 1380 |
| cctcaactcc | tgatatatcg | gatgtccaac | cttgcctcag | gagtcccaga | taggttcagt | 1440 |
| ggcagtgggt | caggaactgc | tttcacactg | agaatcagta | gagtggaggc | tgaggatgtg | 1500 |
| ggtgtttatt | actgtatgca | acatatagaa | tatccttttac | gttcggatc | ggggaccaag | 1560 |
| ctggaaataa | aa | | | | | 1572 |

<210> SEQ ID NO 34
<211> LENGTH: 35
<212> TYPE: DNA
<213> ORGANISM: Artificial
<220> FEATURE:
<223> OTHER INFORMATION: an artificially synthesized primer sequence

```
<400> SEQUENCE: 34
cctgaattcc accatgcgat ggagctggat ctttc                                35

<210> SEQ ID NO 35
<211> LENGTH: 48
<212> TYPE: DNA
<213> ORGANISM: Artificial
<220> FEATURE:
<223> OTHER INFORMATION: an artificially synthesized primer sequence

<400> SEQUENCE: 35
accgccagag ccacctccgc ctgaaccgcc tccacctgag gagactgt                  48

<210> SEQ ID NO 36
<211> LENGTH: 57
<212> TYPE: DNA
<213> ORGANISM: Artificial
<220> FEATURE:
<223> OTHER INFORMATION: an artificially synthesized primer sequence

<400> SEQUENCE: 36
ttcaggcgga ggtggctctg gcggtggcgg aagccaaatt gttctcaccc agtcgcc       57

<210> SEQ ID NO 37
<211> LENGTH: 63
<212> TYPE: DNA
<213> ORGANISM: Artificial
<220> FEATURE:
<223> OTHER INFORMATION: an artificially synthesized primer sequence

<400> SEQUENCE: 37
accggatccg ccgccaccac tgccaccacc tcctttatc tccaactttg tccccgagcc     60
gaa                                                                   63

<210> SEQ ID NO 38
<211> LENGTH: 50
<212> TYPE: DNA
<213> ORGANISM: Artificial
<220> FEATURE:
<223> OTHER INFORMATION: an artificially synthesized primer sequence

<400> SEQUENCE: 38
ggcggatccg gtggcggtgg ctcacaggtc cagttgcagc agtctggacc               50

<210> SEQ ID NO 39
<211> LENGTH: 68
<212> TYPE: DNA
<213> ORGANISM: Artificial
<220> FEATURE:
<223> OTHER INFORMATION: an artificially synthesized primer sequence

<400> SEQUENCE: 39
attgcggccg cttatcactt atcgtcgtca tccttgtagt cttttatctc caactttgtc    60
cccgagcc                                                              68

<210> SEQ ID NO 40
<211> LENGTH: 1572
<212> TYPE: DNA
<213> ORGANISM: Mus musculus
<220> FEATURE:
<221> NAME/KEY: CDS
<222> LOCATION: (14)..(1561)

<400> SEQUENCE: 40
```

```
cctgaattcc acc atg cga tgg agc tgg atc ttt ctc ttc ctc ctg tca          49
           Met Arg Trp Ser Trp Ile Phe Leu Phe Leu Leu Ser
            1               5                  10 ata act gca ggt gtc cat tgc cag gtc cag ttg cag cag tct gga cct         97
Ile Thr Ala Gly Val His Cys Gln Val Gln Leu Gln Gln Ser Gly Pro
        15              20                  25 gag ctg gtg aag cct ggg gct tca gtg aag atg tct tgt aag gct tct        145
Glu Leu Val Lys Pro Gly Ala Ser Val Lys Met Ser Cys Lys Ala Ser
 30              35                  40 ggc tac acc ttc aca gac tac ttt ata cac tgg gtg aaa cag agg cct        193
Gly Tyr Thr Phe Thr Asp Tyr Phe Ile His Trp Val Lys Gln Arg Pro
 45              50                  55                  60 gga cag gga ctt gaa tgg att gga tgg att ttt cct gga gat gat act        241
Gly Gln Gly Leu Glu Trp Ile Gly Trp Ile Phe Pro Gly Asp Asp Thr
                 65                  70                  75 act gat tac aat gag aag ttc agg ggc aag acc aca ctg act gca gac        289
Thr Asp Tyr Asn Glu Lys Phe Arg Gly Lys Thr Thr Leu Thr Ala Asp
             80                  85                  90 aaa tcc tcc agc aca gcc tac att ttg ctc agc agc ctg acc tct gag        337
Lys Ser Ser Ser Thr Ala Tyr Ile Leu Leu Ser Ser Leu Thr Ser Glu
         95                 100                 105 gac tct gcg atg tat ttc tgt gta agg agt gac gac ttt gac tac tgg        385
Asp Ser Ala Met Tyr Phe Cys Val Arg Ser Asp Asp Phe Asp Tyr Trp
     110                 115                 120 ggc cag ggc acc act ctc aca gtc tcc tca ggt gga ggc ggt tca ggc        433
Gly Gln Gly Thr Thr Leu Thr Val Ser Ser Gly Gly Gly Gly Ser Gly
125                 130                 135                 140 gga ggt ggc tct ggc ggt ggc gga agc caa att gtt ctc acc cag tcg        481
Gly Gly Gly Ser Gly Gly Gly Gly Ser Gln Ile Val Leu Thr Gln Ser
                 145                 150                 155 cca gca atc atg tct gca tct cca ggg gag aag gtc acc ata acc tgc        529
Pro Ala Ile Met Ser Ala Ser Pro Gly Glu Lys Val Thr Ile Thr Cys
             160                 165                 170 agt gcc agc tca agt gta agt tac atg cac tgg ttc cag cag aag cca        577
Ser Ala Ser Ser Val Ser Tyr Met His Trp Phe Gln Gln Lys Pro
         175                 180                 185 ggc act ttt ccc aaa ctc tgg att tat agc aca tcc aac ctg gct tct        625
Gly Thr Phe Pro Lys Leu Trp Ile Tyr Ser Thr Ser Asn Leu Ala Ser
     190                 195                 200 gga gtc cct act cgc ttc agt ggc agt gga tct ggg acc tct tac tct        673
Gly Val Pro Thr Arg Phe Ser Gly Ser Gly Ser Gly Thr Ser Tyr Ser
205                 210                 215                 220 ctc aca atc agc cga atg gag gct gaa gat gct gcc act tat tac tgc        721
Leu Thr Ile Ser Arg Met Glu Ala Glu Asp Ala Ala Thr Tyr Tyr Cys
                 225                 230                 235 cag caa agg acg agt tat cca ccc acg ttc ggc tcg ggg aca aag ttg        769
Gln Gln Arg Thr Ser Tyr Pro Pro Thr Phe Gly Ser Gly Thr Lys Leu
             240                 245                 250 gag ata aaa gga ggt ggt ggc agt ggc ggc ggc gga tcc ggt ggc ggt        817
Glu Ile Lys Gly Gly Gly Gly Ser Gly Gly Gly Gly Ser Gly Gly Gly
         255                 260                 265 ggc tca cag gtc cag ttg cag cag tct gga cct gag ctg gtg aag cct        865
Gly Ser Gln Val Gln Leu Gln Gln Ser Gly Pro Glu Leu Val Lys Pro
270                 275                 280 ggg gct tca gtg aag atg tct tgt aag gct tct ggc tac acc ttc aca        913
Gly Ala Ser Val Lys Met Ser Cys Lys Ala Ser Gly Tyr Thr Phe Thr
                 290                 295                 300 gac tac ttt ata cac tgg gtg aaa cag agg cct gga cag gga ctt gaa        961
Asp Tyr Phe Ile His Trp Val Lys Gln Arg Pro Gly Gln Gly Leu Glu
             305                 310                 315
```

```
tgg att gga tgg att ttt cct gga gat gat act act gat tac aat gag    1009
Trp Ile Gly Trp Ile Phe Pro Gly Asp Asp Thr Thr Asp Tyr Asn Glu
            320                 325                 330 aag ttc agg ggc aag acc aca ctg act gca gac aaa tcc tcc agc aca    1057
Lys Phe Arg Gly Lys Thr Thr Leu Thr Ala Asp Lys Ser Ser Ser Thr
            335                 340                 345 gcc tac att ttg ctc agc agc ctg acc tct gag gac tct gcg atg tat    1105
Ala Tyr Ile Leu Leu Ser Ser Leu Thr Ser Glu Asp Ser Ala Met Tyr
350                 355                 360 ttc tgt gta agg agt gac gac ttt gac tac tgg ggc cag ggc acc act    1153
Phe Cys Val Arg Ser Asp Asp Phe Asp Tyr Trp Gly Gln Gly Thr Thr
365                 370                 375                 380 ctc aca gtc tcc tca ggt gga ggc ggt tca ggc gga ggt ggc tct ggc    1201
Leu Thr Val Ser Ser Gly Gly Gly Gly Ser Gly Gly Gly Gly Ser Gly
            385                 390                 395 ggt ggc gga agc caa att gtt ctc acc cag tcg cca gca atc atg tct    1249
Gly Gly Gly Ser Gln Ile Val Leu Thr Gln Ser Pro Ala Ile Met Ser
            400                 405                 410 gca tct cca ggg gag aag gtc acc ata acc tgc agt gcc agc tca agt    1297
Ala Ser Pro Gly Glu Lys Val Thr Ile Thr Cys Ser Ala Ser Ser Ser
            415                 420                 425 gta agt tac atg cac tgg ttc cag cag aag cca ggc act ttt ccc aaa    1345
Val Ser Tyr Met His Trp Phe Gln Gln Lys Pro Gly Thr Phe Pro Lys
            430                 435                 440 ctc tgg att tat agc aca tcc aac ctg gct tct gga gtc cct act cgc    1393
Leu Trp Ile Tyr Ser Thr Ser Asn Leu Ala Ser Gly Val Pro Thr Arg
445                 450                 455                 460 ttc agt ggc agt gga tct ggg acc tct tac tct ctc aca atc agc cga    1441
Phe Ser Gly Ser Gly Ser Gly Thr Ser Tyr Ser Leu Thr Ile Ser Arg
            465                 470                 475 atg gag gct gaa gat gct gcc act tat tac tgc cag caa agg acg agt    1489
Met Glu Ala Glu Asp Ala Ala Thr Tyr Tyr Cys Gln Gln Arg Thr Ser
            480                 485                 490 tat cca ccc acg ttc ggc tcg ggg aca aag ttg gag ata aaa gac tac    1537
Tyr Pro Pro Thr Phe Gly Ser Gly Thr Lys Leu Glu Ile Lys Asp Tyr
            495                 500                 505 aag gat gac gac gat aag tga taa gcggccgcaa t                       1572
Lys Asp Asp Asp Asp Lys
    510

<210> SEQ ID NO 41
<211> LENGTH: 4
<212> TYPE: PRT
<213> ORGANISM: Artificial
<220> FEATURE:
<223> OTHER INFORMATION: An artificially synthesized peptide sequence

<400> SEQUENCE: 41

Gly Gly Gly Ser
1

<210> SEQ ID NO 42
<211> LENGTH: 4
<212> TYPE: PRT
<213> ORGANISM: Artificial
<220> FEATURE:
<223> OTHER INFORMATION: An artificially synthesized peptide sequence

<400> SEQUENCE: 42

Ser Gly Gly Gly
1
```

```
<210> SEQ ID NO 43
<211> LENGTH: 5
<212> TYPE: PRT
<213> ORGANISM: Artificial
<220> FEATURE:
<223> OTHER INFORMATION: An artificially synthesized peptide sequence

<400> SEQUENCE: 43

Gly Gly Gly Gly Ser
1               5

<210> SEQ ID NO 44
<211> LENGTH: 5
<212> TYPE: PRT
<213> ORGANISM: Artificial
<220> FEATURE:
<223> OTHER INFORMATION: An artificially synthesized peptide sequence

<400> SEQUENCE: 44

Ser Gly Gly Gly Gly
1               5

<210> SEQ ID NO 45
<211> LENGTH: 6
<212> TYPE: PRT
<213> ORGANISM: Artificial
<220> FEATURE:
<223> OTHER INFORMATION: An artificially synthesized peptide sequence

<400> SEQUENCE: 45

Gly Gly Gly Gly Gly Ser
1               5

<210> SEQ ID NO 46
<211> LENGTH: 6
<212> TYPE: PRT
<213> ORGANISM: Artificial
<220> FEATURE:
<223> OTHER INFORMATION: An artificially synthesized peptide sequence

<400> SEQUENCE: 46

Ser Gly Gly Gly Gly Gly
1               5

<210> SEQ ID NO 47
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 47

Gly Gly Gly Gly Gly Gly Ser
1               5

<210> SEQ ID NO 48
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 48

Ser Gly Gly Gly Gly Gly Gly
1               5
```

<210> SEQ ID NO 49
<211> LENGTH: 118
<212> TYPE: PRT
<213> ORGANISM: Artificial
<220> FEATURE:
<223> OTHER INFORMATION: An artificially synthesized sequence

<400> SEQUENCE: 49

```
Glu Val Gln Leu Val Gln Ser Gly Ala Glu Val Gln Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Glu Gly Leu Glu Trp Met
        35                  40                  45

Gly Tyr Ile Asn Pro Ser Ser Gly Tyr Thr Lys Tyr Asn Arg Lys Phe
    50                  55                  60

Arg Asp Arg Val Thr Ile Thr Ala Asp Lys Ser Ser Thr Ser Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Gln Gly Tyr Tyr Leu Asp Tyr Trp Gly Glu Gly Thr
            100                 105                 110

Thr Val Thr Val Ser Ser
        115
```

<210> SEQ ID NO 50
<211> LENGTH: 119
<212> TYPE: PRT
<213> ORGANISM: Artificial
<220> FEATURE:
<223> OTHER INFORMATION: An artificially synthesized sequence

<400> SEQUENCE: 50

```
Glu Val Gln Leu Val Gln Ser Gly Ala Gln Val Lys Lys Pro Gly Ala
1               5                   10                  15

Ser Val Lys Val Ser Cys Lys Ala Ser Gly Tyr Thr Phe Ser Asp Asn
            20                  25                  30

Asn Met Asp Trp Val Arg Gln Ala Pro Gly Lys Gly Leu Glu Trp Met
        35                  40                  45

Gly Asp Ile Asn Thr Lys Ser Gly Gly Ser Ile Tyr Asn Gln Lys Phe
    50                  55                  60

Lys Gly Arg Val Ile Met Thr Ile Asp Lys Ser Thr Gly Thr Ala Tyr
65                  70                  75                  80

Met Glu Leu Arg Ser Leu Arg Ser Asp Asp Thr Ala Ile Tyr Tyr Cys
                85                  90                  95

Ala Arg Arg Arg Ser Tyr Gly Tyr Tyr Phe Asp Tyr Trp Gly Arg Gly
            100                 105                 110

Thr Leu Val Thr Val Ser Ser
        115
```

<210> SEQ ID NO 51
<211> LENGTH: 106
<212> TYPE: PRT
<213> ORGANISM: Artificial
<220> FEATURE:
<223> OTHER INFORMATION: An artificially synthesized sequence

<400> SEQUENCE: 51

```
Asp Ile Val Met Thr Gln Ser Pro Ser Ser Leu Ser Ala Ser Val Gly
1               5                   10                  15
```

```
Asp Arg Val Thr Ile Thr Cys Lys Ala Ser Gln Asn Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Ala Ser Gly Val Pro Ser Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Leu Ala Thr Tyr Tyr Cys Gln Gln Tyr Ser Asn Tyr Ile Thr
                85                  90                  95

Phe Gly Gln Gly Thr Lys Val Glu Ile Lys
            100                 105

<210> SEQ ID NO 52
<211> LENGTH: 15
<212> TYPE: PRT
<213> ORGANISM: Artificial
<220> FEATURE:
<223> OTHER INFORMATION: An artificially synthesized peptide sequence

<400> SEQUENCE: 52

Gly Gly Gly Gly Ser Gly Gly Gly Gly Ser Gly Gly Gly Gly Ser
1               5                   10                  15
```

STABILIZER FOR PROTEIN PREPARATION COMPRISING MEGLUMINE AND USE THEREOF

CROSS-REFERENCE TO RELATED APPLICATIONS

This application is the National Stage of International Application No. PCT/JP2006/311625, filed on Jun. 9, 2006, which claims the benefit of Japanese Patent Application Serial No. 2005-170794, filed on Jun. 10, 2005. The contents of all of the foregoing applications are hereby incorporated by reference in their entireties.

TECHNICAL FIELD

The present invention relates to agents for stabilizing proteins, which comprise meglumine, an amino sugar, and uses thereof. More specifically, the present invention relates to agents for stabilizing antibody molecules, which comprise meglumine, and methods for stabilizing antibody molecules, which comprise the step of adding meglumine. The present invention also relates to pharmaceutical compositions comprising antibody molecules stabilized by meglumine and methods for producing the pharmaceutical compositions.

BACKGROUND ART

Preparations that enable stable preservation of proteins used as pharmaceuticals are required for the formulation of biopharmaceuticals (Non-Patent Document 1).

Generally, there are two known pathways of protein degradation: the degradation pathway involving physical association of protein molecules, such as formation of soluble multimers or precipitate/insoluble material (Non-Patent Document 2) and the degradation pathway involving chemical modification, such as hydrolysis, deamidation, and methionine oxidation (Non-Patent Document 3). When proteins are developed as pharmaceuticals, decrease in biological activities during storage of proteins in the preparations to be provided should be prevented by suppressing insofar as possible both deterioration pathways. Methods for suppressing the degradation pathways as much as possible include optimization of pH of the solution, and optimization of types and concentrations of buffer, salt, and stabilizer.

Antibodies that can be used as pharmaceuticals include whole antibodies, antibody fragments, minibodies, and modified antibodies (fusion proteins between antibodies and other proteins, and antibody conjugates). In general, IgG antibody preparations are required to contain very high concentrations of IgG. Such preparations are known to be extremely difficult to prepare (Non-Patent Document 5). In addition to pH optimization and optimization of buffer type, various attempts have been made to stabilize antibodies. For example, stabilized high-concentration antibody preparations comprising acidic ingredients have been disclosed in WO 02/096457 (Patent Document 1). In these preparations, $MgCl_2$ or $CaCl_2$ are used as additives for antibody stabilization. Meanwhile, it is known that minibodies and the like have a high tendency to aggregate and have very low stability (Non-Patent Documents 8 and 9). scFv monomers are also known to aggregate very easily, and form dimers at high concentrations (Non-Patent Document 10). Thus, in the development of pharmaceuticals that are solution preparations of such antibodies, a very important objective is to stabilize antibody molecules in the solutions (specifically to suppress their aggregation).

In general, freeze-dried proteins are more stable than proteins in solutions (the aggregation is suppressed). Thus, the antibody preparations described above may be formulated as freeze-dried preparations, if it is difficult to formulate the preparations as solutions (Non-Patent Documents 11, 12, and 13). Sucrose has been reported to be an effective excipient when IgG antibodies are freeze-dried (Non-Patent Document 14).

Meglumine has been used as an X-ray contrast medium (meglumine amidotrizoate), an MRI contrast medium (meglumine gadopentetate), or such. However, there is no report on the protein-stabilizing effect of meglumine.

[Non-Patent Document 1] Nat. Rev. Drug Discov. 2005, 4(4), 298-306
[Non-Patent Document 2] Int. J. Pharm. 2005, 289, 1-30
[Non-Patent Document 3] Int. J. Pharm. 1999, 185, 129-188
[Non-Patent Document 4] J. Pharm. Sci. 2004, 93(6), 1390-1402
[Non-Patent Document 5] Pharmaceutical Research 1994, 11(5), 624-632
[Non-Patent Document 6] Clin. Chem. Lab. Med. 2000, 38(8):759-764
[Non-Patent Document 7] Journal of Immunological Methods, 111 (1988), 17-23
[Non-Patent Document 8] FEBS Letters Volume 360, Issue 3, 1995, 247-250
[Non-Patent Document 9] FEBS Letters, 1995, 441, 458-462
[Non-Patent Document 10] J. Mol. Biol. 2002, 320, 107-127
[Non-Patent Document 11] Pharm Biotechnol, 2002, 13, 109-33
[Non-Patent Document 12] Int. J. Pharm. 2000, 203(1-2), 1-60
[Non-Patent Document 13] Pharm. Res. 1997, 14(8), 969-75
[Non-Patent Document 14] J. Pharm. Sci. 2001, 90(3), 310-21
[Patent Document 1] WO 02/096457

DISCLOSURE OF THE INVENTION

Problems to be Solved by the Invention

The present invention was achieved under such circumstances. An objective of the present invention is to provide methods for stabilizing proteins, which comprise the step of adding meglumine, an amino sugar, to proteins.

More specifically, the objective is to provide methods for stabilizing antibody molecules or suppressing aggregation of antibody molecules, which comprise the step of adding meglumine to antibody molecules. Another objective of the present invention is to provide meglumine-containing agents for stabilizing antibody molecules or suppressing aggregation of antibody molecules. Still another objective is to provide pharmaceutical compositions comprising antibody molecules stabilized by meglumine, methods for producing the pharmaceutical compositions, and kits comprising the pharmaceutical compositions.

Means for Solving the Problems

To achieve the above-described objectives, the present inventors tested the antibody-stabilizing effect of meglumine, an amino sugar.

First, the inventors tested the aggregation-suppressing effect of meglumine using hVB22B sc(Fv)2, which is an sc(Fv)2. The result demonstrated that the addition of meglumine considerably increased the residual monomer ratio, and thus, the aggregation of hVB22B could be significantly suppressed. This study revealed that the addition of meglumine significantly improved stability of minibodies that have a low stability. In addition, this study demonstrated for the first time that meglumine is useful as a protein stabilizer.

Next, the present inventors assessed the stabilizing effect of meglumine on other sc(Fv)2 molecules and whole antibodies. The result showed that the addition of meglumine had the effect of generally suppressing the aggregation of antibody molecules, such as whole IgG antibodies, in addition to sc(Fv)2.

The present invention also revealed that, as compared to sucrose, meglumine has a stronger effect in suppressing the formation of aggregates in solution and freeze-dried preparations, and against stress imposed during the freeze-drying process. The present invention also demonstrated that meglumine produced a strong stabilizing effect even when the antibody concentration was as very high as 100 mg/ml in preparations, regardless of being in a solution or freeze-dried state. The present invention also discovered that the addition of meglumine suppressed aggregation of antibody molecules during long-term storage at low temperatures or room temperatures.

Specifically, by the present invention the present inventors discovered for the first time that meglumine is useful as a stabilizer for antibody molecules, and thus completed the present invention.

More specifically, the present invention provides the following [1] to [21]:

[1] An agent for long-term stabilization of a protein, which comprises meglumine;
[2] An agent for suppressing protein aggregation, which comprises meglumine;
[3] The agent of [1] or [2], wherein the protein is an antibody molecule;
[4] The agent of [3], wherein the antibody molecule is a whole antibody, antibody fragment, minibody, modified antibody, or antibody-like molecule;
[5] The agent of any one of [1] to [4], whose dosage form is a freeze-dried preparation;
[6] The agent of any one of [1] to [5], wherein the meglumine is a salt or a derivative thereof;
[7] A method for long-term stabilization of a protein, which comprises the step of adding meglumine to the protein;
[8] A method for suppressing protein aggregation, which comprises the step of adding meglumine to the protein;
[9] The method of [7] or [8], wherein the protein is stabilized for a long period or protein aggregation is suppressed under long-term storage conditions at a low temperature;
[10] The method of [7] or [8], wherein the protein is stabilized for a long period or protein aggregation is suppressed under long-term storage conditions at room temperature;
[11] The method of any one of [7] to [10], wherein the protein is an antibody molecule;
[12] The method of [11], wherein the antibody molecule is a whole antibody, antibody fragment, minibody, modified antibody, or antibody-like molecule;
[13] The method of any one of [7] to [12], which comprises the step of freeze-drying the protein after the step of adding meglumine;
[14] The method of any one of [7] to [13], wherein the meglumine is a salt, or a derivative thereof;
[15] A pharmaceutical composition comprising meglumine;
[16] The pharmaceutical composition of [15], whose dosage form is a freeze-dried preparation;
[17] The pharmaceutical composition of [15] or [16], wherein the meglumine is a salt, or a derivative thereof;
[18] A method for producing a pharmaceutical composition comprising an antibody molecule, which comprises the step of adding meglumine to an antibody-containing composition;
[19] A method for producing a pharmaceutical composition comprising an antibody molecule, which comprises the steps of:
(1) adding meglumine to an antibody-containing composition; and
(2) freeze-drying the mixture of (1);
[20] The method for producing a pharmaceutical composition of [18] or [19], wherein the antibody molecule is a whole antibody, antibody fragment, minibody, modified antibody, or antibody-like molecule; and
[21] The method of any one of [18] to [20], wherein the meglumine is a salt, or a derivative thereof.

BRIEF DESCRIPTION OF THE DRAWINGS

FIG. 2 is a diagram showing the stabilizing effect of meglumine on sc(Fv)2 molecules and a whole antibody. The numerals in this diagram represent the aggregate content(%) under the solution acceleration conditions.

FIG. 3 is a diagram showing the stabilizing effect of meglumine in the formulation of IgG into solution preparations or freeze-dried preparations.

BEST MODE FOR CARRYING OUT THE INVENTION

Figure 1:
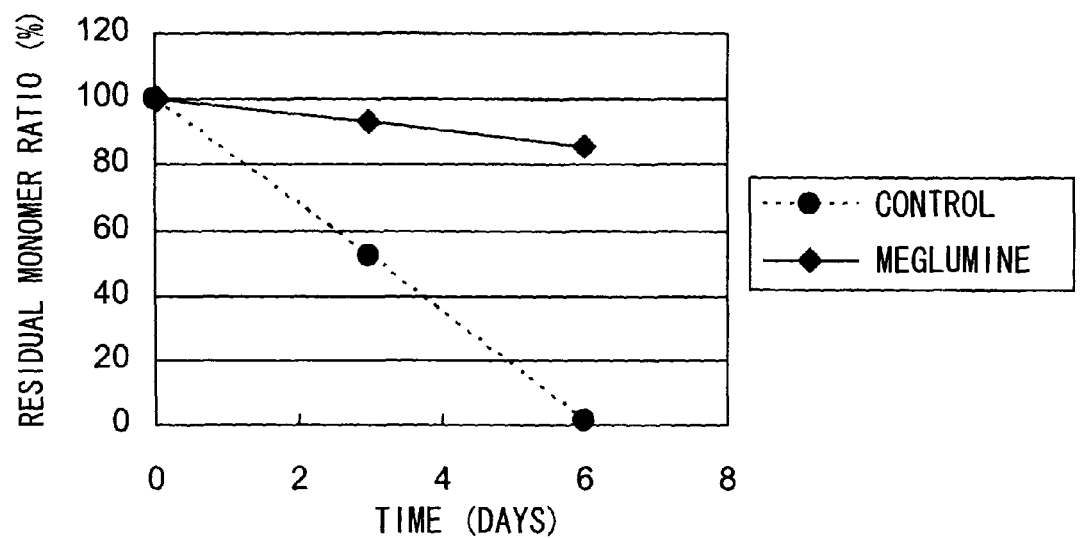
FIG. 1 is a graph showing the hVB22B-stabilizing effect of meglumine.

The present inventors investigated agents for stabilizing sc(Fv)2 and discovered the novel stabilizer meglumine, which is an amino sugar. The inventors also found that meglumine stabilized not only sc(Fv)2s, which are minibodies, but also whole antibodies. The inventors also discovered that meglumine had a superior effect of stabilizing proteins such as antibody molecules and peptides, as compared to sugars such as sucrose, and amino sugars that were generally used as stabilizers for protein pharmaceuticals. The present invention was achieved based on the findings described above.

The present invention relates to methods for stabilizing proteins, which comprise the step of adding meglumine to proteins. The stabilization according to the present invention may be long-term stabilization. Herein, "long-term stabilization" is defined as follows. When the preparation is a minibody solution, long-term stabilization means that the aggregate content is 35% or less after two weeks of storage at 55° C.; alternatively, it is 10% or less, preferably 7% or less, after two weeks of storage at 40° C.; alternatively, it is 1% or less after two months of storage at 25° C.; alternatively, it is 2% or less, preferably 1% or less, after six months of storage at −20° C. When the preparation is a solution of any antibody other than a minibody, or a general protein solution, long-term stabilization means that the aggregate content is 20% or less, preferably 10% or less, after three weeks of storage at 60° C.; alternatively, it is 2% or less, preferably 1% or less, after six months of storage at −20° C. Alternatively, when the preparation is a freeze-dried preparation of any antibody, including IgGs and minibodies, or a general freeze-dried protein preparation, long-term stabilization means that the aggregate content is 5% or less, preferably 1% or less, and more preferably 0.5% or less, after one month of storage at 40° C.

Herein, "meglumine" (also known as N-methylglucamine) refers to the compound represented by the formula 1-Deoxy-1-methylamino-D-glucitol, and compounds represented by the following formula.

[Compound 1]

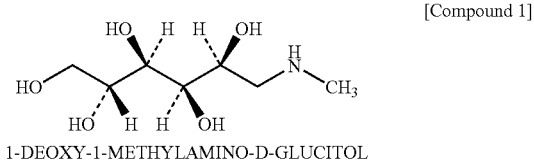

1-DEOXY-1-METHYLAMINO-D-GLUCITOL

Herein, "meglumine" includes derivatives and salts of meglumine. The derivatives and salts of meglumine include, but are not limited to, meglumine amidotrizoate, meglumine sodium amidotrizoate, meglumine cadopentetate, meglumine gadoterate, meglumine iotalamate, meglumine iotroxate, meglumine gadobenate, meglumine iodoxamate, meglumine flunixin, and gastrografin (meglumine sulfate). Products resulting from chemical modification of hydroxyl group, amino group, or others of the above-listed meglumines are also included in the meglumine of the present invention.

Target pharmaceutical compositions (proteins) to be stabilized according to the present invention may be proteins, including peptides, or other biopolymers, synthetic polymers, low molecular weight compounds, derivatives thereof, or complexes comprising a combination thereof. A preferred example of the present invention is antibodies.

Target antibodies to be stabilized according to the present invention may be known antibodies, and may be any of whole antibodies, antibody fragments, modified antibodies, and minibodies.

Known whole antibodies include IgGs (IgG1s, IgG2s, IgG3s, and IgG4s), IgDs, IgEs, IgMs, IgYs, and such. The type of antibody is not particularly limited. Whole antibodies also include bispecific IgG antibodies (J Immunol Methods. 2001 Feb. 1; 248(1-2):7-15).

Antibodies prepared by methods known to those skilled in the art using novel antigens can also be targeted. Specifically, for example, novel antibodies can be prepared by the procedure described below.

Immunization is carried out by conventional immunization methods using a novel antigen protein or a fragment thereof as a sensitizing antigen. The prepared immune cells are fused with known parent cells by conventional cell fusion methods. The fused cells are screened for monoclonal antibody-producing cells (hybridomas) by conventional screening methods. Antigens can be prepared by known methods, for example, methods using baculovirus (WO 98/46777). Hybridomas can be prepared, for example, according to the method of Milstein et al. (Kohler. G. and Milstein, C., Methods Enzymol. (1981) 73: 3-46). When the antigen has low immunogenicity, immunization can be performed using the antigen bound to immunogenic macromolecules, such as albumin. Then, cDNAs encoding the variable regions (V regions) of the antibodies are synthesized from the mRNAs of hybridomas using a reverse transcriptase. The resulting cDNAs may be sequenced by known methods.

Antibodies that recognize a novel antigen are not particularly limited, as long as they bind to the novel antigen, and mouse antibodies, rat antibodies, rabbit antibodies, sheep antibodies, human antibodies, and others can be appropriately used. Furthermore, to reduce heterologous antigenicity against humans, artificially modified recombinant antibodies, for example, chimeric antibodies and humanized antibodies, can be used. Such modified antibodies can be produced by known methods. A chimeric antibody comprises heavy chain and light chain variable regions of an antibody from a non-human mammal such as a mouse, and heavy chain and light chain constant regions of a human antibody. Such an antibody can be obtained by ligating a DNA encoding a variable region of a mouse antibody to a DNA encoding a constant region of a human antibody, inserting the resulting construct into an expression vector, and introducing the vector into a host for production of the antibody.

A humanized antibody, which is also called a reshaped human antibody, is obtained by transferring a complementarity determining region (CDR) of an antibody of a nonhuman mammal such as a mouse, to the CDR of a human antibody. Conventional genetic recombination techniques for the preparation of such antibodies are known. Specifically, a DNA sequence designed to ligate a CDR of a mouse antibody with the framework regions (FRs) of a human antibody is synthesized by PCR, using several oligonucleotides constructed to comprise overlapping portions at their ends. A humanized antibody can be obtained by ligating the obtained DNA to a DNA that encodes a human antibody constant region, inserting the resulting construct into an expression vector, and introducing the vector into a host to produce the antibody (see European Patent Application No. EP 239,400, and International Patent Application No. WO 96/02576). Human antibody FRs ligated via the CDR of which the CDR forms a favorable antigen-binding site are selected. As necessary, amino acids in the framework region of an antibody variable region may be substituted such that the CDR of a reshaped human antibody forms an appropriate antigen-binding site (Sato, K. et al., Cancer Res. (1993) 53, 851-856).

Methods for obtaining human antibodies are also known. For example, desired human antibodies with antigen-binding activity can be obtained by sensitizing human lymphocytes with desired antigens or cells expressing desired antigens in vitro and fusing the sensitized lymphocytes with human myeloma cells such as U266 (see Japanese Patent Application Kokoku Publication No. (JP-B) H1-59878 (examined, approved Japanese patent application published for opposition)). Alternatively, the desired human antibodies can be obtained by using desired antigens to immunize transgenic animals comprising the entire repertoire of human antibody genes (see International Patent Application WO 93/12227, WO 92/03918, WO 94/02602, WO 94/25585, WO 96/34096, and WO 96/33735). Furthermore, techniques to obtain human antibodies by panning with a human antibody library are known. For example, the variable regions of human antibodies are expressed as single chain antibodies (scFvs) on the surface of phages, using a phage display method, and the phages that bind to the antigen can be selected. By analyzing the genes of selected phages, the DNA sequences encoding the variable regions of human antibodies that bind to the antigen can be determined. If the DNA sequences of scFvs that bind to the antigen are identified, appropriate expression vectors comprising these sequences can be constructed to obtain human antibodies. Such methods are already well known (see WO 92/01047, WO 92/20791, WO 93/06213, WO 93/11236, WO 93/19172, WO 95/01438, and WO 95/15388).

Target antibodies to be stabilized according to the present invention include antibody fragments and minibodies. The antibodies may be known antibodies or newly prepared antibodies. The antibody fragments and minibodies include antibody fragments which lack a portion of a whole antibody (for example, whole IgG). The antibody fragments and minibodies are not particularly limited, as long as they have the ability to bind to an antigen. Specifically, the antibody fragments include, for example, Fab, Fab', F(ab')2, Fv, scFv (single chain Fv) (Huston, J. S. et al., Proc. Natl. Acad. Sci. U.S.A. (1988) 85, 5879-5883, Plickthun "The Pharmacology of Monoclonal Antibodies" Vol. 113, Resenburg and Moore eds., Springer Verlag, New York, pp. 269-315, (1994)), VHH (camelid VH, J. Biotechnol. 2001 June; 74(4):277-302.), and sc(Fv)2. Preferred antibody fragments are sc(Fv)2. Such an antibody fragment can be prepared by treating an antibody with an enzyme (for example, papain or pepsin) or by inserting a gene construct encoding the antibody fragment into an expression vector and expressing it in appropriate host cells (see for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; Bird, R. E. and Walker, B. W., Trends Biotechnol. (1991) 9, 132-137).

Preferred minibodies of the present invention are antibodies that comprise two or more antibody VHs and two or more antibody VLs, in which each of the variable regions are directly linked, or indirectly linked together via linkers or such. The linkages may be covalent or non-covalent bonds, or comprise both covalent and non-covalent bonds. More preferred minibodies are antibodies comprising two or more VH-VL pairs formed via non-covalent bonding between VH and VL. The distance between two VH-VL pairs in a minibody is preferably less than that in the whole antibody.

In the present invention, minibodies include scFvs, diabodies, and sc(Fv)2s. scFvs are fragments in which two variable regions are linked together via a linker or such.

Diabodies are dimers obtained by linking two units of scFvs or such (hereinafter, referred to as a fragment constituting a diabody), and typically comprise two VLs and two VHs. The linkages between fragments constituting a diabody may be non-covalent or covalent bonds, and are preferably non-covalent bonds.

Fragments constituting diabodies include fragments consisting of VL and VH linked together, fragments consisting of VL and VL linked together, fragments consisting of VH and VH linked together, and the like. Fragments consisting of VH and VL linked together are preferred. There is no limitation on the linker for linking two variable regions in a fragment constituting a diabody; however, it is preferable to use a linker short enough to prevent formation of a non-covalent bond between variable regions in the same fragment. Those skilled in the art can appropriately determine the length of such linkers; however, their length is typically 2 to 14 amino acids, preferably 3 to 9 amino acids, and more preferably 4 to 6 amino acids. In these cases, the linker between the VL and VH encoded by the same fragment is short, and thus, no non-covalent bonds are formed between VL and VH on the same chain. Thus, a single chain V region fragment is not formed, and dimers are formed with other fragments via non-covalent bonds. Furthermore, based on the same principle for producing diabodies, a multimerized antibody such as a trimer or tetramer can be prepared by linking three or more fragments constituting a diabody.

sc(Fv)2s are antibodies that are single-chain polypeptides obtained by linking two heavy chain variable regions ([VH]) and two light chain variable regions ([VL]) via linkers or such (Hudson et al., J. Immunol. Methods (1999) 231:177-189). The two VHs and VLs may also be derived from different monoclonal antibodies. sc(Fv)2s include, for example, bispecific sc(Fv)2s that recognize two types of antigens or two types of epitopes, as disclosed in Journal of Immunology, 1994, 152, 5368-5374. sc(Fv)2s can be prepared, for example, by linking two single chain Fvs (scFvs) together via a linker or such (Huston, J. S. et al., Proc. Natl. Acad. Sci. U.S.A. (1988) 85, 5879-5883, Plickthun "The Pharmacology of Monoclonal Antibodies" Vol. 113, Resenburg and Moore eds., Springer Verlag, New York, pp. 269-315, (1994)). Such linkers may be arbitrary peptide linkers that can be introduced by genetic engineering, or synthetic linker compounds, for example, the linkers disclosed in Protein Engineering, 9(3), 299-305, 1996. However, peptide linkers are preferred in the present invention. The length of the peptide linkers is not particularly limited and can be appropriately selected by those skilled in the art, depending on the purpose, and is typically 1 to 100 amino acids, preferably 5 to 30 amino acids, and more preferably 12 to 18 amino acids (for example, 15 amino acids).

The order of the two sets of VH and the two sets of VL to be linked is not particularly limited and may be any order, including for example, the following arrangements.

[VH] linker [VL] linker [VH] linker [VL]
[VL] linker [VH] linker [VH] linker [VL]
[VH] linker [VL] linker [VL] linker [VH]
[VH] linker [VH] linker [VL] linker [VL]
[VL] linker [VL] linker [VH] linker [VH]
[VL] linker [VH] linker [VL] linker [VH]

In the context of the present invention, a preferred sc(Fv)2 arrangement is [VH] linker [VL] linker [VH] linker [VL].

The amino acid sequence of the heavy chain variable region or the light chain variable region may contain substitutions, deletions, additions, and/or insertions. Furthermore, it may also lack portions of heavy chain variable region and/or light chain variable region, or other polypeptides may be added, as long as the binding complex of heavy chain variable regions and light chain variable regions retains its antigen binding activity. Additionally, the variable region may be chimerized or humanized.

In the present invention, the linkers to be used for linking the variable regions of an antibody comprise arbitrary peptide linkers that can be introduced by genetic engineering, synthetic linker compounds, for example, those disclosed in Protein Engineering, 9(3), 299-305, 1996.

In the present invention, preferred linkers are peptide linkers. The length of the polypeptide linkers is not particularly limited and can be suitably selected according to the purpose by those skilled in the art. Normally, the length is 1-100 amino acids, preferably 13-50 amino acids, more preferably 5-30 amino acids, and even more preferably 12-18 amino acids (for example, 15 amino acids).

For example, amino acid sequences for such peptide linkers include:

Ser

Gly • Ser

Gly • Gly • Ser

Ser • Gly • Gly

Gly • Gly • Gly • Ser (SEQ ID NO: 41)

Ser • Gly • Gly • Gly (SEQ ID NO: 42)

Gly • Gly • Gly • Gly • Ser (SEQ ID NO: 43)

Ser • Gly • Gly • Gly • Gly (SEQ ID NO: 44)

Gly • Gly • Gly • Gly • Gly • Ser (SEQ ID NO: 45)

Ser • Gly • Gly • Gly • Gly • Gly (SEQ ID NO: 46)

Gly • Gly • Gly • Gly • Gly • Gly • Ser (SEQ ID NO: 47)

Ser • Gly • Gly • Gly • Gly • Gly • Gly (SEQ ID NO: 48)

(Gly • Gly • Gly • Gly • Ser (SEQ ID NO: 43))n (Ser • Gly • Gly • Gly • Gly (SEQ ID NO: 44))n

[where n is an integer of 1 or larger]

Synthetic linkers (chemical crosslinking agents) include crosslinking agents routinely used to crosslink peptides, for example, N-hydroxy succinimide (NHS), disuccinimidyl suberate (DSS), bis(succinimidyl) suberate (BS3), dithiobis (succinimidyl propionate) (DSP), dithiobis(succinimidyl propionate) (DTSSP), ethylene glycol bis(succinimidyl succinate) (EGS), ethylene glycol bis(sulfosuccinimidyl succinate) (sulfo-EGS), disuccininidyl tartrate (DST), disulfosuccinimidyl tartrate (sulfo-DST), bis[2-(succinimidoxycarbonyloxy)ethyl]sulfone (BSOCOES), and bis[2-(succinimidoxycarbonyloxy)ethyl]sulfone (sulfo-BSOCOES). These crosslinking agents are commercially available.

In general, three linkers are required to link four antibody variable regions together. The linkers to be used may all be the same or different.

sc(Fv)2s can be prepared by methods known to those skilled in the art. For example, sc(Fv)2s can be prepared by introducing into a host cell a vector comprising DNA encoding sc(Fv)2 as an insert, expressing sc(Fv)2, and collecting the expression products.

The vectors are not particularly limited, and any vector can be used so long as it can stably carry the insert DNA. For example, when Escherichia coli (E. coli) is used as the host, various commercially available vectors may be used; however, preferred cloning vectors are pBluescript vector (Stratagene). When using vectors for the purpose of producing an sc(Fv)2 of the present invention, expression vectors are particularly useful. The expression vectors are not particularly limited so long as the vectors express sc(Fv)2 in vitro, in E. coli, in culture cells, or in a body of an organism. For example, pBEST vector (Promega) is preferred for in vitro expression; pET vector (Invitrogen), for E. coli; pME18S-FL3 vector (GenBank Accession No. AB009864), for culture cells; and pME18S vector (Mol Cell Biol. 8:466-472 (1988)), for organisms. DNAs of the present invention can be inserted into the vectors by conventional methods, for example, by ligation using restriction sites (Current protocols in Molecular Biology, eds. Ausubel et al. (1987) Publish. John Wiley & Sons, Section 11.4-11.11).

The host cells described above are not particularly limited, and depending on the purpose, various host cells can be used. Cells for expressing sc(Fv)2 include, for example, bacterial cells (for example, Streptococcus, Staphylococcus, E. coli, Streptomyces, and Bacillus subtilis); fungal cells (for example, yeast and Aspergillus); insect cells (for example, Drosophila S2 and Spodoptera SF9); animal cells (for example, CHO, COS, HeLa, C127, 3T3, BHK, HEK293, and Bowes melanoma cell); and plant cells. The vectors can be introduced into host cells by known methods, for example, calcium-phosphate precipitation method, electroporation (Current protocols in Molecular Biology, eds. Ausubel et al. (1987) Publish. John Wiley & Sons, Section 9.1-9.9), lipofectamine method (GIBCO-BRL), and microinjection method.

When an sc(Fv)2 of the present invention is secreted into culture media, the sc(Fv)2 can be collected by collecting the culture media. Alternatively, when the sc(Fv)2 is produced within cells, the cells are first lysed and then the sc(Fv)2 compositions are collected.

Methods for preparing polypeptides functionally equivalent to a certain polypeptide are well known to those skilled in the art, and include methods of introducing mutations into polypeptides. For example, those skilled in the art can prepare an antibody functionally equivalent to the antibodies of the present invention by introducing appropriate mutations into the antibody using site-directed mutagenesis (Hashimoto-Gotoh, T. et al. Gene 152, 271-275, (1995); Zoller, M J, and Smith, M. Methods Enzymol. 100, 468-500, (1983); Kramer, W. et al., Nucleic Acids Res. 12, 9441-9456, (1984); Kramer, W. and Fritz H J, Methods Enzymol. 154, 350-367, (1987); Kunkel, T A, Proc. Natl. Acad. Sci. USA. 82, 488-492, (1985); Kunkel, Methods Enzymol. 85, 2763-2766, (1988)), or such. Amino acid mutations may occur naturally. Thus, the present invention also comprises antibodies functionally equivalent to the antibodies of the present invention and comprising the amino acid sequences of these antibodies, in which one or more amino acids is mutated.

In such mutants, the number of amino acids that may be mutated is not particularly restricted and is generally within 30 amino acids, preferably within 15 amino acids, and more preferably within 5 amino acids (for example, within three amino acids). Preferably, amino acids residues are mutated into amino acids that conserve the characteristics of the amino acid side chain. Examples of amino acid side chain properties are: hydrophobic amino acids (A, I, L, M, F, P, W, Y, and V), hydrophilic amino acids (R, D, N, C, E, Q, G, H, K, S, and T), amino acids comprising the following side chains: aliphatic side chains (G; A, V, L, I, and P); hydroxyl-containing side chains (S, T, and Y); sulfur-containing side chains (C and M); carboxylic acid- and amide-containing side chains (D, N, E, and Q); basic side chains (R, K, and H); aromatic ring-containing side chains (H, F, Y, and W) (amino acids are represented by one-letter codes in parentheses). A polypeptide comprising a modified amino acid sequence, in which one or more amino acid residues is deleted, added, and/or replaced with other amino acids, is known to retain its original biological activity (Mark, D. F. et al., Proc. Natl. Acad. Sci. USA 81, 5662-5666 (1984); Zoller, M. J. & Smith, M. Nucleic Acids Research 10, 6487-6500 (1982); Wang, A. et al., Science 224, 1431-1433; Dalbadie-McFarland, G. et al., Proc. Natl. Acad. Sci. USA 79, 6409-6413 (1982)). Amino acid sequences of antibody constant regions and the like are known to those skilled in the art.

The antibodies to be used in the present invention may be modified antibodies. Modified antibodies may be conjugated antibodies obtained by linking with various molecules, such as polyethylene glycol (PEG), radioactive substances, and toxins.

Furthermore, the modified antibodies include not only conjugated antibodies but also fusion proteins between an antibody molecule, antibody molecule fragment, or antibody-like molecule, and other proteins or peptides. Such fusion proteins include, but are not particularly limited to, fusion proteins between TNFα and Fc (Int J Clin Pract. 2005 January; 59(1): 114-8) and fusion proteins between IL-2 and scFv (J Immunol Methods. 2004 December; 295(1-2):49-56).

Furthermore, antibodies used in the present invention may also be antibody-like molecules. Antibody-like molecules include affibodies (Proc Natl Acad Sci USA. 2003 Mar. 18; 100(6):3191-6) and ankyrins (Nat Biotechnol. 2004 May; 22(5):575-82), but are not particularly limited thereto.

The antibodies described above can be produced by methods known to those skilled in the art. Specifically, DNA of an antibody of interest is inserted into an expression vector so that the DNA is expressed under the regulation of an expression regulatory region, for example, an enhancer and a promoter. Then, host cells are transformed with the expression vector to express the antibody. Hosts and expression vectors can be used in appropriate combination.

Vectors include, for example, M13 vectors, pUC vectors, pBR322, pBluescript, and pCR-Script. In addition to the above vectors, for example, pGEM-T, pDIRECT, and pT7 can also be used for the subcloning and excision of cDNAs.

In particular, expression vectors are useful when using vectors for producing antibodies. When an expression vector is expressed, for example, in *E. coli*, it should have the above characteristics in order to be amplified in *E. coli*. Additionally, when *E. coli*, such as JM109, DH5α, HB101, or XL1-Blue are used as the host cell, the vector preferably has a promoter, for example, lacZ promoter (Ward et al. (1989) Nature 341:544-546; (1992) FASEB J. 6:2422-2427), araB promoter (Better et al. (1988) Science 240:1041-1043), or T7 promoter, that allows efficient expression of the desired gene in *E. coli*. Other examples of the vectors include pGEX-5X-1 (Pharmacia), "QIAexpress system" (QIAGEN), pEGFP, and pET (where BL21, a strain expressing T7 RNA polymerase, is preferably used as the host).

Furthermore, the vectors may comprise a signal sequence for polypeptide secretion. When producing polypeptides into the periplasm of *E. coli*, the pelB signal sequence (Lei, S. P. et al. J. Bacteriol. 169:4379 (1987)) may be used as a signal sequence for polypeptide secretion. For example, calcium chloride methods or electroporation methods may be used to introduce the vector into a host cell.

In addition to *E. coli*, expression vectors derived from mammals (e.g., pCDNA3 (Invitrogen), pEGF-BOS (Nucleic Acids Res. (1990) 18(17):5322), pEF, pCDM8), insect cells (e.g., "Bac-to-BAC baculovirus expression system" (GIBCO-BRL), pBacPAK8), plants (e.g., pMH1, pMH2), animal viruses (e.g., pHSV, pMV, pAdexLcw), retroviruses (e.g., pZIPneo), yeasts (e.g., "*Pichia* Expression Kit" (Invitrogen), pNV11, SP-Q01), and *Bacillus subtilis* (e.g., pPL608, pKTH50) may also be used as a vector for producing polypeptides of the present invention.

In order to express proteins in animal cells such as CHO, COS, and NIH3T3 cells, the vector preferably has a promoter necessary for expression in such cells, for example, an SV40 promoter (Mulligan et al. (1979) Nature 277:108), MMLV-LTR promoter, EF1α promoter (Mizushima et al. (1990) Nucleic Acids Res. 18:5322), CMV promoter, etc.). It is even more preferable that the vector also carries a marker gene for selecting transformants (for example, a drug-resistance gene selected by a drug such as neomycin and G418. Examples of vectors with such characteristics include pMAM, pDR2, pBK-RSV, PBK-CMV, pOPRSV, and pOP13, and such.

In addition, to stably express a gene and amplify the gene copy number in cells, CHO cells that are defective in the nucleic acid synthesis pathway are introduced with a vector containing a DHFR gene (for example, pCHOI) to compensate for the defect, and the copy number is amplified using methotrexate (MTX). Alternatively, a COS cell, which carries an SV40 T antigen-expressing gene on its chromosome, can be transformed with a vector containing the SV40 replication origin (for example, pcD) for transient gene expression. The replication origin may be derived from polyoma virus, adenovirus, bovine papilloma virus (BPV), and such. Furthermore, to increase the gene copy number in host cells, the expression vector may contain, as a selection marker, aminoglycoside transferase (APH) gene, thymidine kinase (TK) gene, *E. coli* xanthine guanine phosphoribosyl transferase (Ecogpt) gene, dihydrofolate reductase (dhfr) gene, and such.

Herein, "adding" meglumine to proteins also means mixing meglumine with proteins. Herein, "mixing" meglumine with proteins may mean dissolving proteins in a meglumine-containing solution.

Herein, "stabilizing" means maintaining proteins in the natural state or preserving their activity.

Furthermore, when protein activity is enhanced upon addition of a stabilizer comprising meglumine of the present invention as compared to the natural state or a control or when the degree of activity reduction due to aggregation during storage is decreased, the protein can also be assumed to be stabilized. Specifically, whether the activity of a protein, for example, an antibody molecule, is enhanced can be tested by assaying the activity of interest under the same conditions. Target antibody molecules to be stabilized include newly synthesized antibodies and antibodies isolated from organisms.

The activity of the present invention may be any activity, such as binding activity, neutralizing activity, cytotoxic activity, agonistic activity, antagonistic activity, and enzymatic activity. The activity is not particularly limited; however, the activity is preferably an activity that quantitatively and/or qualitatively alters or influences living bodies, tissues, cells, proteins, DNAs, RNAs, and such. Agonistic activities are especially preferred.

"Agonistic activity" refers to an activity that induces a change in some physiological activity by transducing a signal into cells and such, due to the binding of an antibody to an antigen such as a receptor. Physiological activities include, but are not limited to, for example, proliferation activity, survival activity, differentiation activity, transcriptional activity, membrane transportation activity, binding activity, proteolytic activity, phosphorylation/dephosphorylation activity, oxidation/reduction activity, transfer activity, nucleolytic activity, dehydration activity, cell death-inducing activity, and apoptosis-inducing activity.

The antigens of the present invention are not particularly limited, and any antigen may be used. Examples of antigens include, receptors, tumor antigens, MHC antigens, and differentiation antigens. Examples of receptors include receptors belonging to receptor families such as the hematopoietic growth factor receptor family, the cytokine receptor family, the tyrosine kinase receptor family, the serine/threonine kinase receptor family, the TNF receptor family, the G protein-coupled receptor family, the GPI-anchored receptor family, the tyrosine phosphatase receptor family, the adhesion factor family, and the hormone receptor family. There are many documents that describe receptors belonging to these receptor families, and their characteristics, which include for example, Cooke B A, King R J B, van der Molen H J Eds. New Comprehensive Biochemistry Vol. 1813 "Hormones and their Actions Part II" pp. 1-46 (1988) Elsevier Science Publishers BV, New York, USA; Patthy L. (1990) Cell, 61: 13-14; Ullrich A. et al. (1990) Cell, 61: 203-212; Massagul J. (1992) Cell, 69: 1067-1070; Miyajima A. et al. (1992) Annu. Rev. Immunol., 10: 295-331; Taga T. and Kishimoto T. (1992) FASEB J., 7: 3387-3396; Fantl W I. et al. (1993) Annu. Rev. Biochem., 62: 453-481; Smith C A., et al. (1994) Cell, 76: 959-962; Flower D R. (1999) Biochim. Biophys. Acta, 1422: 207-234; SAIBO KOGAKU (Cell Technology) Supplementary vol. Handbook series "Handbook for Adhesion factors" M. Miyasaka Ed. (1994) Shujunnsha, Tokyo, Japan, and so on.

Specific receptors belonging to the receptor families listed above include: human or mouse erythropoietin (EPO) receptor, human or mouse granulocyte-colony stimulating factor (G-CSF) receptor, human or mouse thrombopoietin (TPO) receptor, human or mouse insulin receptor, human or mouse Flt-3 ligand receptor, human or mouse platelet-derived growth factor (PDGF) receptor, human or mouse interferon (IFN)-$\alpha$ and -$\beta$ receptor, human or mouse leptin receptor, human or mouse growth hormone (GH) receptor, human or mouse interleukin (IL)-10 receptor, human or mouse insulin-like growth factor (IGF)-I receptor, human or mouse leukemia inhibitory factor (LIF) receptor, and human or mouse ciliary neurotrophic factor (CNTF) receptor (hEPOR: Simon, S. et al. (1990) Blood 76, 31-35; mEPOR: D'Andrea, A D. et al. (1989) Cell 57, 277-285; hG-CSFR: Fukunaga, R. et al. (1990) Proc. Natl. Acad. Sci. USA. 87, 8702-8706; mG-CSFR: Fukunaga, R. et al. (1990) Cell 61, 341-350; hTPOR: Vigon, I. et al. (1992) 89, 5640-5644; mTPOR: Skoda, R C. et al. (1993) 12, 2645-2653; hInsR: Ullrich, A. et al. (1985) Nature 313, 756-761; hFlt-3: Small, D. et al. (1994) Proc. Natl. Acad. Sci. USA. 91, 459-463; hPDGFR: Gronwald, R G K. et al. (1988) Proc. Natl. Acad. Sci. USA. 85, 3435-3439; hIFN $\alpha/\beta$ R: Uze, G et al. (1990) Cell 60, 225-234, and Novick, D. et al. (1994) Cell 77, 391-400).

Tumor antigens, which are also called tumor-specific antigens, are expressed along with malignant transformation of cells. Furthermore, abnormal sugar chains displayed on cellular surface or protein molecules upon canceration of cells also serve as tumor antigens, and are called tumor-associated carbohydrate antigens in particular. Tumor antigens include, for example, CA19-9, CA15-3, sialyl SSEA-1 (SLX) and the like.

MHC antigens are broadly grouped under MHC class I and II antigens. MHC class I antigens include HLA-A, -B, -C, -E, -F, -G, and -H, while MHC class II antigens include HLA-DR, -DQ, and -DP.

Differentiation antigens include CD1, CD2, CD3, CD4, CD5, CD6, CD7, CD8, CD10, CD11a, CD11b, CD11c, CD13, CD14, CD15s, CD16, CD18, CD19, CD20, CD21, CD23, CD25, CD28, CD29, CD30, CD32, CD33, CD34, CD35, CD38, CD40, CD41a, CD41b, CD42a, CD42b, CD43, CD44, CD45, CD45RO, CD48, CD49a, CD49b, CD49c, CD49d, CD49e, CD49f, CD51, CD54, CD55, CD56, CD57, CD58, CD61, CD62E, CD62L, CD62P, CD64, CD69, CD71, CD73, CD95, CD102, CD106, CD122, CD126, CDw130 and such.

There is no limitation as to the type of detection indicators to be used for determining the change in activity, as long as the indicator can monitor quantitative and/or qualitative changes. For example, it is possible to use cell-free assay indicators, cell-based assay indicators, tissue-based assay indicators, and biological indicators.

Indicators that can be used in cell-free assays include enzymatic reactions, quantitative and/or qualitative changes in proteins, DNAs, or RNAs. Such enzymatic reactions include, for example, amino acid transfers, sugar transfers, dehydrations, dehydrogenations, and substrate cleavages. Alternatively, protein phosphorylations, dephosphorylations, dimerizations, multimerizations, hydrolyses, dissociations and such; DNA or RNA amplifications, cleavages, and extensions can be used as the indicator in cell-free assays. For example, protein phosphorylations downstream of a signal transduction pathway may be used as a detection indicator.

Alterations in cell phenotype, for example, quantitative and/or qualitative alterations in products, alterations in growth activity, alterations in cell number, morphological alterations, or alterations in cellular properties, can be used as indicators in cell-based assays. The products include, for example, secretory proteins, surface antigens, intracellular proteins, and mRNAs. The morphological alterations include, for example, alterations in dendrite formation and/or dendrite number, alteration in cell flatness, alteration in cell elongation/axial ratio, alterations in cell size, alterations in intracellular structure, heterogeneity/homogeneity of cell populations, and alterations in cell density. Such morphological alterations can be observed under a microscope. Cellular properties to be used as the indicator include anchor dependency, cytokine-dependent response, hormone dependency, drug resistance, cell motility, cell migration activity, pulsatory activity, and alteration in intracellular substances. Cell motility includes cell infiltration activity and cell migration activity. Alterations in intracellular substances include, for example, alterations in enzyme activity, mRNA levels, levels of intracellular signaling molecules such as Ca2+ and cAMP, and intracellular protein levels. When a cell membrane receptor is used, alterations in the cell proliferating activity induced by receptor stimulation can be used as the indicator.

Indicators to be used in tissue-based assays include functional alterations adequate for the subject tissue. Alterations in tissue weight, alterations in the blood system (for example, alterations in blood cell counts, protein contents, or enzyme activities), alterations in electrolyte levels, and alterations in the circulating system (for example, alterations in blood pressure or heart rate) can be used as biological indicators.

The methods for measuring such detection indices are not particularly limited. For example, absorbance, luminescence, color development, fluorescence, radioactivity, fluorescence polarization, surface plasmon resonance signal, time-resolved fluorescence, mass, absorption spectrum, light scattering, and fluorescence resonance energy transfer may be used. These measurement methods are known to those skilled in the art and may be selected appropriately depending on the purpose.

For example, absorption spectra can be obtained by using a conventional photometer, plate reader, or such; luminescence can be measured with a luminometer or such; and fluorescence can be measured with a fluorometer or such. Mass can be determined with a mass spectrometer. Radioactivity can be determined with a device such as a gamma counter depending on the type of radiation. Fluorescence polarization can be measured with BEACON (TaKaRa). Surface plasmon resonance signals can be obtained with BIACORE. Time-resolved fluorescence, fluorescence resonance energy transfer, or such can be measured with ARVO or such. Furthermore, a flow cytometer can also be used for measuring. It is possible to use one of the above methods to measure two or more different types of detection indices. A greater number of detection indices may also be examined by using two or more measurement methods simultaneously and/or consecutively. For example, fluorescence and fluorescence resonance energy transfer can be measured at the same time with a fluorometer.

In the present invention, agonistic activities can be assayed by methods known to those skilled in the art. For example, agonistic activities can be determined by methods using cell growth as an indicator, as described in the Examples. More specifically, an antibody whose agonistic activity is to be determined is added to cells which proliferate in an agonist-dependent manner, followed by incubation of the cells. Then, a reagent such as WST-8 which shows a coloring reaction at specific wavelengths depending on the viable cell count, is added to the culture and the absorbance is measured. Subsequently, the agonistic activity can be determined using the obtained absorbance as an indicator.

Cells that proliferate in an agonist-dependent manner can also be prepared by methods known to those skilled in the art. For example, when the antigen is a receptor capable of transducing cell growth signals, cells expressing the receptor may be used. Alternatively, when the antigen is a receptor that cannot transduce signals, a chimeric receptor consisting of the intracellular domain of a receptor that transduces cell growth signals and the extracellular domain of a receptor that does not transduce cell growth signals can be prepared for cellular expression. Receptors that transduce cell growth signals include, for example, G-CSF receptors, mpl, neu, GM-CSF receptors, EPO receptors, c-kit, and FLT-3. Cells that can be used to express a receptor include, for example, BaF3, NFS60, FDCP-1, FDCP-2, CTLL-2, DA-1, and KT-3.

Herein, "stabilizing" proteins means suppressing the increase of protein aggregate amount during storage by suppressing protein aggregation, and/or suppressing the increase in the amount of insoluble aggregates (precipitates) formed during storage, and/or maintaining protein function. Preferably, "stabilizing" proteins means suppressing the increase of the amount of protein aggregates formed during storage.

The present invention relates to methods for suppressing protein aggregation, which comprise the step of adding meglumine, an amino sugar, to proteins. More specifically, the present invention relates to methods for suppressing aggregation of antibody molecules, which comprise the step of adding meglumine to antibody molecules.

Herein, aggregation refers to formation of multimers consisting of two or more antibody molecules via reversible or irreversible aggregation of proteins (antibody molecules). Whether the aggregation is suppressed can be tested by measuring the content of antibody molecule aggregates by methods known to those skilled in the art, for example, sedimentation equilibrium method (ultracentrifugation method), osmometry, light scattering method, low-angle laser light scattering method, small angle X-ray scattering method, small-angle neutron scattering method, and gel filtration. When the content of antibody aggregates during storage is reduced upon addition of meglumine, the aggregation can be interpreted to be suppressed.

Methods for determining the content of antibody aggregates include methods using size exclusion chromatography (SEC) described in the Examples, but are not limited thereto.

Herein, "stabilizing antibody molecules" include stabilizing antibody molecules in antibody solution preparations, freeze-dried antibody preparations, and spray-dried preparations, regardless of antibody concentration and condition, and also include stabilizing antibody molecules that are stored for a long term at a low temperature or room temperature. Herein, low-temperature storage includes, for example, storage at −80° C. to 10° C. Thus, cryopreservation is also included in the storage means. Preferred low temperatures include, for example, −20° C. and 5° C., but are not limited thereto. Herein, room temperature storage includes, for example, storage at 15° C. to 30° C. Preferred room temperatures include, for example, 25° C., but are not limited thereto.

Solution preparations can be formulated by methods known to those skilled in the art. For example, the membrane concentration method using a TFF membrane is routinely used, as described in a Non-Patent Document (J. Pharm. Sc, 2004, 93(6), 1390-1402).

Freeze-drying can be carried out by methods known to those skilled in the art (Pharm. Biotechnol, 2002, 13, 109-33; Int. J. Pharm. 2000, 203(1-2), 1-60; Pharm. Res. 1997, 14(8), 969-75). For example, adequate amounts of solutions are aliquoted into vessels such as vials for freeze-drying. The vessels are placed in a freezing chamber or freeze drying chamber, or immersed in a refrigerant, such as acetone/dry ice or liquid nitrogen, to achieve freeze-drying.

Furthermore, spray-dried preparations can be formulated by methods known to those skilled in the art (J. Pharm. Sci. 1998 November; 87(11):1406-11).

Formulation of solution preparations and freeze drying can also be achieved using the methods described in the Examples; however, formulation and freeze drying methods are not limited thereto.

The present invention relates to agents for stabilizing proteins and agents for suppressing protein aggregation, which comprise meglumine, an amino sugar. More specifically, the present invention relates to agents for stabilizing antibody molecules and agents for suppressing aggregation of antibody molecules, which comprise meglumine.

The present invention also relates to agents for stabilizing antibody molecules and agents for stabilizing antibody molecules in freeze-dried antibody preparations, which comprise meglumine.

The agents of the present invention may comprise pharmaceutically acceptable carries, such as preservatives and stabilizers. "Pharmaceutically acceptable carriers" means pharmaceutically acceptable materials that can be administered in combination with the above-described agents, and which themselves may or may not have the above-described protein-stabilizing action. Alternatively, the carriers may be materials without a stabilization effect or materials that produce a synergistic or additive stabilization effect when used in combination with meglumine.

Such pharmaceutically acceptable materials include, for example, sterile water, physiological saline, stabilizers, excipients, buffers, preservatives, detergents, chelating agents (EDTA and such), and binders.

In the present invention, detergents include nonionic detergents, typical examples of which being sorbitan fatty acid esters such as sorbitanmonocaprylate, sorbitan monolaurate, and sorbitan monopalmitate; glycerin fatty acid esters such as glycerin monocaprylate, glycerin monomyristate and glycerin monostearate; polyglycerin fatty acid esters such as decaglyceryl monostearate, decaglyceryl distearate, and decaglyceryl monolinoleate; polyoxyethylene sorbitan fatty acid esters such as polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, and polyoxyethylene sorbitan tristearate; polyoxyethylene sorbit fatty acid esters such as polyoxyethylene sorbit tetrastearate and polyoxyethylene sorbit tetraoleate; polyoxyethylene glycerin fatty acid esters such as polyoxyethylene glyceryl monostearate; polyethylene glycol fatty acid esters such as polyethylene glycol distearate; polyoxyethylene alkyl ethers such as polyoxyethylene lauryl ether; polyoxyethylene polyoxypropylene alkyl ethers such as polyoxyethylene polyoxypropylene glycol, polyoxyethylene polyoxypropylene propyl ether, and polyoxyethylene polyoxypropylene cetyl ether; polyoxyethylene alkyl phenyl ethers such as polyoxyethylene nonylphenyl ether; polyoxyethylene hardened castor oils such as polyoxyethylene castor oil and polyoxyethylene hardened castor oil (polyoxyethylene hydrogenated castor oil); polyoxyethylene beeswax derivatives such as polyoxyethylene sorbit beeswax; polyoxyethylene lanolin derivatives such as polyoxyethylene lanolin; and polyoxyethylene fatty acid amides such as polyoxyethylene stearic acid amide and such, with an HLB of 6 to 18.

Detergents also include anionic detergents, and typical examples of such include alkylsulfates having an alkyl group with 10 to 18 carbon atoms, such as sodium cetylsulfate, sodium laurylsulfate, and sodium oleylsulfate; polyoxyethylene alkyl ether sulfates in which the alkyl group has 10 to 18 carbon atoms and the average molar number of added ethylene oxide is 2 to 4, such as sodium polyoxyethylene lauryl sulfate; alkyl sulfosuccinate ester salts having an alkyl group with 8 to 18 carbon atoms, such as sodium lauryl sulfosuccinate ester; natural detergents, for example, lecithin, glycerophospholipids; sphingo-phospholipids such as sphingomyelin; and sucrose fatty acid esters in which the fatty acids have 12 to 18 carbon atoms.

One type, or a combination of two or more types of the detergents described above can be added to the preparations of the present invention. Detergents that are preferably used in the preparations of the present invention include polyoxyethylene sorbitan fatty acid esters, such as polysorbates 20, 40, 60, and 80. Polysorbates 20 and 80 are particularly preferred. Polyoxyethylene polyoxypropylene glycols, represented by poloxamer (Pluronic F-68™ and such), are also preferred.

The amount of detergent added varies depending on the type of detergent used. When polysorbate 20 or polysorbate 80 is used, the amount is in general 0.001 to 100 mg/ml, preferably 0.003 to 50 mg/ml, and more preferably 0.005 to 2 mg/ml.

In the present invention, buffers include phosphate, citrate buffer, acetic acid, malic acid, tartaric acid, succinic acid, lactic acid, potassium phosphate, gluconic acid, caprylic acid, deoxycholic acid, salicylic acid, triethanolamine, fumaric acid, and other organic acids; and carbonic acid buffer, Tris buffer, histidine buffer, and imidazole buffer.

Solution preparations may be prepared by dissolving the agents in aqueous buffers known in the field of liquid preparations. The buffer concentration is in general 1 to 500 mM, preferably 5 to 100 mM, and more preferably 10 to 20 mM.

The agents of the present invention may also comprise other low molecular weight polypeptides; proteins such as serum albumin, gelatin, and immunoglobulin; amino acids; sugars and carbohydrates such as polysaccharides and monosaccharides; sugar alcohols and such.

Herein, amino acids include basic amino acids, for example, arginine, lysine, histidine, and ornithine, and inorganic salts of these amino acids (preferably in the form of hydrochlorides, and phosphates, namely phosphate amino acids). When free amino acids are used, the pH is adjusted to a preferred value by adding appropriate physiologically acceptable buffering substances, for example, inorganic acids, in particular hydrochloric acid, phosphoric acid, sulfuric acid, acetic acid, and formic acid, and salts thereof. In this case, the use of phosphate is particularly beneficial because it gives especially stable freeze-dried products. Phosphate is particularly advantageous when preparations do not substantially contain organic acids, such as malic acid, tartaric acid, citric acid, succinic acid, and fumaric acid, or do not contain corresponding anions (malate ion, tartrate ion, citrate ion, succinate ion, fumarate ion, and such). Preferred amino acids are arginine, lysine, histidine, and ornithine. Furthermore, acidic amino acids, for example, glutamic acid and aspartic acid, and salts thereof (preferably sodium salts); neutral amino acids, for example, isoleucine, leucine, glycine, serine, threonine, valine, methionine, cysteine, and alanine; and aromatic amino acids, for example, phenylalanine, tyrosine, tryptophan, and its derivative, N-acetyl tryptophan may also be used.

Herein, sugars and carbohydrates such as polysaccharides and monosaccharides include, for example, dextran, glucose, fructose, lactose, xylose, mannose, maltose, sucrose, trehalose, and raffinose.

Herein, sugar alcohols include, for example, mannitol, sorbitol, and inositol.

When the agents of the present invention are prepared as aqueous solutions for injection, the agents may be mixed with, for example, physiological saline, and/or isotonic solution containing glucose or other auxiliary agents (such as D-sorbitol, D-mannose, D-mannitol, and sodium chloride). The aqueous solutions may be used in combination with appropriate solubilizing agents such as alcohols (ethanol and such), polyalcohols (propylene glycol, PEG, and such), or non-ionic detergents (polysorbate 80 and HCO-50).

The agents may further comprise, if required, diluents, solubilizers, pH adjusters, soothing agents, sulfur-containing reducing agents, antioxidants, and such.

Herein, sulfur-containing reducing agents include, for example, compounds comprising sulfhydryl groups, such as N-acetylcysteine, N-acetylhomocysteine, thioctic acid, thiodiglycol, thioethanolamine, thioglycerol, thiosorbitol, thioglycolic acid and salts thereof, sodium thiosulfate, glutathione, and thioalkanoic acids having 1 to 7 carbon atoms.

Moreover, the antioxidants in the present invention include, for example, erythorbic acid, dibutylhydroxy toluene, butylhydroxy anisole, α-tocopherol, tocopherol acetate, L-ascorbic acid and salts thereof, L-ascorbic acid palmitate, L-ascorbic acid stearate, sodium hydrogen sulfite, sodium sulfite, triamyl gallate, propyl gallate, and chelating agents such as disodium ethylenediamine tetraacetic acid (EDTA), sodium pyrophosphate, and sodium metaphosphate.

If required, the agents may be encapsulated in microcapsules (microcapsules of hydroxymethylcellulose, gelatin, poly[methylmethacrylic acid] or such) or prepared as colloidal drug delivery systems (liposome, albumin microspheres, microemulsion, nano-particles, nano-capsules, and such) (see "Remington's Pharmaceutical Science 16th edition", Oslo Ed., 1980, and the like). Furthermore, methods for making agents into sustained-release agents are also known, and are applicable to the present invention (Langer et al., J. Biomed. Mater. Res. 1981, 15: 167-277; Langer, Chem. Tech. 1982, 12: 98-105; U.S. Pat. No. 3,773,919); European Patent Application No. (EP) 58, 481; Sidman et al., Biopolymers 1983, 22: 547-556; and EP 133,988).

The present invention relates to pharmaceutical compositions comprising antibody molecules stabilized by meglumine, an amino sugar. The present invention also relates to pharmaceutical compositions comprising antibody molecules in which their aggregation is suppressed by meglumine, an amino sugar. The present invention also relates to kits comprising the pharmaceutical compositions and pharmaceutically acceptable carriers.

The pharmaceutical compositions and kits of the present invention may comprise pharmaceutically acceptable materials, in addition to the stabilized antibody molecules described above. Such pharmaceutically acceptable materials include the materials described above.

The formula (dosage form) of the pharmaceutical compositions of the present invention includes injections, freeze-dried preparations, solutions, and spray-dried preparations, but is not limited thereto.

In general, the preparations of the present invention can be provided in containers with a fixed volume, such as closed sterile plastic or glass vials, ampules, and injectors, or large volume containers, such as bottles. Prefilled syringes are preferred for the convenience of use.

Administration to patients may be an oral or parenteral administration, and is preferably a parenteral administration, such as an injection. Administration by injection includes, for example, intravenous injection, intramuscular injection, intraperitoneal injection, and subcutaneous injection, for systemic or local administration. The administration methods can be suitably selected according to the patient's age and symptoms. The single-administration dose of a protein, peptide, or antibody can be selected, for example, from the range of 0.0001 mg to 1000 mg/kg body weight. Alternatively, the dose can be selected, for example, from the range of 0.001 to 100,000 mg/patient. However, the dose and administration method of the present invention are not limited to those described above. The dose of a low molecular weight compound as an active ingredient is in the range of 0.1 to 2000 mg/adult/day. However, the dose and administration method of the present invention are not limited to those described above.

The freeze-dried or spray-dried preparations of the present invention can be made into solution preparations prior to use. Thus, the present invention also provides kits comprising freeze-dried or spray-dried preparations of the present invention and pharmaceutically acceptable carriers. There is no limitation on the type of pharmaceutically acceptable carrier, or on whether there is a combination of carriers or not, as long as the pharmaceutically acceptable carrier(s) allows formulation of freeze-dried or spray-dried preparations into solution preparations. The aggregation of antibody molecules in solution preparations can be suppressed by using a stabilizer of the present invention as a pharmaceutically acceptable carrier, or a part of pharmaceutically acceptable carrier.

The present invention relates to methods for producing pharmaceutical compositions comprising antibody molecules, which comprise the step of adding meglumine to antibodies to stabilize the antibody molecules. The present invention also relates to methods for producing pharmaceutical compositions comprising antibody molecules, which comprise the step of adding meglumine to antibodies to suppress the aggregation of the antibody molecules. The present invention also relates to methods for producing pharmaceutical compositions comprising antibody molecules, which comprise the steps of: (1) adding meglumine to antibodies and (2) formulating the mixture of (1) into solution preparations. The present invention also relates to methods for producing pharmaceutical compositions comprising antibody molecules, which comprise the steps of: (1) adding meglumine to antibodies and (2) freeze-drying the mixture of (1).

The formulation of solution preparations and freeze drying can be carried out by the methods described above.

All prior art documents cited herein are incorporated herein by reference.

EXAMPLES

Hereinbelow, the present invention will be more specifically described with reference to the Examples, but it is not to be construed as being limited thereto.

Example 1

Evaluation of hVB22B Stabilization by Meglumine

The aggregation-suppressing effect of meglumine was tested using hVB22B sc(Fv)2 u2-wz4 (SEQ ID NO: 1; see Reference Examples described below), a highly purified sc(Fv)2. The solvent condition and hVB22B concentration used in the stabilization test are shown below.

[Stabilization Test Conditions]
Control: 20 mM sodium citrate, pH6.5
Meglumine: 20 mM sodium citrate, 10% meglumine, pH6.5
hVB22B u2-wz4: 1.0 mg/ml After three and six days of incubation at 55° C., the residual monomer ratio was determined by size exclusion chromatography (SEC) under the conditions described above (the residual monomer ratio is defined as the percentage of monomer peak area in the heat acceleration sample to that of the initial state). The conditions for SEC analysis is described below.

[Conditions for SEC Analysis]
Column: TSKgel Super2000sw (TOSOH)
Eluant: 50 mM sodium phosphate, 300 mM KCl, pH7.0
Flow rate: 0.2 ml/min
Detection wavelength: 220 nm The result of SEC analysis is shown in FIG. 1. FIG. 1 shows the change in residual monomer ratio over time, from the initial ratio to the ratio after three and six days of incubation at 55° C. under the solution conditions described above.

The result showed that the addition of meglumine considerably increased the residual monomer ratio as compared to the control, demonstrating that the aggregation of hVB22B can be markedly suppressed. This study elucidated that the addition of meglumine significantly improved the stability of minibodies, which have very low stability. In addition, this study revealed for the first time that meglumine is useful as a protein stabilizer.

Example 2

Evaluation of the Stabilizing Effect of Meglumine on Other sc(Fv)2 Molecules and Whole Antibodies The stabilization effect of meglumine on sc(Fv)2s other than hVB22B described in Example 1 was tested. The sc(Fv)2s used were: mVB22B (SEQ ID NO: 2; see Reference Examples described below), 12E10 (SEQ ID NO: 3; WO 02/33072), and 2D7 (SEQ ID NO: 4; see Reference Examples described below) listed below. The stabilization effect on a humanized anti-IL-6 receptor antibody (H chain, SEQ ID NO: 5; L chain, SEQ ID NO: 6; WO 92/19759), which is not an sc(Fv)2 but a whole antibody IgG1, was also tested. The solvent conditions and concentration of each antibody used in the stabilization test are shown below.

[Stabilization Test Conditions]
Control: 20 mM citrate buffer, pH6.5
Meglumine: 20 mM citrate buffer, 10% meglumine, pH6.5
mVB22B: 28 ug/ml; measurement was carried out after one week and two weeks of incubation at 40° C.
2D7: 59 ug/ml; measurement was carried out after one week and two weeks of incubation at 40° C.
12E10: 10 ug/ml; measurement was carried out after one week and two weeks of incubation at 55° C.
IgG: 6.84 mg/ml; measurement was carried out after one week and three weeks of incubation at 60° C.

The heat acceleration test was carried out under the condition described above.

[Conditions for SEC Analysis]
mVB22B, 2D7, and 12E10 were analyzed under the conditions described below.
Column: TSKgel Super2000SW (TOSOH)
Eluant: 50 mM sodium phosphate, 300 mM KCl, pH7.0
Flow rate: 0.2 ml/min Detection wavelength: 220 nm
 IgG was analyzed under the conditions described below.
Column: TSKgel G3000SWxl (TOSOH)
Eluant: DPBS(−)
Flow rate: 0.5 ml/min
Detection wavelength: 220 nm
 FIG. 2 shows the change in aggregate content over time under each solution acceleration condition described above. The stabilization test result showed that the addition of meglumine suppressed the formation of aggregates of not only sc(Fv)2 and IgG but also of other types of molecules. The result described above demonstrates that the addition of meglumine has the effect of suppressing aggregation of not only sc(Fv)2 but also general antibody molecules, such as whole antibody IgG. To date, there is no report describing that meglumine serves as a stabilizer for antibody molecules. This investigation revealed for the first time that meglumine is useful as a stabilizer for antibody molecules.

Example 3

Evaluation of Meglumine as a Stabilizer for IgG Solutions or as an Excipient for Freeze-Dried IgG Preparations The stabilization effect of meglumine as a stabilizer for IgG solution preparations or as an excipient for freeze-dried IgG preparations was tested. Sucrose, a popular stabilizer, was used as a control stabilizer (excipient) for IgG.
 Sucrose has been reported to be very useful in preparing freeze-dried antibody agents. Samples tested and stabilization test conditions are described below:
[Tested Samples]
Sample 1: IgG 80 mg/vial, sucrose 100 mg/vial, polysorbate 80 1 mg/vial, sodium phosphate 30 μmol/vial, pH6.0
Sample 2: IgG 80 mg/vial, sucrose 70 mg/vial, polysorbate 80 1 mg/vial, sodium phosphate 30 μmol/vial, pH6.0
Sample 3: IgG 80 mg/vial, sucrose 50 mg/vial, polysorbate 80 1 mg/vial, sodium phosphate 30 μmol/vial, pH6.0
Sample 4: IgG 80 mg/vial, meglumine 55 mg/vial, polysorbate 80 1 mg/vial, sodium phosphate 30 μmol/vial, pH6.0
Sample 5: IgG 80 mg/vial, meglumine 40 mg/vial, polysorbate 80 1 mg/vial, sodium phosphate 30 μmol/vial, pH6.0
Sample 6: IgG 80 mg/vial, meglumine 30 mg/vial, polysorbate 80 1 mg/vial, sodium phosphate 30 μmol/vial, pH6.0
 Freeze-dried preparations were prepared from the samples listed above by aliquoting solutions prior to freeze drying, in which IgG concentration was adjusted to 40 mg/ml, into vials (2 ml/vial) and freeze-drying them using a shelf-freeze dryer under the condition indicated below.

| * Freeze-drying conditions | |
|---|---|
| Name of process | Temperature |
| Prefreezing | −50° C. |
| Primary drying | −20° C. |
| Secondary drying | 25 → 30° C. |

Solution preparations were prepared from the samples listed above by adding 0.6 ml of water for injections to each vial of the freeze-dried preparations. The concentration of IgG in each vial was about 120 mg/ml.
[Stabilization Test Conditions]
Before and after freeze-drying: the solutions prior to freeze-drying and freeze-dried preparations were tested.
Freeze-dried preparation: samples after one-month storage at 40° C. were tested.
Solution preparation: samples after two-week storage at 25° C. were tested.
[SEC Analysis Conditions]
 The analysis was carried out under the conditions described below.
Column: TSKgel G30000SWxl (TOSOH)
Eluant: phosphate buffer, pH7.0 (50 mmol/l phosphate buffer (pH7.0) containing 300 mmol/l sodium chloride and 0.05% sodium azide)
Flow rate: 1 ml/min
Detection wavelength: 280 nm
 FIG. 3 shows a comparison of the effects of sucrose and meglumine on the aggregate content before and after freeze-drying (solutions prior to freeze-drying and freeze-dried preparations), comparison of the effects of sucrose and meglumine on the aggregate content in freeze-dried preparations after one month of acceleration test at 40° C., and comparison of the effects of sucrose and meglumine on the aggregate content in solution preparations after two weeks of acceleration test at 25° C.
 In each comparison, the aggregate content was lower with meglumine than with sucrose. This indicates that compared to sucrose, meglumine has a greater stabilization effect against aggregate formation. The stabilization effect was also found to depend on meglumine concentration, and the stabilization effect was stronger as meglumine concentration increased. Specifically, with regard to the stress imposed on antibodies during the drying process of the freeze-drying step, the addition of meglumine could suppress the increase of aggregates caused by freeze-drying in a meglumine concentration-dependent manner. The aggregation in freeze-dried preparations during one month of storage at 40° C. could also be suppressed in the same way. Furthermore, the aggregation in solution preparations with a concentration of about 120 mg/ml during two weeks of storage at 25° C. could also be suppressed in the same way. Thus, as compared to sucrose, meglumine was found to have a stronger stabilization effect, even for solution preparations with high concentrations, such as those above 100 mg/ml, and regardless of the status of the preparation, whether in solutions or freeze-dried preparations.

Example 4

Stabilization Effect of Meglumine on hVB22B u2-wz4 During Storage at −20° C.

hVB22B u2-wz4 was expressed by the method described in Reference Examples 1 to 3 herein, or in WO 2005/056603 or WO 2005/056604, and then the single-chain diabody-type sc(Fv)2 was purified. Formulae (F1 and F2) were prepared from the purified single-chain diabody-type sc(Fv)2 according to the following solution conditions:
F1: 10 mg/ml single-chain diabody-type sc(Fv)2
 20 mM histidine (pH6.8)+150 mM NaCl+0.5 mg/ml Polysorbate 80
F2: 10 mg/ml single-chain diabody-type sc(Fv)2+150 mM meglumine
 20 mM histidine (pH6.8)+150 mM NaCl+0.5 mg/ml Polysorbate 80
 These samples were frozen and stored at −20° C. for six months. The aggregate contents in the sample prior to storage (initial) and the samples after six months of storage at −20° C. (−20° C.-6M) were analyzed by gel filtration chromatography (SEC) under the following conditions.

Liquid chromatography
Column: TSKgel G3000SWXL (TOSOH)
Mobile phase: 50 mM phosphate buffer (pH7.0)+300 mM potassium chloride
Flow rate: 0.5 ml/min
Detection: 220 nm
Sample injection volume: 10 μl
Column temperature: room temperature
Sample temperature: 5° C.

Figure 4:
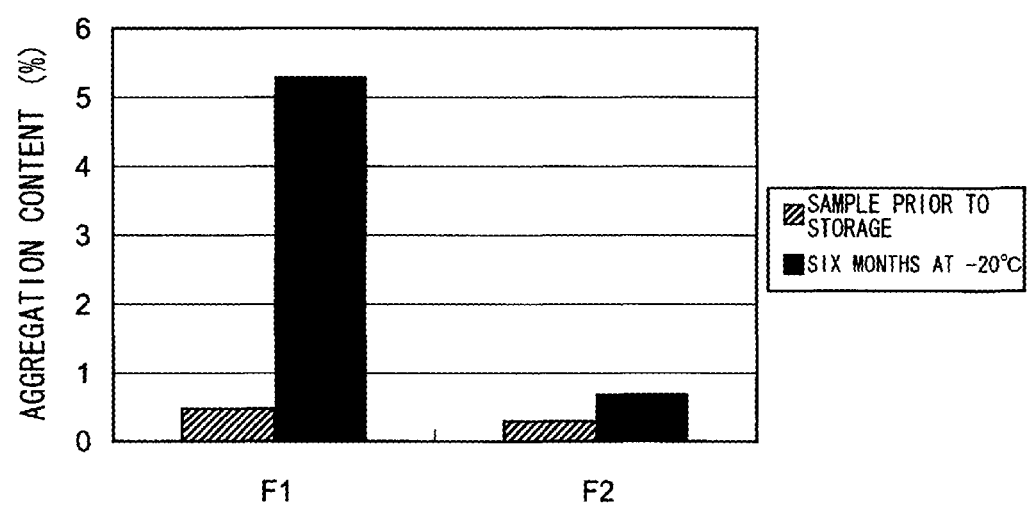
FIG. 4 is a graph showing the stabilizing effect of meglumine on long-term storage of single-chain diabody-type sc(Fv)2 at low-temperature (at −20° C. for six months).

FIG. 4 shows the aggregate content in the samples prior to storage and after six months of storage at −20° C., which were analyzed by SEC. While the increase of aggregate after six months of storage at −20° C. was 4.8% in F1 without meglumine, the increase of aggregate could be suppressed to 0.4% in F2 containing meglumine as a stabilizer. This Example demonstrates that meglumine has the effect of stabilizing proteins even in a frozen state.

Example 5

Stabilization Effect of Meglumine on the Humanized Bispecific Antibody hA69-KQ/hB26-PF/hAL-AQ Formulation (AF1, AF2, and AF3) were prepared from the purified humanized bispecific antibody hA69-KQ/hB26-PF/hAL-AQ according to the solution conditions described below. The humanized bispecific antibody comprising hA69-KQ/hB26-PF/hAL-AQ is an IgG4-type antibody comprising the first H chain variable region shown in SEQ ID NO: 49 (hA69-KQ), the second H chain variable region shown in SEQ ID NO: 50 (hB26-PF), and the L chain variable region shown in SEQ ID NO: 51 (hAL-AQ) that are shared by both H chains.
AF1: 20 mM histidine-HCl, 50 mM NaCl, pH5.8, 120 mg/ml hA69-KQ/hB26-PF/hAL-AQ
AF2: 20 mM histidine-HCl, 50 mM NaCl, 200 mM meglumine, pH5.8, 120 mg/ml hA69-KQ/hB26-PF/hAL-AQ
AF3: 20 mM histidine-HCl, 50 mM NaCl, 200 mM arginine-HCl, pH5.8, 120 mg/ml hA69-KQ/hB26-PF/hAL-AQ These samples were stored at room temperature (25° C.) for two months. The aggregate content in the samples prior to storage (initial) and in the samples after two months of storage at 25° C. (25° C.-2M) were analyzed by gel filtration chromatography (SEC) under the following conditions. In the measurement, AF 1, AF2, and AF3 were diluted to 1 mg/ml with the mobile phase of SEC. The diluted samples were analyzed.
Liquid chromatography
Column: TSKgel G3000SWXL (TOSOH)
Mobile phase: 50 mM phosphate buffer (pH7.0)+300 mM potassium chloride
Flow rate: 0.5 ml/min
Detection: 220 nm
Sample injection volume: 10 μl (120 mg/ml solutions diluted to 1 mg/ml with the mobile phase were injected)
Column temperature: room temperature
Sample temperature: 5° C.

Figure 5:
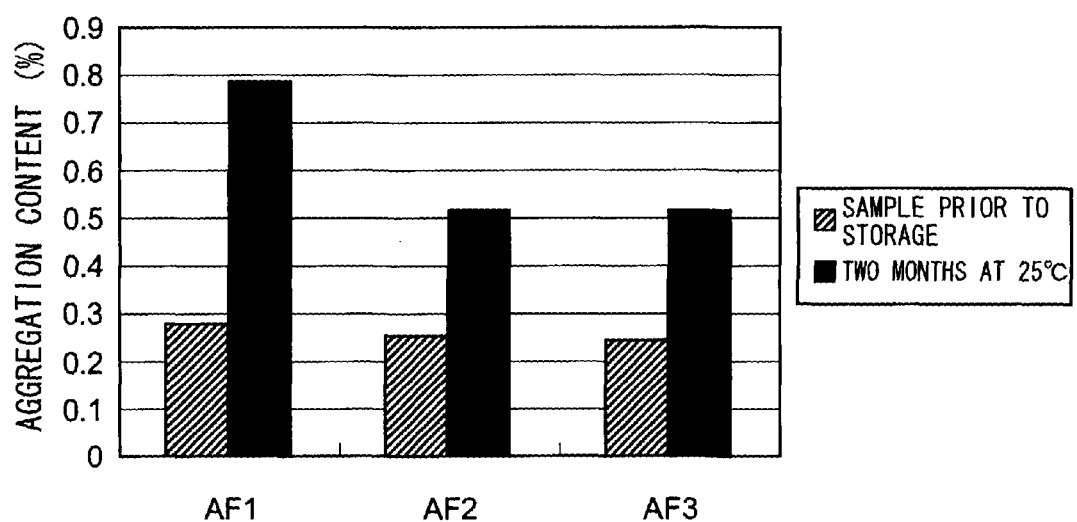
FIG. 5 is a graph showing the stabilizing effect of meglumine on long-term storage of humanized bispecific antibody at a room temperature (at 25° C. for two months).
Figure 6:
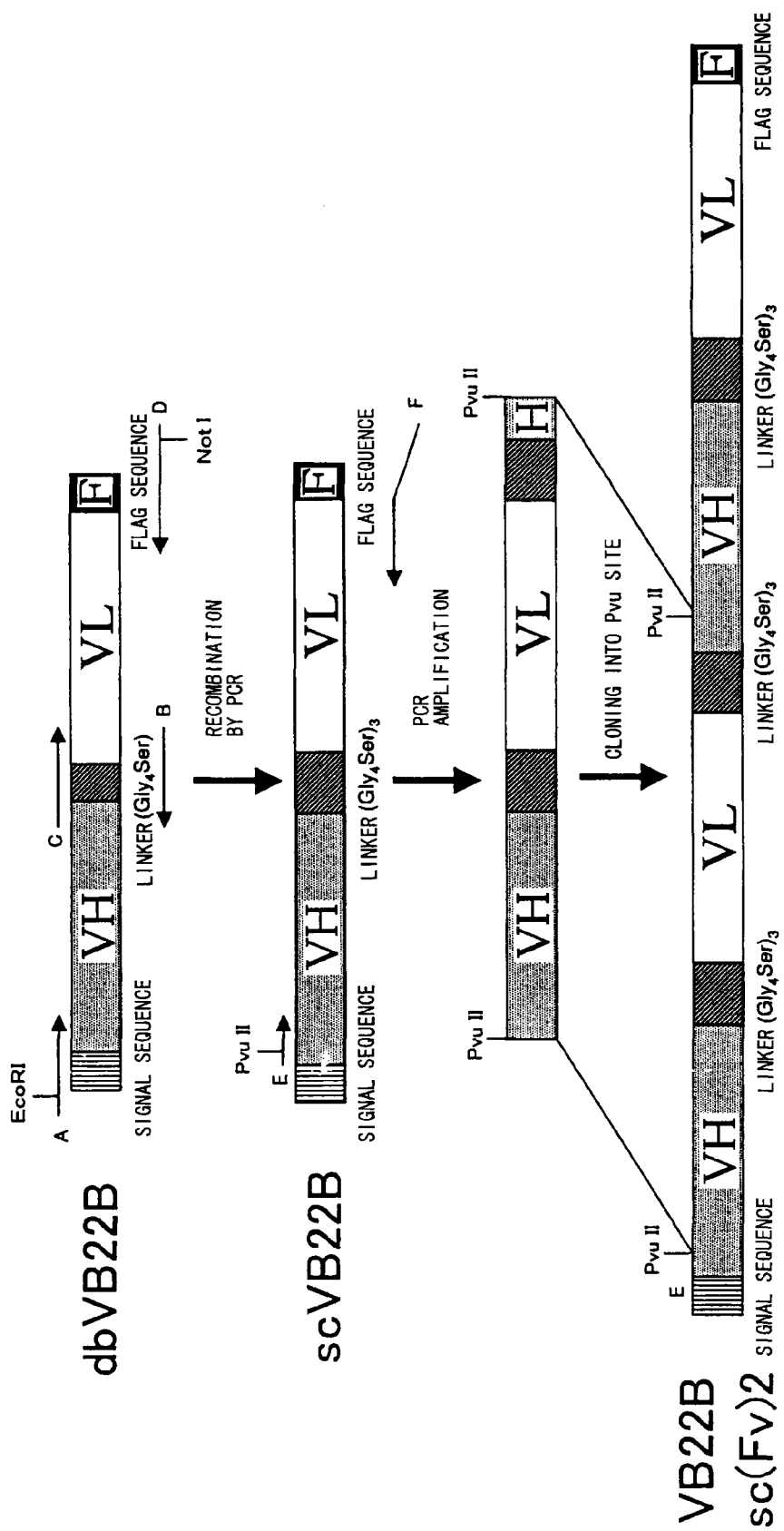
FIG. 6 is a diagram showing the production process for single-chain antibody sc(Fv)2.

FIG. 5 shows the aggregate content in samples prior to storage and samples after two months of storage at 25° C., which were analyzed by SEC. While the aggregate increase after six months of storage at 25° C. was 0.51% in AF1 without any stabilizer, the aggregate increase could be suppressed to 0.26% in AF2 containing meglumine as a stabilizer. The aggregate increase was 0.27% in AF3 containing arginine as a stabilizer. Thus, as compared to arginine, meglumine was found to have equivalent or greater stabilizing effect. Furthermore, meglumine was also found to have the stabilizing effect in solutions containing high concentration (120 mg/ml) of humanized bispecific antibody hA69-KQ/hB26-PF/hAL-AQ; as similarly described in Example 3. Thus, meglumine was demonstrated to have the effect of stabilizing not only IgG and sc(Fv)2 but also bispecific IgQ indicating that it can be commonly used as a protein stabilizer.

Reference Examples of the method for preparing sc(Fv)2 antibodies of the present invention (hVB22B, mVB22B, and 2D7) are described below. However, the present invention is not limited to the Reference Examples.

Reference Example 1

Preparation of Anti-Human Mp1 Antibodies 1.1 Establishment of Mp1-Expressing BaF3 Cell Lines
BaF3 cell lines expressing the full-length Mp1 gene were established to obtain cell lines that proliferate in a TPO-dependent manner.

A full-length human Mp1 cDNA (Palacios, R. et al., Cell, 41, 727-734 (1985)) (GenBank accession NO. NM_005373) was amplified by PCR. The cDNA was cloned into a pCOS2 expression vector to construct pCOS2-hMp1full. The expression vector pCOS2 was constructed by removing the DHFR gene expression region from pCHOI (Hirata, Y. et al., FEBS Letter, 356, 244-248 (1994)), where the expression region of the neomycin resistance gene HEF-VH-gγ1 (Sato, K. et al., Mol Immunol., 31, 371-381 (1994)) is inserted.

The cynomolgus monkey Mp1 cDNA (SEQ ID NO: 7) was cloned from total RNA extracted from the bone marrow cells of cynomolgus monkey, using a SMART RACE cDNA Amplification Kit (Clontech). The resulting cynomolgus monkey cDNA was inserted into pCOS2 to construct pCOS2-monkeyMp1full.

Then, the full-length mouse Mp1 cDNA (GenBank accession NO. NM_010823) was amplified by PCR, and inserted into pCOS2 to construct pCOS2-mouseMp1full.

Each vector (20 μg) prepared as described above was mixed with BaF3 cells ($1\times10^7$ cells/mL) suspended in PBS in Gene Pulser cuvettes. This mixture was then pulsed at 0.33 kV and 950 μFD using a Gene Pulser II (Bio-Rad). The BaF3 cells introduced with the above DNAs by electroporation were added to RPMI 1640 medium (Invitrogen) containing 1 ng/mL mouse interleukin 3 (hereinafter abbreviated as mIL-3; Peprotech), 500 μg/mL Geneticin (Invitrogen), and 10% FBS (Invitrogen), and selected to establish a human Mp1-expressing BaF3 cell line (hereinafter abbreviated as "BaF3-human Mp1"), monkey Mp1-expressing BaF3 cell line (hereinafter abbreviated as BaF3-monkey Mp1), and mouse Mp1-expressing BaF3 cell line (hereinafter abbreviated as "BaF3-mouse Mp1"). Following selection, these cells were cultured and maintained in RPMI 1640 containing 1 ng/mL rhTPO (R&D) and 10% FBS.

1.2 Establishment of Mp1-Expressing CHO Cell Lines
CHO cell lines expressing the full-length Mp1 gene were established to obtain cell lines to be used for assessing binding activity by flow cytometry.

First, the DHFR gene expression site from pCHOI was inserted into pCXN2 (Niwa, H. et al., Gene, 108, 193-199 (1991)) at the HindIII site to prepare a pCXND3 expression vector. The respective Mp1 genes were amplified by PCR using pCOS2-hMp1full, pCOS2-monkeyMp1full, and pCOS2-mouseMp1full as templates, and primers with a His-tag sequence. The PCR products were cloned into pCXND3 to construct pCXND3-hMp1-His, pCXND3-monkey Mp1-His, and pCXND3-mouse Mp1-His, respectively.

Vectors thus prepared (25 µg each) were mixed with a PBS suspension of CHO-DG44 cells ($1 \times 10^7$ cells/mL) in Gene Pulser cuvettes. The mixture was then pulsed at 1.5 kV and 25 µFD using Gene Pulser II (Bio-Rad). The CHO cells introduced with these DNAs by electroporation were added to CHO-S-SFMII medium (Invitrogen) containing 500 µg/mL Geneticin and 1×HT (Invitrogen). A human Mp1-expressing CHO cell line (hereinafter abbreviated as "CHO-human Mp1"), monkey Mp1-expressing CHO cell line (hereinafter abbreviated as "CHO-monkey Mp1"), and mouse Mp1-expressing CHO cell line (hereinafter abbreviated as "CHO-mouse Mp1") were established through selection.

1.3 Preparation of Soluble Human Mp1 Protein

To prepare soluble human Mp1 protein, an expression system using insect Sf9 cells for production and secretion of the protein was constructed as described below.

A DNA construct encoding the extracellular region of human Mp1 (Gln 26 to Trp 491) with a downstream FLAG tag was prepared. The construct was inserted into a pBACSurf-1 Transfer Plasmid (Novagen) between the PstI and SmaI sites to prepare pBACSurf1-hMp1-FLAG. Then, Sf9 cells were transformed with 4 µg of pBACSurf1-hMp1-FLAG using the Bac-N-Blue Transfection Kit (Invitrogen). The culture supernatant was collected after a three-day incubation. Recombinant virus was isolated by plaque assays. The prepared virus stock was used to infect Sf9 cells, and the culture supernatant was collected.

Soluble human Mp1 protein was purified from the obtained culture supernatant as described below. The culture supernatant was loaded onto a Q Sepharose Fast Flow (Amersham Biosciences) for adsorption, and the adsorbed protein was then eluted with 50 mM Na-phosphate buffer (pH7.2) containing 0.01% (v/v) Tween 20 and 500 mM NaCl. After the eluates were loaded onto a FLAG M2-Agarose (Sigma-Aldrich) for adsorption, the protein adsorbed was eluted with 100 mM glycine-HCl buffer (pH3.5) containing 0.01% (v/v) Tween 20. Immediately after elution, the fraction obtained was neutralized with 1 M Tris-HCl Buffer (pH8.0) and the buffer was exchanged with PBS(-) and 0.01% (v/v) Tween 20 using PD-10 columns (Amersham Biosciences). The purified soluble Mp1 protein was referred to as "shMp1-FLAG".

1.4 Preparation of Human Mp1-IgG Fc Fusion Protein

Human fusion protein Mp1-IgG Fc gene was prepared according to the method by Bennett et al. (Bennett, B. D. et al., J. Biol. Chem. 266, 23060-23067 (1991)). A nucleotide sequence encoding the extracellular region of human Mp1 (Gln 26 to Trp 491) was linked to a nucleotide sequence encoding the Fc region of human IgG-γ1 (a region downstream of Asp 216). A BstEII sequence (amino acids: Val-Thr) was attached to the junction as a fusion linker between these two regions. A 19-amino acid signal peptide derived form human IgG H chain variable region was used as the signal sequence. The resulting human fusion protein Mp1-IgG Fc gene was cloned into pCXND3 to construct pCXND3-hMp1-Fc.

The vector thus prepared (25 µg) was mixed with a PBS suspension of CHO-DG44 cells ($1 \times 10^7$ cells/mL) in Gene Pulser cuvettes. The mixture was then pulsed at 1.5 kV and 25 µFD using Gene Pulser II (Bio-Rad). The CHO cells introduced with the DNA by electroporation were added to CHO-S-SFMII medium containing 500 µg/mL Geneticin and 1×HT (Invitrogen). shMPL-Fc-expressing CHO cell line (CHO-hMp1-Fc) was then established through selection.

Human Mp1-IgG Fc fusion protein was purified from the culture supernatant as described below.

The culture supernatant was loaded onto a Q Sepharose Fast Flow (Amersham Biosciences) for adsorption, and then the adsorbed protein were eluted with 50 mM Na-phosphate buffer (pH7.6) containing 0.01% (v/v) Tween 20 and 1 M NaCl. After the eluates were loaded onto a HiTrap protein G HP column (Amersham Biosciences) for adsorption, the adsorbed protein was eluted with 0.1 M glycine-HCl buffer (pH2.7) containing 150 mM NaCl and 0.01% (v/v) Tween 20. Immediately after elution, the obtained fraction was neutralized with 1 M Tris-HCl Buffer (pH8.0) and the buffer was exchanged with PBS(-) and 0.01% (v/v) Tween 20 using PD-10 columns (Amersham Biosciences). The purified soluble Mp1 protein was referred to as "hMp1-Fc".

1.5 Immunization with shMp1-FLAG or BaF3-human Mp1 and hybridoma selection

MRL/MpJUmmCrj-1pr/1pr mice (hereinafter abbreviated as "MRL/1pr mice"; purchased from Charles River, Japan) were immunized; the primary immunization was carried out at eight weeks of age. For every single mouse, an emulsion containing 100 µg of shMPL-FLAG combined with Freund's complete adjuvant (H37 Ra; Beckton Dickinson), was administered subcutaneously as the primary injection. As a booster injection, an emulsion containing shMPL-FLAG (50 µg per mouse) combined with Freund's incomplete adjuvant (Beckton Dickinson) was administered subcutaneously. Three mice which have been immunized six times in total were subjected to a final injection of shMPL-FLAG (50 µg per mouse) through the caudal vein. Cell fusion was achieved by mixing the mouse myeloma P3-X63Ag8U1 cells (P3U1; purchased from ATCC) and mouse splenocytes using polyethylene glycol 1500 (Roche Diagnostics). Hybridoma selection in HAT medium began the following day and culture supernatants were obtained. Screening was carried out by ELISA, using immunoplates immobilized with shMp1-FLAG or hMp1-Fc and the assayed cell growth activity of BaF3-human Mp1 as an index. In addition, Balb/C mice were immunized eleven times in total by administering BaF3-human Mp1 ($1.0 \times 10^7$ cells per mouse) intraperitoneally over a period of one week to five months. Hybridomas were similarly prepared by cell fusion, and screened using the assayed cell growth activity of BaF3-human Mp1 as an index. Positive clones were isolated as single clones by limiting dilution and then cultured in a large scale. The culture supernatants were collected.

1.6 Analyses of Anti-Human Mp1 Antibodies

Antibody concentrations were determined by carrying out a mouse IgG sandwich ELISA using goat anti-mouse IgG (gamma) (ZYMED) and alkaline phosphatase-goat anti-mouse IgG (gamma) (ZYMED), generating a calibration curve by GraphPad Prism (GraphPad Software; USA), and calculating the antibody concentrations from the calibration curve. Commercially available antibodies of the same isotype were used as standards.

Antibody isotypes were determined by antigen-dependent ELISA using isotype-specific secondary antibodies. hMp1-Fc was diluted to 1 µg/mL with a coating buffer (0.1 mM NaHCO$_3$, pH9.6) containing 0.02% (w/v) NaN$_3$, and then added to ELISA plates. The plates were incubated overnight at 4° C. for coating. The plates were blocked with a diluent buffer (50 mM Tris-HCl (pH8.1) containing 1 mM MgCl$_2$, 150 mM NaCl, 0.05% (v/v) Tween 20, 0.02% (w/v) NaN$_3$, 1% (w/v) BSA). After the addition of hybridoma culture supernatants, the plates were allowed to stand at room temperature for 1 hr. After washing with a rinse buffer (0.05% (v/v) Tween 20 in PBS), alkaline phosphatase-labeled isotype-specific secondary antibodies were added to the plates. Then, the plates were allowed to stand at room temperature for 1 hr. Color development was carried out using SIGMA104 (Sigma-Aldrich) diluted to 1 mg/mL with a substrate buffer (50 mM NaHCO$_3$, pH9.8) containing 10 mM MgCl$_2$, and absorbance was measured at 405 nm using Benchmark Plus (Bio-Rad).

The binding activities of an antibody to shMp1-FLAG and hMPL-Fc were determined by ELISA. ELISA plates were coated with 1 µg/mL of purified shMp1-FLAG or hMPL-Fc, and blocked with a diluent buffer. Hybridoma culture supernatants were added to the plates, and the plates were allowed to stand at room temperature for 1 hr. Then, alkaline phosphatase-labeled anti-mouse IgG antibodies (Zymed) were added to the plates. Color development was similarly carried out using the above method. Following a one-hour coloring reaction at room temperature, absorbance was measured at 405 nm and EC$_{50}$ values were computed using GraphPad Prism.

CHO-human Mp1 cells and CHO-monkey Mp1 cells were harvested, and suspended in FACS Buffer (1% FBS/PBS) to a final concentration of 1×10$^6$ cells/mL. The suspensions were aliquoted into Multiscreen (Millipore) at 100 µl/well, and the culture supernatants were removed by centrifugation. Culture supernatants diluted to 5 µg/mL were added to the plates and incubated on ice for 30 min. The cells were washed once with FACS buffer, and incubated on ice for 30 min following the addition of an FITC-labeled anti-mouse IgG antibody (Beckman Coulter). After incubation, the mixture was centrifuged at 500 rpm for 1 min. The supernatants were removed, and then the cells were suspended in 400 µL of FACS buffer. The samples were analyzed by flow cytometry using EPICS ELITE ESP (Beckman Coulter). An analysis gate was set on the forward and side scatters of a histogram to include viable cell populations.

Agonistic activities of an antibody were evaluated using BaF3-human Mp1 and BaF3-monkey Mp1 which proliferate in a TPO-dependent manner. Cells of each cell line were suspended at 4×10$^5$ cells/ml in RPMI 1640/10% FBS (Invitrogen), and each suspension was aliquoted into a 96-well plate at 60 µl/well. A 40-µL aliquot of rhTPO (R&D) and hybridoma culture supernatants prepared at various concentrations was added into each well. The plates were then incubated at 37° C. under 5% CO$_2$ for 24 hr. A 10-µL aliquot of the Cell Count Reagent SF (Nacalai Tesque) was added into each well. After incubation for 2 hr, absorbance was measured at 450 nm (and at 655 nm as a control) using a Benchmark Plus. EC$_{50}$ values were calculated using GraphPad Prism.

The above analysis yielded a total of 163 clones of mouse monoclonal antibodies that bind to human Mp1.

Among the anti-human Mp1 antibodies to be described, TA136 was established from mice immunized with BaF3-human Mp1 and the others were established from mice immunized with shMp1-Flag.

1.7 Purification of Anti-Human Mp1 Antibodies

Anti-human Mp1 antibodies were purified from hybridoma culture supernatants as described below.

After the culture supernatants were loaded onto HiTrap protein G HP columns (Amersham Biosciences) for adsorption, the antibodies were eluted with 0.1 M glycine-HCl (pH2.7) Buffer. Immediately after elution, the fractions were neutralized with 1 M Tris-HCl Buffer (pH9.0), and dialyzed against PBS to replace the buffer for one day.

1.8 Determination of Epitopes for the Anti-Human Mp1 Antibody VB22B

Since the anti-human Mp1 antibody VB22B can be used for Western blotting, a GST-fusion protein containing a partial sequence of human Mp1 was constructed for VB22B epitope analysis. MG1 (Gln26 to Trp491) and MG2 (Gln26 to Leu274) regions were each amplified by PCR, and cloned into pGEX-4T-3 (Amersham Biosciences) to be expressed as GST fusion proteins. The resulting plasmid DNAs were transformed into DH5α to give transformants. A final concentration of 1 mM IPTG was added to the transformants in their logarithmic growth phase to induce the expression of GST fusion proteins. The bacterial cells were harvested after two hours of incubation. The cells were lysed by sonication. The lysates were centrifuged in XL-80 Ultracentrifuge (Beckman, Rotor 70.1Ti) at 35,000 rpm for 30 min. The culture supernatants were removed, and then the fusion proteins were purified using GST Purification Modules (Amersham Biosciences). The samples were separated by 10%-SDS-PAGE, and then transferred onto a PVDF membrane. The membrane was analyzed by the murine antibody VB22B in Western blotting. VB22B was found to recognize both MG-1 and MG-2, indicating that the VB22B epitope is located in the (Gln26 to Leu274) region.

Then, GST fusion proteins containing the respective regions of human Mp1: MG3 (Gln26 to Ala189), MG4 (Gln26 to Pro106), MG5 (Gln26 to Glu259), and MG6 (Gln26 to Gly245) were prepared and analyzed by Western blotting using the same procedure described above. VB22B was found to recognize MG5 and MG6, but not MG3 and MG4. This suggests that the VB22B epitope is located within the (Ala189 to Gly245) region. In addition, GST was fused with MG7 (Gln26 to Ala231) and MG8 (Gln26 to Pro217) to prepare GST fusion proteins. VB22B recognized MG7 but not MG8, suggesting that the VB22B epitope is located in the (Gln217 to Ala231) region. Furthermore, GST fusion protein containing MG10 (Gln213 to Ala231) was recognized by VB22B, suggesting that the VB22B epitope is located within the limited region of 19 amino acids between Gln213 and Ala231.

1.9 Kinetic Analyses of the Antigen-Antibody Reaction for Anti-Human Mp1 Antibody VB22B Since the anti-human Mp1 antibody VB22B binds to soluble recombinant Mp1, kinetic analyses of the antigen-antibody reaction between VB22B IgG and human Mp1-IgG Fc fusion protein were carried out as described in Example 1.4. The Sensor Chip CM5 (Biacore) was placed in Biacore 2000 (Biacore), and human Mp1-IgG Fc fusion protein was immobilized onto the chip by amine-coupling methods. Then, 1.25 to 20 µg/mL of VB22B IgG solution was prepared using HBS-EP Buffer (Biacore), and injected over the chip surface for 2 min to reveal the binding region. Then, HBS-EP Buffer was injected over the chip surface for 2 min to reveal the dissociation region. VB22B IgG bound to the human Mp1-IgG Fc fusion protein on the sensor chip was removed by injecting 10 mM NaOH over the sensor chip for 15 sec, and the chip was recovered. HBS-EP Buffer was used as the running buffer, and the flow rate was 20 µL/min. Using the BIAevaluation Version 3.1 (Biacore) software, the reaction rate constant at each concentration was calculated from the sensorgrams. The dissociation constant (KD) for VB22B IgG was determined to be 1.67±0.713×10$^{-9}$ M.

Reference Example 2

Preparation of Single-Chain Anti-Human Mp1 Antibodies

Among the prepared anti-human Mp1 antibodies, 23 types of antibodies, which exhibit higher binding activities and agonistic activities, were selected to construct expression systems for single-chain antibodies using genetic engineering techniques. An exemplary method for constructing a single-chain antibody derived from the anti-human Mp1 antibody VB22B is described below.

2.1 Cloning of the Anti-Human Mp1 Antibody Variable Region

The variable region was amplified by RT-PCR using total RNA extracted from hybridomas producing anti-human Mp1 antibodies. Total RNA was extracted from 1×10$^7$ hybridoma cells using the RNeasy Plant Mini Kit (QIAGEN).

A 5'-terminal fragment of the gene was amplified from 1 µg of total RNA by the SMART RACE cDNA Amplification Kit (Clontech), using a synthetic oligonucleotide MHC-IgG2b (SEQ ID NO: 8) complementary to mouse IgG2b constant region or a synthetic oligonucleotide kappa (SEQ ID NO: 9) complementary to mouse ic chain constant region. Reverse transcription was carried out at 42° C. for 1.5 hr.

The composition of the PCR reaction solution (50 µL in total) is shown below.

| | |
|---|---|
| 10x Advantage 2 PCR Buffer (Clontech) | 5 µL |
| 10x Universal Primer A Mix (Clontech) | 5 µL |
| dNTPs (dATP, dGTP, dCTP, and dTTP) (Clontech) | 0.2 mM |
| Advantage 2 Polymerase Mix (Clontech) | 1 µL |
| Reverse transcription product | 2.5 µL |
| Synthetic oligonucleotide, MHC-IgG2b or kappa | 10 pmol |

The PCR reaction conditions were:
94° C. (initial temperature) for 30 sec;
five cycles of 94° C. for 5 sec and 72° C. for 3 min;
five cycles of 94° C. for 5 sec, 70° C. for 10 sec, and 72° C. for 3 min;
25 cycles of 94° C. for 5 sec, 68° C. for 10 sec, and 72° C. for 3 min; and final extension was at 72° C. for 7 min.

The PCR products were purified from agarose gel using the QIAquick Gel Extraction Kit (QIAGEN), and cloned into a pGEM-T Easy Vector (Promega). The nucleotide sequence was then determined using the ABI 3700 DNA Analyzer (Perkin Elmer).

The nucleotide sequence of cloned VB22B H chain variable region (hereinafter abbreviated as "VB22B-VH") is shown in SEQ ID NO: 10, and its amino acid sequence is shown in SEQ ID NO: 11. The nucleotide sequence of the L chain variable region (hereinafter abbreviated as "VB22B-VL") is shown in SEQ ID NO: 12, and its amino acid sequence is shown in SEQ ID NO: 13.

2.2 Preparation of Expression Vectors for Anti-Human Mp1 Diabodies

The gene encoding VB22B single-chain Fv (hereinafter abbreviated as "VB22B diabody") containing a five-amino acid linker sequence was constructed, by linking a nucleotide sequence encoding a (Gly$_4$Ser)$_1$ linker to the VB22B-VH-encoding gene at its 3' end and to the VB22B-VL-encoding gene at its 5' end; both of which have been amplified by PCR.

The VB22B-VH forward primer, 70•115HF, (SEQ ID NO: 14) was designed to contain an EcoRI site. The VB22B-VH reverse primer, 33•115HR, (SEQ ID NO: 15) was designed to hybridize to a DNA encoding the C terminus of VB22B-VH, and to have a nucleotide sequence encoding the (Gly$_4$Ser)$_1$ linker and a nucleotide sequence hybridizing to the DNA encoding the N terminus of VB22B-VL. The VB22B-VL forward primer, 33•115LF, (SEQ ID NO: 16) was designed to have a nucleotide sequence encoding the N terminus of VB22B-VL, a nucleotide sequence encoding the (Gly$_4$Ser)$_1$ linker, and a nucleotide sequence encoding the C terminus of VB22B-VH. The VB22B-VL reverse primer, 33•115LR, (SEQ ID NO: 17) was designed to hybridize to a DNA encoding the C terminus of VB22B-VL and to have a nucleotide sequence encoding a FLAG tag (Asp Tyr Lys Asp Asp Asp Lys/SEQ ID NO: 18) and a NotI site.

In the first round of PCR, two PCR products: one containing VB22B-VH and a linker sequence, and the other containing VB22B-VL and the identical linker sequence, were synthesized by the procedure described below.

The composition of the PCR reaction solution (50 µL in total) is shown below.

| | |
|---|---|
| 10x PCR Buffer (TaKaRa) | 5 µL |
| dNTPs (dATP, dGTP, dCTP, and dTTP) (TaKaRa) | 0.4 mM |
| DNA polymerase TaKaRa Ex Taq (TaKaRa) | 2.5 units |
| pGEM-T Easy vector comprising VB22B-VH or VB22B-VL gene | 10 ng |
| Synthetic oligonucleotides, 70 · 115HF and 33 · 115HR, or 33 · 115LF and 33 · 115LR | 10 pmol |

The PCR reaction conditions were:
94° C. (initial temperature) for 30 sec;
five cycles of: 94° C. for 15 sec and 72° C. for 2 min;
five cycles of 94° C. for 15 sec and 70° C. for 2 min;
28 cycles of 94° C. for 15 sec and 68° C. for 2 min;
and final extension was at 72° C. for 5 min.

After the PCR products of about 400 bp were purified from agarose gel using the QIAquick Gel Extraction Kit (QIAGEN), the second-round PCR was carried out using aliquots of the respective PCR products according to the protocol described below.

The composition of the PCR reaction solution (50 µL in total) is shown below.

| | |
|---|---|
| 10x PCR Buffer (TaKaRa) | 5 µL |
| dNTPs (dATP, dGTP, dCTP, and dTTP) (TaKaRa) | 0.4 mM |
| DNA polymerase TaKaRa Ex Taq (TaKaRa) | 2.5 unit |
| First-round PCR products (two types) | 1 µL |
| Synthetic oligonucleotides, 70 · 115HF and 33 · 115LR | 10 pmol |

The reaction conditions were:
94° C. (initial temperature) for 30 sec;
five cycles of 94° C. for 15 sec and 72° C. for 2 min;
five cycles of 94° C. for 15 sec and 70° C. for 2 min;
28 cycles of 94° C. for 15 sec and 68° C. for 2 min;
and final extension was at 72° C. for 5 min.

The PCR products of about 800 bp were purified from agarose gel using the QIAquick Gel Extraction Kit (QIAGEN), and then digested with EcoRI and NotI (both from TaKaRa). The resulting DNA fragments were purified using the QIAquick PCR Purification Kit (QIAGEN), and then cloned into pCXND3 to prepare pCXND3-VB22B db.

2.3 Preparation of Expression Vectors for Anti-Human Mp1 Antibody sc(Fv)2

To prepare expression plasmids for the modified antibody [sc(Fv)2] comprising two units of H chain variable region and two units of L chain variable region derived from VB22B, the above-described pCXND3-VB22B db was modified by PCR using the procedure shown below.

First, PCR was carried out to amplify (a) the VB22B-VH-encoding gene in which a nucleotide sequence encoding a 15-amino acid linker (Gly$_4$Ser)$_3$ was added to its 3' end; and (b) the VB22B-VL-encoding gene containing the identical linker nucleotide sequence added to its 5' end. The desired construct was prepared by linking these amplified genes. Three new primers were designed in this construction process. The VB22B-VH forward primer, VB22B-fpvu, (primer A; SEQ ID NO: 19) was designed to have an EcoRI site at its 5' end and to convert Gln2 and Leu23 of VB22B db into a PvuII site. The VB22B-VH reverse primer, sc-rL15, (primer B; SEQ ID NO: 20) was designed to hybridize to a DNA encoding the C terminus of VB22B-VH, and to have a nucleotide sequence encoding the (Gly$_4$Ser)$_3$ linker, as well as a nucleotide sequence hybridizing to a DNA encoding the N terminus of VB22B-VL. The VB22B-VL forward primer, sc-fL15, (primer C; SEQ ID NO: 21) was designed to have a nucleotide sequence encoding the N terminus of VB22B-VL, a nucleotide sequence encoding the (Gly$_4$Ser)$_3$ linker, and a nucleotide sequence encoding the C terminus of VB22B-VH.

In the first-round PCR, two PCR products: one comprising VB22B-VH and a linker sequence, and the other comprising VB22B-VL and the identical linker sequence, were synthesized by the procedure described below.

The composition of the PCR reaction solution (50 μL in total) is shown below.

| | |
|---|---|
| 10x PCR Buffer (TaKaRa) | 5 μL |
| dNTPs (dATP, dGTP, dCTP, and dTTP) (TaKaRa) | 0.4 mM |
| DNA polymerase TaKaRa Ex Taq (TaKaRa) | 2.5 units |
| pCXND3-VB22B db | 10 ng |
| Synthetic oligonucleotides, VB22B-fpvu, sc-rL15 or sc-fL15, and 33 · 115LR (primer D) | 10 pmol |

The reaction conditions were:
94° C. (initial temperature) for 30 sec;
five cycles of 94° C. for 15 sec and 72° C. for 2 min;
five cycles of 94° C. for 15 sec and 70° C. for 2 min;
28 cycles of 94° C. for 15 sec and 68° C. for 2 min;
and final extension was at 72° C. for 5 min.

After the PCR products of about 400 bp were purified from agarose gel using the QIAquick Gel Extraction Kit (QIAGEN), the second-round PCR was carried out using aliquots of the respective PCR products according to the protocol described below.

The composition of the PCR reaction solution (50 μL in total) is shown below.

| | |
|---|---|
| 10x PCR Buffer (TaKaRa) | 5 μL |
| dNTPs (dATP, dGTP, dCTP, and dTTP) (TaKaRa) | 0.4 mM |
| DNA polymerase TaKaRa Ex Taq (TaKaRa) | 2.5 units |
| First-round PCR product (two types) | 1 μL |
| Synthetic oligonucleotide, 70 · 115HF and 33 · 115LR | 10 pmol |

The reaction conditions were:
94° C. (initial temperature) for 30 sec;
five cycles of 94° C. for 15 sec and 72° C. for 2 min;
five cycles of 94° C. for 15 sec and 70° C. for 2 min;
28 cycles of 94° C. for 15 sec and 68° C. for 2 min;
and final extension was at 72° C. for 5 min.

The PCR products of about 800 bp were purified from agarose gel using the QIAquick Gel Extraction Kit (QIAGEN), and then digested with EcoRI and NotI (both from TaKaRa). The resulting DNA fragments were purified using the QIAquick PCR Purification Kit (QIAGEN), and then cloned into pBacPAK9 (Clontech) to construct pBacPAK9-scVB22B.

A fragment to be inserted into the PvuII site of pBacPAK9-scVB22B was prepared. Specifically, the fragment has a PvuII recognition site at both ends and a nucleotide sequence, in which a gene encoding the VB22B-VH N-terminus is linked, via a (Gly$_4$Ser)$_3$ linker-encoding nucleotide sequence, to a gene encoding the amino acid sequence of an N terminus-deleted VB22B-VH linked to VB22B-VL via the (Gly$_4$Ser)$_3$ linker. Two primers were newly designed to prepare the fragment by PCR. The forward primer for the fragment of interest, Fv2-f (primer E; SEQ ID NO: 22), was designed to have a PvuII site at its 5' end and a VB22B-VH 5'-end sequence.

The reverse primer for the fragment of interest, Fv2-r (primer F; SEQ ID NO: 23), was designed to hybridize to a DNA encoding the C terminus of VB22B-VL, and to have a PvuII site, a nucleotide sequence encoding the (Gly$_4$Ser)$_3$ linker, and a nucleotide sequence hybridizing to a DNA encoding the N terminus of VB22B-VH. PCR was carried out using pBacPAK9-scVB22B as a template as described below.

The composition of the PCR reaction solution (50 μL in total) is shown below.

| | |
|---|---|
| 10x PCR Buffer (TaKaRa) | 5 μL |
| dNTPs (dATP, dGTP, dCTP, and dTTP) (TaKaRa) | 0.4 mM |
| DNA polymerase TaKaRa Ex Taq (TaKaRa) | 2.5 units |
| pBacPAK9-scVB22B | 10 μg |
| Synthetic oligonucleotide, Fv2-f and Fv2-r | 10 pmol |

The reaction conditions were:
94° C. (initial temperature) for 30 sec;
five cycles of 94° C. for 15 sec and 72° C. for 2 min;
five cycles of 94° C. for 15 sec and 70° C. for 2 min;
28 cycles of 94° C. for 15 sec and 68° C. for 2 min;
and final extension was at 72° C. for 5 min.

The PCR products of about 800 bp were purified from agarose gel using the QIAquick Gel Extraction Kit (QIAGEN), and then cloned into the pGEM-T Easy Vector (Promega). After sequencing, the plasmid was digested with PvuII (TaKaRa), and the fragment of interest was recovered. The recovered fragment was ligated to pBacPAK9-scVB22B pre-digested with PvuII (TaKaRa) to construct pBacPAK9-VB22B sc(Fv)2. After the resulting vector was digested with EcoRI and NotI (both from TaKaRa), the fragment of about 1,600 bp was purified from agarose gel using the QIAquick Gel Extraction Kit (QIAGEN). The fragment was then cloned into a pCXND3 expression vector to construct pCXND3-VB22B sc(Fv)2.

2.4 Expression of Single-Chain Anti-Human Mp1 Antibody in Animal Cells

A cell line stably expressing the single-chain antibody was prepared from CHO-DG44 cells as described below. Gene transfer was achieved by electroporation using a Gene Pulser II (Bio-Rad). An expression vector (25 μg) and 0.75 mL of CHO-DG44 cells suspended in PBS (1×10$^7$ cells/mL) were mixed. The resulting mixture was cooled on ice for 10 min, transferred into a cuvette, and pulsed at 1.5-kV and 25 μFD. After a ten-minute restoration period at room temperature, the electroporated cells were plated in CHO-S-SFMII medium (Invitrogen) containing 500 μg/mL Geneticin (Invitrogen). CHO cell lines expressing the single-chain antibody were established through selection. A cell line stably expressing VB22B sc(Fv)2 and its culture supernatants were obtained by this method.

The transient expression of the single-chain antibody was achieved using COS7 cells as described below. An expression vector (10 μg) and 0.75 mL of COS7 cells suspended in PBS (1×10$^7$ cells/mL) were mixed. The resulting mixture was cooled on ice for 10 min, transferred into a cuvette, and then pulsed at 1.5-kV and 25 μFD. After a ten-minute restoration period at room temperature, the electroporated cells were plated in DMEM/10% FBS medium (Invitrogen). The cells were incubated overnight and then washed with PBS. CHO-S-SFMII medium was added and the cells were cultured for about three days. The culture supernatants for preparing the VB22B diabody were thus prepared.

2.5 Quantitation of Single-Chain Anti-Human Mp1 Antibodies in Culture Supernatants The culture supernatant concentration of the single-chain anti-human Mp1 antibody transiently expressed in COS cells was determined using surface plasmon resonance. A sensor chip CM5 (Biacore) was placed in Biacore 2000 (Biacore). ANTI-FLAG®(R) M2 Monoclonal Antibody (Sigma-Aldrich) was immobilized onto the chip. An appropriate concentration of sample was injected over the chip surface at a flow rate of 5 mL/sec, and 50 mM diethylamine was used to dissociate the bound antibody. Changes in the mass during sample injection were recorded, and the sample concentration was calculated from the calibration curve prepared using the mass changes of a standard sample. db12E10 (see WO 02/33073 and WO 02/33072) was used as the diabody standard, and 12E10 sc(Fv)2 which has the same gene structure as that of sc(Fv)2 was used as the sc(Fv)2 standard.

2.6 Purification of Anti-Human Mp1 Diabodies and Single-Chain Antibodies

The culture supernatants of VB22B diabody-expressing COS7 cells or CHO cells was loaded onto an Anti-Flag M2 Affinity Gel (Sigma-Aldrich) column equilibrated with a 50 mM Tris-HCl buffer (pH7.4) containing 150 mM NaCl and 0.05% Tween 20. The absorbed antibodies were eluted with 100 mM glycine-HCl (pH3.5). The fractions eluted were immediately neutralized with 1 M Tris-HCl (pH8.0), and loaded onto a HiLoad 26/60 Superdex 200 pg (Amersham Biosciences) column for gel filtration chromatography. PBS/0.01% Tween 20 was used in the gel filtration chromatography.

VB22B sc(Fv)2 was purified from the culture supernatants of VB22B sc(Fv)2-expressing COS7 cells or CHO cells under the same conditions used for purifying the diabodies. A large-scale preparation of VB22B sc(Fv)2 was prepared by loading the CHO cell culture supernatants onto a Macro-Prep Ceramic Hydroxyapatite Type I (Bio-Rad) column equilibrated with a 20 mM phosphate buffer (pH6.8), and eluting the VB22B sc(Fv)2 in a stepwise manner with 250 mM phosphate buffer (pH6.8). The eluted fraction was concentrated on an ultrafilter, and then fractionated by gel filtration chromatography using a HiLoad 26/60 Superdex 200 pg (Amersham Biosciences) column, and a fraction corresponding to the molecular weight range of about 40 kD to 70 kD was obtained. The fraction was loaded onto an Anti-Flag M2 Affinity Gel column equilibrated with a 50 mM Tris-HCl buffer (pH7.4) containing 150 mM NaCl and 0.05% Tween 20. The absorbed antibody was eluted with 100 mM glycine-HCl (pH3.5). The eluted fraction was immediately neutralized with 1 M Tris-HCl (pH8.0), and loaded onto a HiLoad 26/60 Superdex 200 pg (Amersham Biosciences) column for gel filtration chromatography. 20 mM acetate buffer (pH6.0) containing 150 mM NaCl and 0.01% Tween 80 was used in the gel filtration chromatography. In each purification step, the presence of the diabody and sc(Fv)2 in the samples was confirmed by SDS-PAGE and Western blotting using an anti-Flag antibody (Sigma-Aldrich). Specifically, obtained fractions corresponding to each peak were subjected to the electrophoresis according to the method described by Laemli, and then stained using Coomassie Brilliant Blue. As a result, single band was detected apparently at about 29 kDa for the diabody; while single band was detected apparently at about 55 kDa for sc(Fv)2.

2.7 Binding Activity Analyses of Single-Chain Anti-Human Mp1 Antibodies by Flow Cytometry CHO-human Mp1, CHO-monkey Mp1, and CHO-mouse Mp1 cells were recovered and suspended in FACS buffer (1% FBS/PBS) to a final concentration of $1 \times 10^6$ cells/mL. Cell suspensions were aliquoted at 100-µL/well into the Multiscreen-HV Filter Plates (Millipore). After centrifugation, the supernatant was removed. An appropriate concentration of diabody or sc(Fv)2 was added into each well and incubated on ice for 30 min. The cells were washed once with 200 µL of FACS buffer, and incubated on ice for 30 min following the addition of 10 µg/mL ANTI-FLAG® M2 Monoclonal Antibody (Sigma-Aldrich). The cells were then washed once with 200 µL of FACS buffer, and a 100×-diluted FITC-labeled anti-mouse IgG antibody (Beckman Coulter) was added to the plate. The plate was incubated on ice for 30 min. After centrifugation, the supernatant was removed. The cells were suspended in 400 µL of FACS Buffer, and then analyzed by flow cytometry using EPICS ELITE ESP (Beckman Coulter). An analysis gate was set on the forward and side scatters of a histogram to include viable cell populations.

The binding activity of the purified VB22B sc(Fv)2 to various Mp1 molecules expressed in CHO cells was determined. VB22B sc(Fv)2 was found to specifically bind to CHO-human Mp1 and CHO-monkey Mp1 but not to the host cell CHO or CHO-mouse Mp1. This binding characteristic of VB22B sc(Fv)2 is comparable to those of VB22B IgG, indicating that the antibody binding site remains unaltered by converting whole IgG to minibody.

2.8 Humanization of Single-Chain Anti-Human Mp1 Antibody

Antibody sequence data for the humanization of VB22B sc(Fv)2 were obtained from the Kabat Database (ftp.ebi.ac.uk/pub/databases/kabat/), and homology searches were carried out independently for the H chain variable region and the L chain variable region. As a result, the H chain variable region was found to be highly homologous to DN13 (Smithson S. L. et al., Mol. Immunol. 36, 113-124 (1999)). The L chain variable region was found to be highly homologous to ToP027 (Hougs L. et al., J. Immunol. 162, 224-237 (1999)). Humanized antibodies were prepared by inserting a complementarity-determining region (hereinafter abbreviated as "CDR") into the framework regions (hereinafter abbreviated as "FR") of the above antibodies. The humanized antibody sc(Fv)2 was expressed in CHO-DG44 cells, and its agonistic activity was assessed using BaF3-human Mp1. The agonistic activity was used as an index to generate a humanized VB22B sc(Fv)2 which has agonistic activity equivalent to that of murine VB22B sc(Fv)2 by replacing one or more amino acids in its framework region.

Specifically, synthetic oligo-DNAs of approximately 50 nucleotides in length were designed as to make 20 of these nucleotides available for hybridization, and the synthetic oligo-DNAs were assembled by PCR to prepare genes that encode the respective variable regions. Using the resulting genes, sc(Fv)2 was similarly prepared by the method described in Example 2.3. The respective DNAs were cloned into a pCXND3 expression vector to construct expression vectors pCXND3-hVB22B p-z sc(Fv)2, pCXND3-hVB22B g-e sc(Fv)2, pCXND3-hVB22B e sc(Fv)2, pCXND3-hVB22B u2-wz4 sc(Fv)2, and pCXND3-hVB22B q-wz5 sc(Fv)2, to which the humanized VB22B sc(Fv)2 is inserted. The nucleotide sequences and the amino acid sequences of the fragments in each plasmid are shown below.

| Plasmid name | Nucleotide sequence | Amino acid sequence |
| --- | --- | --- |
| hVB22B p-z sc(Fv)2 | SEQ ID NO: 24 | SEQ ID NO: 25 |
| hVB22B g-e sc(Fv)2 | SEQ ID NO: 26 | SEQ ID NO: 27 |
| hVB22B e sc(Fv)2 | SEQ ID NO: 28 | SEQ ID NO: 29 |
| hVB22B u2-wz4 sc(Fv)2 | SEQ ID NO: 30 | SEQ ID NO: 1 |

| Plasmid name | Nucleotide sequence | Amino acid sequence |
| --- | --- | --- |
| hVB22B q-wz5 sc(Fv)2 | SEQ ID NO: 31 | SEQ ID NO: 32 |
| Murine VB22B sc(Fv)2 | SEQ ID NO: 33 | SEQ ID NO: 2 |

The plasmids were expressed in CHO-DG44 cells and the culture supernatants were recovered by the method described in Example 2.4. Since the humanized VB22B sc(Fv)2 does not contain a Flag tag, its purification from the culture supernatant was performed using a MG10-GST fusion protein. MG10 (Gln213 to Ala231) is one of the epitopes recognized by VB22B, as described in Example 1.8. The MG10-GST fusion protein was purified using Glutathione Sepharose 4B (Amersham Biosciences) according to the supplier's protocol. Then, the purified MG10-GST fusion protein was immobilized onto a HiTrap NHS-activated HP Column (Amersham Biosciences) to prepare an affinity column, according to the supplier's protocol. The culture supernatant of CHO cells expressing the humanized VB22B sc(Fv)2 was loaded onto the MGIO-GST fusion protein-immobilized column, which has been equilibrated with 50 mM Tris-HCl (pH7.4)/150 M NaCl/0.01% Tween 80. The adsorbed humanized VB22B sc(Fv)2 was eluted with 100 mM glycine-HCl (pH3.5)/0.01% Tween 80. Immediately after elution, the eluted fraction was neutralized with 1 M Tris-HCl (pH7.4), and was further subjected to gel filtration chromatography using a HiLoad 16/60 Superdex 200 pg (Amersham Biosciences). 20 mM citrate buffer (pH7.5) containing 300 mM NaCl and 0.01% Tween 80 was used in the gel filtration chromatography.

Reference Example 3

Production of Expression Vectors for 2D7 sc(Fv)2-Type Diabodies

As already described in WO 2004/033499, it has been demonstrated that modification of a 2D7 monoclonal antibody against HLA class I to a minibody (2D7 diabody) in which the heavy chain and light chain variable regions are linked with a 5-mer linker, dramatically increases cell death-inducing activity against myeloma cells. This 2D7 diabody was further modified to a sc(Fv)2 form, which is thought to be structurally more stable, and then the cell death inducing activity was compared with that of the conventional diabody (HL5).

To arrange the heavy chain variable region sequence (VH) and the light chain variable region sequence (VL) of the 2D7 antibody in the order of VH-VL-VH-VL, a DNA expression vector encoding 2D7sc(Fv)2 in which these sequences are linked by a 15-mer linker (GlyGlyGlyGlySerGlyGlyGlyGly-SerGlyGlyGlyGlySer(SEQ ID NO: 52 ) was produced by the following procedure.

2D7 diabody (HL5) expression vector produced according to the method of WO2004/033499 by linking VH-VL with a 5-mer linker (GlyGlyGlyGlySer(SEQ ID NO:43)), was used as a template for a PCR reaction using primer 2D7 DBH1 (SEQ ID NO: 34) and primer 2D7PA2 (SEQ ID NO: 35) to amplify fragment A. Similarly, a PCR reaction was performed using primer 2D7PA3 (SEQ ID NO: 36) and primer 2D7PA5 (SEQ ID NO: 37) to amplify fragment B. The obtained fragments A and B were mixed in the same tube, and the two fragments were linked by conducting a PCR-recombination reaction. This yielded the DNA fragment "2D7 diabody HL15-1" comprising a VH signal sequence at the N terminal, in which VH-VL is linked by a 15-mer linker.

Subsequently, using 2D7 diabody (HL5) expression vector as the template, a PCR reaction was performed using primer 2D7PA6 (SEQ ID NO: 38) and primer 2D7PA2 (SEQ ID NO: 35) to amplify fragment C. Similarly, a PCR reaction was performed using primer 2D7PA3 (SEQ ID NO: 36) and primer 2D7DBL2 (SEQ ID NO: 39) to amplify fragment D. The obtained fragments C and D were mixed in the same tube, and the two fragments were linked by conducting a PCR-recombination reaction. This yielded the DNA fragment "2D7diabody HL15-2" comprising a Flag-tag region at the C terminal, in which VH-VL is linked by a 15-mer linker.

The two DNA fragments obtained by the above-mentioned reactions, that is, "2D7 diabody HL15-1" DNA fragment and "2D7 diabody HL15-2" DNA fragment were digested using EcoRI-BamHI and BamHI-NotI, respectively, and both DNA fragments were inserted into expression vector pCXND3 that had been digested and cleaved using EcoRI-NotI. The nucleotide sequence of the inserted DNA was analyzed to confirm that the cDNA encoding signal-VH(15)VL(15)VH(15)VL-Flag has been inserted between EcoRI-NotI of pCXND3 as intended, and the construction of the 2D7sc(Fv)2 expression vector (pCXND3-2D7sc(Fv)2) was completed. The nucleotide sequence and the amino acid sequence of 2D7sc(Fv)2 are shown in SEQ ID NO: 40 and SEQ ID NO: 4, respectively.

Reference Example 4

Establishment of 2D7sc(Fv)2-Producing Expression Cell Lines

20 µg of linearized pCXND3-2D7sc(Fv)2 obtained by digesting the plasmid with PvuI was introduced into CHO cells (DG44 cell line) by electroporation as described below. DG44 cells cultured in CHO-S-SFM-II medium (Invitrogen) were washed twice with ice-cold PBS, and then suspended in PBS to a concentration of $1 \times 10^7$ cells/mL. 20 µg of the above-mentioned plasmid was mixed with this suspension, and then treated with an electric pulse (1.5 KV, 25 µFD). The cells were diluted into appropriate ratios, plated onto a 96-well plate, and cultured in CHO-S-SFM-II medium in the presence of G418 (Invitrogen) at a final concentration of 500 µg/ml. Approximately 30 clones were selected from the grown single colonies, and the expression levels of 2D7sc (Fv)2 in these culture supernatants were investigated by Western blotting, using anti-FLAG antibody (Sigma). The clone with the highest expression level was cultured in nucleic acid-free CHO-S-SFM II medium (invitrogen) containing 5 nM MTX to expand culture scale. The resulting cell line was regarded as a highly productive cell line.

Reference Example 5

Large-Scale Purification of 2D7sc(Fv)2

A sub-confluent, 2D7sc(Fv)2 highly producing CHO cell line in a T-125 flask was transferred to a roller bottle (250 ml of CHO-S-SFM II medium/bottle) to achieve a concentration of $1 \times 10^5$ cells/mL. The cells were cultured at 37° C. and the culture supernatant was collected after 6 days. Dead cells were removed by centrifugation, and the solution was passed through a 0.45 µm filter and then used for purification.

Purification of 2D7sc(Fv)2 was carried out as follows.

First, the collected culture supernatant was applied to a hydroxyapatite column (microprep ceramic Hydroxyapatite type I, Bio-Rad) equilibrated with buffer A (20 mM Na-phosphate pH6.8). After washing the column with buffer A, 2D7sc(Fv)2 was eluted using buffer C (250 mM Na-phosphate pH6.8). The fraction containing 2D7sc(Fv)2 was diluted with an equal amount of buffer A, and then this was applied to Anti-Flag M2 agarose affinity column (Bio-Rad). This column was washed with buffer C (50 mM tris-HCl pH7.4, 150 mM NaCl, 0.01% Tween 20), and then 2D7sc (Fv)2 was eluted with buffer D (100 mM Glycine H3.5, 0.01% Tween 20). The collected sample was immediately neutralized with Tris-HCl pH8.0 to obtain a final concentration of 25 mM. Thereafter, this fraction was concentrated using centriprep YM-10 (AMICON), and then purified by gel filtration chromatography using Superdex200HR (26/60) column (Amersham Pharmacia).

Purification by gel filtration chromatography was performed using PBS containing 0.01% Tween 20. Minibodies produced from the CHO cell line producing high levels of 2D7sc(Fv)2 mostly have an elution peak at around the molecular weight of 52 Kd, which completely matches the peak of the 2D7 diabody also eluted at 52 Kd.

Only the 52 Kd peak fraction separated by gel filtration chromatographic purification was collected, and this was used as the 2D7sc(Fv)2 protein sample. SDS electrophoresis and silver staining using a portion of the collected sample was performed to confirm that the desired protein was purified to 100% purity. The collected purified sample was concentrated using Centriprep YM-10 (AMICON).

INDUSTRIAL APPLICABILITY

Aggregation of antibody molecules can be suppressed to allow antibody molecules to exist as monomers, by using stabilizers comprising meglumine of the present invention. In the development of antibodies as pharmaceuticals, each antibody molecule has to be stabilized so that the aggregation is suppressed to minimum during storage of preparations. The stabilizers of the present invention can stabilize antibody molecules and suppress aggregation even when the concentration of antibodies to be stabilized is very high. Thus, the stabilizers are thought to be very useful in producing antibody preparations. Furthermore, agents comprising meglumine of the present invention also have the effect of stabilizing antibody molecules when the antibody molecules are formulated into solution preparations or freeze-dried preparations. The stabilizers also have the effect of stabilizing antibody molecules against the stress imposed during the freeze-drying process in the formulation of freeze-dried preparations. The stabilizers of the present invention also have the effect of stabilizing entire whole antibodies, antibody fragments, and minibodies, and thus are widely useful in producing antibody preparations.

The pharmaceutical compositions of the present invention, which comprise antibody molecules stabilized by meglumine, are well-preserved, as compared to conventional antibody preparations, because the denaturation and aggregation of antibody molecules are suppressed. Therefore, the degree of activity loss during preservation is expected to be less.

The invention claimed is:

1. A method comprising
   (a) providing a first composition comprising antibody molecules; and
   (b) adding 1-deoxy-1-methylamino-D-glucitol or a salt thereof to the first composition, thereby producing a second composition, wherein the 1-deoxy-1-methylamino-D-glucitol or salt thereof is added to the first composition at a concentration effective to suppress aggregation of the antibody molecules during storage, compared to antibody aggregation during storage in a control composition identical to the second composition except lacking the 1-deoxy-1-methylamino-D-glucitol or salt thereof.

2. The method of claim 1, wherein the concentration of the 1-deoxy-1-methylamino-D-glucitol or salt thereof is effective to limit aggregation of the antibody molecules in the second composition to 2% or less after six months of storage at −20° C.

3. The method of claim 1, further comprising freeze-drying the second composition, to produce a freeze-dried preparation.

4. The method of claim 3, wherein the concentration of the 1-deoxy-1-methylamino-D-glucitol or salt thereof is effective to limit the aggregation of the antibody molecules in the second composition to 5% or less after one month of storage of the freeze-dried preparation at 40° C.

5. The method of claim 1, wherein the antibody molecules are molecules of: a whole antibody, an antibody fragment, a minibody, a modified antibody, or an antibody-like molecule.

6. The method of claim 1, wherein the antibody molecules are molecules of a whole antibody.

7. The method of claim 1, wherein the antibody molecules are molecules of a minibody.

8. The method of claim 1, wherein the second composition is a pharmaceutical composition.

* * * * *